(12) United States Patent
Bissantz et al.

(10) Patent No.: US 8,729,091 B2
(45) Date of Patent: May 20, 2014

(54) 4-PHENOXY-NICOTINAMIDE OR 4-PHENOXY-PYRIMIDINE-5-CARBOXAMIDE COMPOUNDS

(71) Applicant: Hoffmann-La Roche Inc., Nutley, NJ (US)

(72) Inventors: Caterina Bissantz, Village-Neuf (FR); Henrietta Dehmlow, Loerrach (DE); Shawn David Erickson, Leonia, NJ (US); Kyungjin Kim, Livingston, NJ (US); Rainer E. Martin, Basel (CH); Ulrike Obst Sander, Reinach BL (CH); Sherrie Lynn Pietranico-Cole, Montclair, NJ (US); Hans Richter, Grenzach-Wyhlen (DE); Christoph Ullmer, Fischingen (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 13/767,907

(22) Filed: Feb. 15, 2013

(65) Prior Publication Data

US 2013/0150372 A1    Jun. 13, 2013

Related U.S. Application Data

(63) Continuation of application No. 13/005,566, filed on Jan. 13, 2011, now Pat. No. 8,420,647.

(30) Foreign Application Priority Data

Jan. 21, 2010  (EP) ..................................... 10151319

(51) Int. Cl.
*A61K 31/505*    (2006.01)
*A61K 31/4427*   (2006.01)

(52) U.S. Cl.
USPC ............ 514/269; 514/335; 544/333; 546/261

(58) Field of Classification Search
USPC ......................................... 544/333; 546/261
See application file for complete search history.

(56) References Cited

U.S. PATENT DOCUMENTS

| | | | |
|---|---|---|---|
| 5,593,942 | A | 1/1997 | Santel et al. |
| 6,063,848 | A | 5/2000 | Murakami et al. |
| 2004/0204450 | A1 | 10/2004 | Bechle et al. |
| 2010/0105906 | A1 | 4/2010 | Bissantz et al. |

FOREIGN PATENT DOCUMENTS

| | | |
|---|---|---|
| EP | 0829202 | 3/1998 |
| JP | 2004238361 | 8/2004 |
| WO | 97/24404 | 7/1997 |
| WO | 99/24404 | 5/1999 |
| WO | 2004/085401 | 10/2004 |
| WO | 2005/009443 | 2/2005 |
| WO | 2005/009989 | 2/2005 |
| WO | 2008/009407 | 1/2008 |
| WO | 2008/125627 | 10/2008 |
| WO | 2010049302 | 5/2010 |

OTHER PUBLICATIONS

International Search Report for PCT/IP2011/050558 issued Apr. 21, 2011.
Keitel et al., "Biophys. Res. Comm." 372:78-84 ( 2008).
Kawamata et al., "Journal of Biological Chemistry" 278:9435-9440 ( 2003).
Bojanowska et al., "Medical Science Monitor" 8:RA271-278 ( 2005).
Watanabe et al., "Nature" 439:484-489 ( 2006).
Yoshinaga et al., "American Journal Physiology" 263:G695-701.
Kreymann et al., "Lancet" 2:1300-1304 ( 1987).
Hirai et al., Other Database, (Preparation of Pyrimidine-5-Carboxamides & Their Intermediates, XP002632252) 2004.
Pellicciari et al., "Journal of Medicinal Chemistry" 52(24):7958-7961 ( 2009).
Meier et al., "Diabetes Metabolism Research Reviews" 2:91-117 ( 2005).
Katsuma et al., "Biochem. Biophys. Res. Commun." 329(1):386-390 ( 2005).
Bloom et al., Nature 418:650-654 ( 2002).
Grandt et al., "Regulatory Peptides" 51:151-159 ( 1994).
Perry et al., "Current Alzheimer Res." 3:377-385 ( 2005).
Adrian et al., "Gut" 34:1219-1224 ( 1993).

(Continued)

*Primary Examiner* — Brian McDowell

(57) ABSTRACT

This invention relates to novel phenyl amide or pyridyl amide derivatives of the formula

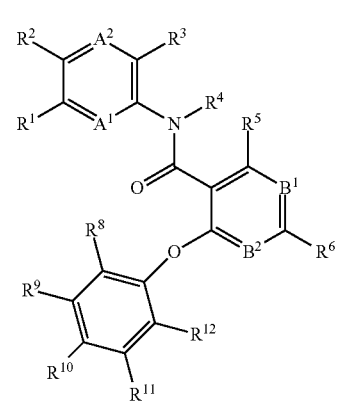

wherein $A^1$, $A^2$, $B^1$, $B^2$ and $R^1$ to $R^{11}$ are as defined in the description and in the claims, as well as pharmaceutically acceptable salts thereof. These compounds are GPBAR1 agonists and can be used as medicaments for the treatment of diseases such as type II diabetes.

12 Claims, No Drawings

(56) References Cited

OTHER PUBLICATIONS

Maruyama et al., "Biochemical & Biophysical Research Communications" 298:714-719 (2002).
Savage et al., "Gut" 28:166-170 (1987).
Thomas et al., "Cell Metabolism" 10(3):167-177 (2009).
Keitel et al., "Hepatology" 45(3):695-704 (2007).
Keitel et al., "Hepatology" 50(3):861-870 (2009).
Plaisancie et al., "Journal of Endocrinology" 145(3):521-526 (1995).
Eberlein et al., "Peptides" 10:797-803 (1989).
The English translation of the Japanese Office Action, issued on Dec. 17, 2013, in the corresponding Japanese application No. 2012-549325.

4-PHENOXY-NICOTINAMIDE OR 4-PHENOXY-PYRIMIDINE-5-CARBOXAMIDE COMPOUNDS

PRIORITY TO RELATED APPLICATION(S)

This application is a continuation application of U.S. Ser. No. 13/005,566, filed Jan. 13, 2011, and claims the benefit of European Patent Application No. 10151319.0, filed Jan. 21, 2010, which are hereby incorporated by reference in their entirety.

FIELD OF THE INVENTION

The present invention relates to novel 4-phenoxy-nicotinamide or 4-phenoxy-pyrimidine-5-carboxamide derivatives, their manufacture, pharmaceutical compositions containing them and their use as medicaments.

The compounds of formula I possess pharmaceutical activity, in particular they are modulators or ligands of the GPBAR1 receptor. More particularly, the compounds are potent GPBAR1 agonists.

BACKGROUND OF THE INVENTION

Diabetes mellitus is an ever-increasing threat to human health. For example, in the United States current estimates maintain that about 16 million people suffer from diabetes mellitus. Type II diabetes also known as non-insulin-dependent diabetes mellitus accounts for approximately 90-95% of diabetes cases, killing about 193,000 U.S. residents each year. Type II diabetes is the seventh leading cause of all deaths. In Western societies, type II diabetes currently affects 6% of the adult population with world-wide frequency expected to grow by 6% per annum. Although there are certain inheritable traits that may predispose particular individuals to developing type II diabetes, the driving force behind the current increase in incidence of the disease is the increased sedentary lifestyle, diet, and obesity now prevalent in developed countries. About 80% of diabetics with type II diabetes are significantly overweight. Also, an increasing number of young people are developing the disease. Type II diabetes is now internationally recognized as one of the major threats to human health in the 21st century.

Type II diabetes manifests as inability to adequately regulate blood-glucose levels and may be characterized by a defect in insulin secretion or by insulin resistance. Namely, those who suffer from Type II diabetes have too little insulin or cannot use insulin effectively. Insulin resistance refers to the inability of the body tissues to respond properly to endogenous insulin. Insulin resistance develops because of multiple factors, including genetics, obesity, increasing age, and having high blood sugar over long periods of time. Type II diabetes, sometimes called mature on set, can develop at any age, but most commonly becomes apparent during adulthood. However, the incidence of type II diabetes in children is rising. In diabetics glucose levels build up in the blood and urine causing excessive urination, thirst, hunger, and problems with fat and protein metabolism. If left untreated, diabetes mellitus may cause life-threatening complications, including blindness, kidney failure, and heart disease.

Type II diabetes is currently treated at several levels. A first level of therapy is through diet and/or exercise, either alone or in combination with therapeutic agents. Such agents may include insulin or pharmaceuticals that lower blood glucose levels. About 49% of individuals with Type II diabetes require oral medications, about 40% require insulin injections or a combination of insulin injections and oral medications, and 10% use diet and exercise alone.

Current therapies include: insulin secretagogues, such as sulphonylureas, which increase insulin production from pancreatic β-cells; glucose-lowering effectors, such as metformin which reduce glucose production from the liver; activators of the peroxisome proliferator-activated receptor γ (PPARγ), such as the thiazolidinediones, which enhances insulin action; and α-glucosidase inhibitors which interfere with gut glucose production. There are, however, deficiencies associated with currently available treatments. For example sulphonylureas and insulin injections can be associated with hypoglycemic episodes and weight gain. Furthermore, patients often lose responsiveness to sulphonylureas over time. Metformin and α-glucosidase inhibitors often lead to gastrointestinal problems and PPARγ agonists tend to cause increased weight gain and edema.

Bile acids (BA) are amphipathic molecules which are synthesized in the liver from cholesterol and stored in the gall bladder until secretion to the duodenum and intestine to play an important role in the solubilization and absorption of dietary fat and lipid-soluble vitamins. Approx. 99% of BA are absorbed again by passive diffusion and active transport in the terminal ileum and transported back to the liver via the portal vein (enterohepatic circulation). In the liver, BA decrease their own biosynthesis from cholesterol through the activation of the farnesoid X receptor alpha (FXRα) and small heterodimer partner (SHP), leading to the transcriptional repression of cholesterol 7α-hydroxylase, the rate-limiting step of BA biosynthesis from cholesterol.

GPBAR1, in the literature termed TGR5, M-BAR or BG37 as well, was recently identified as a G-protein coupled receptor (GPCR) responsive to BA (Kawamata et al., *J. Biol. Chem.* 2003, 278, 9435-9440; Maruyama et al., *Biochem. Biophys. Res. Commun.* 2002, 298, 714-719). GPBAR1 is a G(alpha)s-coupled GPCR and stimulation by ligand binding causes activation of adenylyl cyclase which leads to the elevation of intracellular cAMP and subsequent activation of downstream signaling pathways. The human receptor shares 86, 90, 82, and 83% amino acid identity to bovine, rabbit, rat, and mouse receptor, respectively. GPBAR1 is abundantly expressed in the intestinal tract, monocytes and macrophages, lung, spleen, placenta (Kawamata et al., *J. Biol. Chem.* 2003, 278, 9435-9440). BA induced receptor internalization, intracellular cAMP production and activation of extracellular signal-regulated kinase in GPBAR1-expressing HEK293 and CHO cells.

GPBAR1 was found to be abundantly expressed in monocytes/macrophages from humans and rabbits (Kawamata et al., *J. Biol. Chem.* 2003, 278, 9435-9440), and BA treatment suppressed LPS-induced cytokine production in rabbit alveolar macrophages and human THP-1 cells expressing GPBAR1. These data suggest that bile acids can suppress the macrophage function via activation of GPBAR1. In the liver functional GPBAR1 was found in the plasma membranes of Kupffer cells, mediating inhibition of LPS-induced cytokine expression (Keitel, *Biochem. Biophys. Res. Commun.* 2008, 372, 78-84), and of sinusoidal endothelial cells, where bile salts led to an increase in intracellular cAMP and to the activation and enhanced expression of the endothelial nitric oxide (NO) synthase (Keitel, *Hepatology* 2007, 45, 695-704). Furthermore, GPBAR1 has been detected in cholangiocytes of rat liver (Keitel, *Biochem. Biophys. Res. Commun.* 2008, 372, 78-84). Hydrophobic bile acids, such as taurolithocholic acid, increase cAMP in cholangiocytes suggesting that GPBAR1 may modulate ductal secretion and bile flow. Indeed, GPBAR1 staining colocalized with the cyclic adenosine monophosphate regulated chloride channel cystic fibrosis transmembrane conductance regulator (CFTR) and the apical sodium-dependent bile salt uptake transporter (ASBT). A functional coupling of GPBAR1 to chloride secretion and bile flow has been shown using GPBAR1 agonists (Keitel et al., *Hepatology* 2009 50, 861-870; Pellicciari et al., *J Med Chem* 2009, 52(24), 7958-7961). In summary, GPBAR1 agonists may trigger a protective as well as medicative mechanism in cholestatic livers.

GPBAR1 is expressed in intestinal enteroendocrine cell lines from human (NCI-H716) and murine (STC-1, GLUTag) origin (Maruyama et al., *Biochem. Biophys. Res. Commun.* 2002, 298, 714-719). Stimulation of GPBAR1 by BA stimulated cAMP production in NCI-H716 cells. Intracellular increases in cAMP suggested that BA may induce the secretion of glucagon-like peptide-1 (GLP-1). Indeed, activation of GPBAR1 by BA promoted GLP-1 secretion in STC-1 cells (Katsuma et al., *Biochem. Biophys. Res. Commun.* 2005, 329, 386-390). Receptor-specificity has been demonstrated by RNA interference experiments which revealed that reduced expression of GPBAR1 resulted in diminished secretion of GLP-1. There is compelling evidence that GPBAR1-mediated GLP-1 and PYY release from intestinal L-cells extends to in vivo. In the isolated vascularly perfused rat colon, BAs have been shown to trigger GLP-1 secretion (Plaisancie et al., *J. Endocrin.* 1995, 145, 521-526). Using a combination of pharmacological and genetic gain- and loss-of-function studies in vivo, GPBAR1 signaling was shown to induce GLP-1 release, leading to improved liver and pancreatic function and enhanced glucose tolerance in obese mice (Thomas et al., *Cell Metabolism,* 2009, 10, 167-177). In humans, intracolonic administration of deoxycholate showed marked increases in plasma levels of GLP-1 and the co-secreted PYY (Adrian et al., *Gut* 1993, 34, 1219-1224).

GLP-1 is a peptide secreted from enteroendocrine L cells has been shown to stimulate insulin release in glucose dependent manner in humans (Kreymann et al., *Lancet* 1987, 2, 1300-1304) and studies in experimental animals demonstrated that this incretin hormone is necessary for normal glucose homeostasis. In addition, GLP-1 can exert several beneficial effects in diabetes and obesity, including 1) increased glucose disposal, 2) suppression in glucose production, 3) reduced gastric emptying, 4) reduction in food intake and 5) weight loss. More recently, much research has been focused on the use of GLP-1 in the treatment of conditions and disorders such as diabetes mellitus, stress, obesity, appetite control and satiety, Alzheimer disease, inflammation, and diseases of the central nervous system. (See, for example, Bojanowska et al., *Med. Sci. Monit.* 2005, 8, RA271-8; Perry et al., *Current Alzheimer Res.* 2005, 3, 377-385; and Meier et al., *Diabetes Metab. Res. Rev.* 2005, 2, 91-117). However, the use of a peptide in clinical treatment is limited due to difficult administration, and in vivo stability. Therefore, a small molecule that either mimics the effects of GLP-1 directly, or increases GLP-1 secretion, may be useful in treatment of the variety of conditions or disorders described above, namely diabetes mellitus.

PYY is co-secreted with GLP-1 from intestinal L-cells following a meal. A dipeptidyl peptidase-IV (DPP4) cleavage product of PYY is PYY[3-36] (Eberlein et al. *Peptides* 1989, 10, 797-803) (Grandt et al. *Regul Pept* 1994, 51, 151-159). This fragment constitutes approximately 40% of total PYY-like immunoreactivity in human and canine intestinal extracts and about 36% of total plasma PYY immunoreactivity in a fasting state to slightly over 50% following a meal. PYY[3-36] is reportedly a selective ligand at the Y2 and Y5 receptors. Peripheral administration of PYY reportedly reduces gastric acid secretion, gastric motility, exocrine pancreatic secretion (Yoshinaga et al. *Am J Physiol* 1992, 263, G695-701), gallbladder contraction and intestinal motility (Savage et al. *Gut* 1987, 28, 166-170). It has been demonstrated that Intra-arcuate (IC) or Intra-peritoneal (IP) injection of PYY3-36 reduced feeding in rats and, as a chronic treatment, reduced body weight gain. Intra-venous (IV) infusion (0.8 pmol/kg/min) for 90 min of PYY3-36 reduced food intake in obese and normal human subjects 33% over 24 hours. These finding suggest that the PYY system may be a therapeutic target for the treatment of obesity (Bloom et. al. *Nature* 2002, 418, 650-654).

Furthermore, activation of GPBAR1 might be beneficial for the treatment of obesity and metabolic syndrome. Mice fed a high fat diet (HFD) containing 0.5% cholic acid gained less weight than control mice on HFD alone independent of food intake (Watanabe et al., *Nature* 2006, 439, 484-489). These effects were independent of FXR-alpha, and are likely to results from the binding of BA to GPBAR1. The proposed GPBAR1-mediated mechanism is leading to the subsequent induction of the cAMP-dependent thyroid hormone activating enzyme type 2 (D2) which converts the inactive T3 into the active T4, resulting in the stimulation of the thyroid hormone receptor and promoting energy expenditure. Mice lacking the D2 gene were resistant to cholic acid-induced weight loss. In both rodents and humans, the most thermogenically important tissues (the brown adipose and skeletal muscle) are specifically targeted by this mechanism because they co-express D2 and GPBAR1. The BA-GPBAR1-cAMP-D2 signalling pathway is therefore a crucial mechanism for fine-tuning energy homeostasis that can be targeted to improve metabolic control.

It is therefore an object of the present invention to provide selective, directly acting GPBAR1 agonists. Such agonists are useful as therapeutically active substances, particularly in the treatment and/or prevention of diseases which are associated with the activation of GPBAR1.

SUMMARY OF THE INVENTION

The present invention provides a compound of formula I,

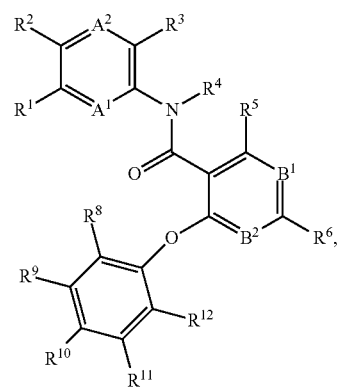

wherein
A$^1$ is CR$^{13}$ or N;
A$^2$ is CR$^{14}$ or N;
R$^1$ and R$^2$ are independently from each other selected from the group consisting of hydrogen, C$_{1-7}$-alkyl, halogen, halogen-C$_{1-7}$-alkyl, cyano and C$_{1-7}$-alkoxy;

$R^{13}$ and $R^{14}$ are independently from each other selected from the group consisting of hydrogen, $C_{1-7}$-alkyl, halogen, halogen-$C_{1-7}$-alkyl, cyano, $C_{1-7}$-alkoxy, amino and $C_{1-7}$-alkylsulfanyl;

$R^3$ is selected from the group consisting of hydrogen, $C_{1-7}$-alkyl, halogen, halogen-$C_{1-7}$-alkyl, $C_{1-7}$-alkoxy, cyano, $C_{3-7}$-cycloalkyl, N-heterocyclyl, five-membered heteroaryl, phenyl and —$NR^{15}R^{16}$, wherein $R^{15}$ and $R^{16}$ independently from each other are selected from hydrogen, $C_{1-7}$-alkyl and $C_{3-7}$-cycloalkyl;

$R^4$ is selected from the group consisting of hydrogen, $C_{1-7}$-alkyl, halogen-$C_{1-7}$-alkyl and $C_{3-7}$-cycloalkyl; or $R^3$ and $R^4$ or $R^3$ and $R^{14}$ together are X—$(CR^{17}R^{18})_n$— and form part of a ring; wherein X is selected from the group consisting of —$CR^{19}R^{20}$—, O, S, C=O and $NR^{21}$;

$R^{17}$ and $R^{18}$ are independently from each other hydrogen or $C_{1-7}$-alkyl;

$R^{19}$ and $R^{20}$ are independently from each other selected from the group consisting of hydrogen, $C_{1-7}$-alkyl, $C_{1-7}$-alkoxycarbonyl, and heterocyclyl optionally substituted by one or two groups selected from $C_{1-7}$-alkyl and halogen, or $R^{19}$ and $R^{20}$ together with the C atom they are attached to form a cyclopropyl or oxetanyl ring or together form a =$CH_2$ or =$CF_2$ group;

$R^{21}$ is selected from the group consisting of hydrogen, $C_{1-7}$-alkyl, halogen-$C_{1-7}$-alkyl, $C_{3-7}$-cycloalkyl optionally substituted by carboxyl-$C_{1-7}$-alkyl or $C_{1-7}$-alkoxycarbonyl, $C_{3-7}$-cycloalkyl-$C_{1-7}$-alkyl wherein the $C_{3-7}$-cycloalkyl is optionally substituted by carboxyl-$C_{1-7}$-alkyl or $C_{1-7}$-alkoxycarbonyl, heterocyclyl, heterocyclyl-$C_{1-7}$-alkyl, heteroaryl, heteroaryl-$C_{1-7}$-alkyl, carboxyl-$C_{1-7}$-alkyl, $C_{1-7}$-alkoxycarbonyl-$C_{1-7}$-alkyl, $C_{1-7}$-alkylcarbonyloxy-$C_{1-7}$-alkyl, $C_{1-7}$-alkylsulfonyl, phenyl optionally substituted by carboxyl-$C_{1-7}$-alkyl or $C_{1-7}$-alkoxycarbonyl, phenylcarbonyl wherein the phenyl is optionally substituted by carboxyl-$C_{1-7}$-alkyl or $C_{1-7}$-alkoxycarbonyl, and phenylsulfonyl wherein the phenyl is optionally substituted by carboxyl-$C_{1-7}$-alkyl or $C_{1-7}$-alkoxycarbonyl, or $R^{21}$ and a $R^{17}$ together are —$(CH_2)_3$— and form part of a ring, or $R^{21}$ together with a pair of $R^{17}$ and $R^{18}$ are —CH=CH—CH= and form part of a ring;

and n is 1, 2 or 3;

$B^1$ is N or $N^+$—$O^-$;

$B^2$ is $CR^7$ or N;

$R^5$, $R^6$ and $R^7$ independently from each other are selected from the group consisting of hydrogen, halogen, $C_{1-7}$-alkyl, $C_{1-7}$-alkoxy, halogen-$C_{1-7}$-alkyl, halogen-$C_{1-7}$-alkoxy, and cyano;

and $R^8$, $R^9$, $R^{10}$, $R^{11}$ and $R^{12}$ are independently from each other selected from the group consisting of hydrogen, $C_{1-7}$-alkyl, $C_{2-7}$-alkenyl, $C_{2-7}$-alkinyl, halogen, halogen-$C_{1-7}$-alkyl, $C_{1-7}$-alkoxy, halogen-$C_{1-7}$-alkoxy, hydroxy, hydroxy-$C_{1-7}$-alkoxy, hydroxy-$C_{1-7}$-alkyl, hydroxy-$C_{3-7}$-alkenyl, hydroxy-$C_{3-7}$-alkinyl, cyano, carboxyl, $C_{1-7}$-alkoxycarbonyl, aminocarbonyl, carboxyl-$C_{1-7}$-alkyl, carboxyl-$C_{2-7}$-alkenyl, carboxyl-$C_{2-7}$-alkinyl, $C_{1-7}$-alkoxycarbonyl-$C_{1-7}$-alkyl, $C_{1-7}$-alkoxycarbonyl-$C_{2-7}$-alkenyl, $C_{1-7}$-alkoxycarbonyl-$C_{2-7}$-alkinyl, carboxyl-$C_{1-7}$-alkoxy, $C_{1-7}$-alkoxycarbonyl-$C_{1-7}$-alkoxy, carboxyl-$C_{1-7}$-alkyl-aminocarbonyl, carboxyl-$C_{1-7}$-alkyl-($C_{1-7}$-alkylamino)-carbonyl, $C_{1-7}$-alkoxycarbonyl-$C_{1-7}$-alkyl-aminocarbonyl, $C_{1-7}$-alkoxycarbonyl-$C_{1-7}$-alkyl-($C_{1-7}$-alkylamino)-carbonyl, carboxyl-$C_{1-7}$-alkyl-aminocarbonyl-$C_{1-7}$-alkyl, carboxyl-$C_{1-7}$-alkyl-($C_{1-7}$-alkylamino)-carbonyl-$C_{1-7}$-alkyl, $C_{1-7}$-alkoxycarbonyl-$C_{1-7}$-alkyl-aminocarbonyl-$C_{1-7}$-alkyl, $C_{1-7}$-alkoxycarbonyl-$C_{1-7}$-alkyl-($C_{1-7}$-alkylamino)-carbonyl-$C_{1-7}$-alkyl, hydroxy-$C_{1-7}$-alkyl-aminocarbonyl, di-(hydroxy-$C_{1-7}$-alkyl)aminocarbonyl, aminocarbonyl-$C_{1-7}$-alkyl-aminocarbonyl, hydroxysulfonyl-$C_{1-7}$-alkyl-aminocarbonyl, hydroxysulfonyl-$C_{1-7}$-alkyl-($C_{1-7}$-alkylamino)-carbonyl, di-($C_{1-7}$-alkoxycarbonyl-$C_{1-7}$-alkyl)-methylaminocarbonyl, phenyl optionally substituted by one to three groups selected from halogen, $C_{1-7}$-alkoxy, carboxyl or $C_{1-7}$-alkoxycarbonyl, phenyl-carbonyl wherein the phenyl is optionally substituted by one to three groups selected from halogen, $C_{1-7}$-alkoxy, carboxyl and $C_{1-7}$-alkoxycarbonyl, phenyl-aminocarbonyl wherein the phenyl is optionally substituted by one to three groups selected from halogen, $C_{1-7}$-alkoxy, carboxyl and $C_{1-7}$-alkoxycarbonyl, phenyl-$C_{1-7}$-alkyl wherein the phenyl is optionally substituted by one to three groups selected from halogen, $C_{1-7}$-alkoxy, carboxyl and $C_{1-7}$-alkoxycarbonyl, phenyl-$C_{2-7}$-alkinyl wherein the phenyl is optionally substituted by one to three groups selected from halogen, $C_{1-7}$-alkoxy, carboxyl and $C_{1-7}$-alkoxycarbonyl, heteroaryl optionally substituted by one to three groups selected from halogen, $C_{1-7}$-alkoxy, carboxyl and $C_{1-7}$-alkoxycarbonyl, heteroaryl-carbonyl wherein the heteroaryl is optionally substituted by one to three groups selected from halogen, $C_{1-7}$-alkoxy, carboxyl and $C_{1-7}$-alkoxycarbonyl, heteroaryl-aminocarbonyl wherein the heteroaryl is optionally substituted by one to three groups selected from halogen, $C_{1-7}$-alkoxy, carboxyl and $C_{1-7}$-alkoxycarbonyl, heteroaryl-$C_{1-7}$-alkyl wherein the heteroaryl is optionally substituted by one to three groups selected from halogen, $C_{1-7}$-alkyl, $C_{1-7}$-alkoxy, carboxyl and $C_{1-7}$-alkoxycarbonyl, heteroaryl-$C_{1-7}$-alkyl-aminocarbonyl wherein the heteroaryl is optionally substituted by one to three groups selected from halogen, $C_{1-7}$-alkoxy, carboxyl and $C_{1-7}$-alkoxycarbonyl, and heteroaryl-carbonyl-$C_{1-7}$-alkyl wherein the heteroaryl is optionally substituted by one to three groups selected from halogen, $C_{1-7}$-alkoxy, carboxyl and $C_{1-7}$-alkoxycarbonyl;

or a pharmaceutically acceptable salt thereof.

The present invention also provides a composition comprising a compound as described above, or a pharmaceutically acceptable salt thereof.

DETAILED DESCRIPTION OF THE INVENTION

The novel compounds of the present invention exceed the compounds known in the art, inasmuch as they are small molecules and they bind to and selectively activate GPBAR1 very efficiently. They are expected to have an enhanced therapeutic potential compared to the compounds already known in the art and can be used for the treatment of diabetes, obesity, metabolic syndrome, hypercholesterolemia, dyslipidemia and a wide range of acute and chronic inflammatory diseases.

Unless otherwise indicated, the following definitions are set forth to illustrate and define the meaning and scope of the various terms used to describe the invention.

The term "halogen" refers to fluorine, chlorine, bromine and iodine, with fluorine, chlorine and bromine being preferred, and with fluorine and chlorine being more preferred.

The term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms. The term "$C_{1-10}$-alkyl" refers to a branched or straight-chain monovalent saturated aliphatic hydrocarbon radical of one to ten carbon atoms, such as e.g., methyl, ethyl, n-propyl, isopropyl, n-butyl, sec-butyl, tert-butyl, pentyl, 1,1,3,3-tetramethyl-butyl and the like. Lower alkyl groups as described below are also preferred alkyl groups.

The term "lower alkyl" or "$C_{1-7}$-alkyl", alone or in combination, signifies a straight-chain or branched-chain alkyl group with 1 to 7 carbon atoms, preferably a straight or branched-chain alkyl group with 1 to 6 carbon atoms and particularly preferred a straight or branched-chain alkyl group with 1 to 4 carbon atoms. Examples of straight-chain and branched $C_{1-7}$ alkyl groups are methyl, ethyl, propyl, isopropyl, butyl, isobutyl, tert.-butyl, the isomeric pentyls, the isomeric hexyls and the isomeric heptyls, preferably methyl and ethyl and most preferred methyl.

The term "lower alkenyl" or "$C_{2-7}$-alkenyl" signifies a straight-chain or branched chain hydrocarbon residue comprising an olefinic bond and 2 to 7, preferably 3 to 6, particularly preferred 3 to 4 carbon atoms. Examples of alkenyl groups are ethenyl, 1-propenyl, 2-propenyl, isopropenyl, 1-butenyl, 2-butenyl, 3-butenyl and isobutenyl. A preferred example is 2-propenyl (allyl).

The term "lower alkinyl" or "$C_{2-7}$-alkinyl" signifies a straight-chain or branched chain hydrocarbon residue comprising a triple bond and 2 to 7, preferably 3 to 7, particularly preferred 3 to 4 carbon atoms. Preferred alkinyl groups are ethinyl and 1-propinyl (—C≡C—CH$_2$).

The term "cycloalkyl" or "$C_{3-7}$-cycloalkyl" denotes a saturated carbocyclic group containing from 3 to 7 carbon atoms, such as cyclopropyl, cyclobutyl, cyclopentyl, cyclohexyl or cycloheptyl. Especially preferred is cyclopropyl.

The term "lower cycloalkylalkyl" or "$C_{3-7}$-cycloalkyl-$C_{1-7}$-alkyl" refers to lower alkyl groups as defined above wherein at least one of the hydrogen atoms of the lower alkyl group is replaced by a cycloalkyl group. Among the preferred lower cycloalkylalkyl groups resides cyclopropylmethyl.

The term "lower alkoxy" or "$C_{1-7}$-alkoxy" refers to the group R'—O—, wherein R' is lower alkyl and the term "lower alkyl" has the previously given significance. Examples of lower alkoxy groups are methoxy, ethoxy, n-propoxy, isopropoxy, n-butoxy, isobutoxy, sec.-butoxy and tert.-butoxy, preferably methoxy.

The term "lower alkylsulfanyl" or "$C_{1-7}$-alkylsulfanyl" defines the group —S—R, wherein R is lower alkyl and the term "lower alkyl" has the previously given meaning. Examples of lower alkylsulfonyl groups are methylsulfanyl (—SCH$_3$) or ethylsulfanyl (—SC$_2$H$_5$).

The term "lower alkoxycarbonyl" or "$C_{1-7}$-alkoxycarbonyl" refers to the group CO—OR' wherein R' is lower alkyl and the term "lower alkyl" has the previously given significance. Preferred lower alkoxycarbonyl groups are methoxycarbonyl or ethoxycarbonyl.

The term "lower alkoxycarbonylalkyl" or "$C_{1-7}$-alkoxycarbonyl-$C_{1-7}$-alkyl" means lower alkyl groups as defined above wherein one of the hydrogen atoms of the lower alkyl group is replaced by $C_{1-7}$-alkoxycarbonyl. A preferred lower alkoxycarbonylalkyl group is —CH$_2$—COOCH$_3$.

The term "lower alkoxycarbonylalkenyl" or "$C_{1-7}$-alkoxycarbonyl-$C_{3-7}$-alkenyl" refers to lower alkenyl groups as defined above but having at least 3 carbon atoms wherein at least one of the hydrogen atoms of the lower alkenyl group is replaced by $C_{1-7}$-alkoxycarbonyl.

The term "lower alkoxycarbonylalkinyl" or "$C_{1-7}$-alkoxycarbonyl-$C_{3-7}$-alkinyl" refers to lower alkinyl groups as defined above but having at least 3 carbon atoms wherein at least one of the hydrogen atoms of the lower alkinyl group is replaced by $C_{1-7}$-alkoxycarbonyl.

The term "lower alkoxycarbonylalkylaminocarbonyl" or "$C_{1-7}$-alkoxycarbonyl-$C_{1-7}$-alkylaminocarbonyl" refers to aminocarbonyl as defined above wherein one of the hydrogen atoms of the amino group is replaced by $C_{1-7}$-alkoxycarbonyl-$C_{1-7}$-alkyl. Preferred lower carboxylalkylaminocarbonyl group is —CO—NH—CH$_2$—COOCH$_3$.

The term "$C_{1-7}$-alkoxycarbonyl-$C_{1-7}$-alkyl-($C_{1-7}$-alkylamino)-carbonyl" refers to a $C_{1-7}$-alkylaminocarbonyl group (—CO—NR—, wherein R is $C_{1-7}$-alkyl) wherein one of the hydrogen atoms of the amino group is replaced by $C_{1-7}$-alkoxycarbonyl-$C_{1-7}$-alkyl.

The term "lower alkoxycarbonylalkylaminocarbonylalkyl" or "$C_{1-7}$-alkoxycarbonyl-$C_{1-7}$-alkylaminocarbonyl-$C_{1-7}$-alkyl" refers to a lower alkyl group wherein one of the hydrogen atoms of the lower alkyl group is replaced by "$C_{1-7}$-alkoxycarbonyl-$C_{1-7}$-alkylaminocarbonyl" as defined above Preferred lower alkoxycarbonylalkylaminocarbonylalkyl group is —CH$_2$—CO—NH—CH$_2$—COOCH$_3$.

The term "$C_{1-7}$-alkoxycarbonyl-$C_{1-7}$-alkyl-($C_{1-7}$-alkylamino)-carbonyl-$C_{1-7}$-alkyl" refers to a lower alkyl group wherein one of the hydrogen atoms of the lower alkyl group is replaced by "$C_{1-7}$-alkoxycarbonyl-$C_{1-7}$-alkyl-($C_{1-7}$-alkylamino)-carbonyl". Preferred group is —CH$_2$—CO—NCH$_3$—CH$_2$—COOCH$_3$.

The term "lower halogenalkyl" or "halogen-$C_{1-7}$-alkyl" refers to lower alkyl groups as defined above wherein at least one of the hydrogen atoms of the lower alkyl group is replaced by a halogen atom, preferably fluoro or chloro, most preferably fluoro. Among the preferred halogenated lower alkyl groups are trifluoromethyl, difluoromethyl, trifluoroethyl, 2,2-difluoroethyl, fluoromethyl and chloromethyl, with trifluoromethyl or difluoromethyl being especially preferred.

The term "lower halogenalkoxy" or "halogen-$C_{1-7}$-alkoxy" refers to lower alkoxy groups as defined above wherein at least one of the hydrogen atoms of the lower alkoxy group is replaced by a halogen atom, preferably fluoro or chloro, most preferably fluoro. Among the preferred halogenated lower alkoxy groups are trifluoromethoxy, difluoromethoxy, fluormethoxy and chloromethoxy, with trifluoromethoxy being especially preferred.

The term hydroxy means the group —OH.

The term "lower hydroxyalkyl" or "hydroxy-$C_{1-7}$-alkyl" refers to lower alkyl groups as defined above wherein at least one of the hydrogen atoms of the lower alkyl group is replaced by a hydroxy group. Among the preferred lower hydroxyalkyl groups are hydroxymethyl or hydroxyethyl.

The term "lower hydroxyalkenyl" or "hydroxy-$C_{3-7}$-alkenyl" refers to lower alkenyl groups as defined above but having at least 3 carbon atoms wherein at least one of the hydrogen atoms of the lower alkenyl group is replaced by a hydroxy group. Among the preferred lower hydroxyalkenyl groups is hydroxyallyl.

The term "lower hydroxyalkinyl" or "hydroxy-$C_{3-7}$-alkinyl" refers to lower alkinyl groups as defined above but having at least 3 carbon atoms wherein at least one of the hydrogen atoms of the lower alkinyl group is replaced by a hydroxy group. Among the preferred lower hydroxyalkinyl groups is —C≡C—CH$_2$OH.

The term "lower hydroxyalkoxy" or "hydroxy-$C_{1-7}$-alkoxy" refers to lower alkoxy groups as defined above wherein at least one of the hydrogen atoms of the lower alkoxy group is replaced by a hydroxy group. A preferred lower hydroxyalkoxy group is 2-hydroxyethoxy.

"Amino" refers to the group —NH$_2$. The term "C$_{1-7}$-alkylamino" means a group —NHR, wherein R is lower alkyl and the term "lower alkyl" has the previously given significance.

The term "aminocarbonyl" refers to the group —CO—NH$_2$.

The term "carboxyl" means the group —COOH.

The term "lower carboxylalkyl" or "carboxyl-C$_{1-7}$-alkyl" refers to lower alkyl groups as defined above wherein at least one of the hydrogen atoms of the lower alkyl group is replaced by a carboxyl group. Among the preferred lower carboxyl alkyl groups are carboxylmethyl (—CH$_2$—COOH) and carboxylethyl (—CH$_2$—CH$_2$—COOH), with carboxylmethyl being especially preferred.

The term "lower carboxylalkenyl" or "carboxyl-C$_{2-7}$-alkenyl" means lower alkenyl groups as defined herein before wherein one of the hydrogen atoms of the lower alkenyl group is replaced by carboxyl. Preferred lower carboxylalkenyl group is —CH=CH—CH$_2$—COOH.

The term "lower carboxylalkinyl" or "carboxyl-C$_{2-7}$-alkinyl" means a lower alkinyl group as defined herein before wherein one of the hydrogen atoms of the lower alkinyl group is replaced by carboxyl. Preferred lower carboxylalkinyl group is —C≡C—CH$_2$—COOH.

The term "lower carboxylalkoxy" or "carboxyl-C$_{1-7}$-alkoxy" refers to lower alkoxy groups as defined above wherein at least one of the hydrogen atoms of the lower alkoxy group is replaced by a carboxyl group. Among the preferred lower carboxylalkoxy groups is 2-carboxyl-2-methylethoxy (—O—C(CH$_3$)$_2$—COOH).

The term "lower carboxylalkylaminocarbonyl" or "carboxyl-C$_{1-7}$-alkylaminocarbonyl" refers to aminocarbonyl as defined above wherein one of the hydrogen atoms of the amino group is replaced by carboxyl-C$_{1-7}$-alkyl. Preferred lower carboxylalkylaminocarbonyl group is —CO—NH—CH$_2$—COOH.

The term "lower carboxylalkyl(alkylamino)carbonyl" or "carboxyl-C$_{1-7}$-alkyl-(C$_{1-7}$-alkylamino)-carbonyl" refers to C$_{1-7}$-alkylaminocarbonyl as defined above wherein the hydrogen atom of the alkylamino group is replaced by carboxyl-C$_{1-7}$-alkyl. Preferred lower carboxylalkyl(alkylamino) carbonyl group is —CO—N(CH$_3$)—CH$_2$—COOH.

The term "lower carboxylalkylaminocarbonylalkyl" or "carboxyl-C$_{1-7}$-alkylamino-carbonyl-C$_{1-7}$-alkyl" refers to a lower alkyl group wherein one of the hydrogen atoms of the lower alkyl group is replaced by "carboxyl-C$_{1-7}$-alkylaminocarbonyl" as defined above Preferred lower carboxylalkylaminocarbonylalkyl group is —CH$_2$—CO—NH—CH$_2$—COOH.

The term "carboxyl-C$_{1-7}$-alkyl-(C$_{1-7}$-alkylamino)-carbonyl-C$_{1-7}$-alkyl" refers to a lower alkyl group wherein one of the hydrogen atoms of the lower alkyl group is replaced by "carboxyl-C$_{1-7}$-alkyl-(C$_{1-7}$-alkylamino)-carbonyl", for example a group of the formula —CH$_2$—CO—NR—CH$_2$—COOH, wherein R is lower alkyl.

The term "lower hydroxyalkylaminocarbonyl" or "hydroxy-C$_{1-7}$-alkylaminocarbonyl" refers to aminocarbonyl as defined above wherein one of the hydrogen atoms of the amino group is replaced by hydroxy-C$_{1-7}$-alkyl. Preferred lower hydroxyalkylaminocarbonyl groups are —CO—NH—CH$_2$—CH$_2$—OH or —CO—NH—CH—(CH$_2$—OH)$_2$.

The term "di-(hydroxy-C$_{1-7}$-alkyl)aminocarbonyl" refers to aminocarbonyl as defined above wherein both of the hydrogen atoms of the amino group are replaced by hydroxy-C$_{1-7}$-alkyl. Preferred di-(hydroxy-C$_{1-7}$-alkyl)aminocarbonyl group is —CO—N(CH$_2$—CH$_2$—OH)$_2$.

The term "lower aminocarbonylalkylaminocarbonyl" or "aminocarbonyl-C$_{1-7}$-alkylaminocarbonyl" refers to aminocarbonyl as defined above wherein one of the hydrogen atoms of the amino group is replaced by aminocarbonyl-C$_{1-7}$-alkyl. A preferred aminocarbonyl-C$_{1-7}$-alkylaminocarbonyl group is —CO—NH—CH$_2$—CH$_2$—CO—NH$_2$.

The term "hydroxysulfonyl" means the group —SO$_2$—OH.

The term "lower hydroxysulfonylalkylaminocarbonyl" or "hydroxysulfonyl-C$_{1-7}$-alkylaminocarbonyl" refers to aminocarbonyl as defined above wherein one of the hydrogen atoms of the amino group is replaced by hydroxysulfonyl-C$_{1-7}$-alkyl. Preferred hydroxysulfonyl-C$_{1-7}$-alkylaminocarbonyl group is —CO—NH—CH$_2$—CH$_2$—SO$_2$—OH.

The term "lower hydroxysulfonylalkyl(alkylamino)carbonyl" or "hydroxysulfonyl-C$_{1-7}$-alkyl-(C$_{1-7}$-alkylamino)-carbonyl" refers to C$_{1-7}$-alkylaminocarbonyl wherein the hydrogen atom of the amino group is replaced by hydroxysulfonyl-C$_{1-7}$-alkyl.

A preferred "di-(C$_{1-7}$-alkoxycarbonyl-C$_{1-7}$-alkyl)-methylaminocarbonyl" group is —CO—NH—CH(—CH$_2$—CH$_2$—CO—OCH$_3$)$_2$.

The term "phenylcarbonyl" refers to the group —CO—R' wherein R' is phenyl.

The term "phenylaminocarbonyl" refers to the group —CO—NHR' wherein R' is phenyl.

The term "lower phenylalkyl" or "phenyl-C$_{2-7}$-alkyl" means lower alkyl groups as defined above wherein one of the hydrogen atoms of the lower alkyl group is replaced by an optionally substituted phenyl group.

The term "lower phenylalkinyl" or "phenyl-C$_{2-7}$-alkenyl" refers to lower alkinyl groups as defined above wherein at least one of the hydrogen atoms of the lower alkinyl group is replaced by optionally substituted phenyl.

The term "heterocyclyl" in general refers to a saturated or partly unsaturated 3-, 4-, 5-, 6- or 7-membered ring which can comprise one, two or three atoms selected from nitrogen, oxygen and/or sulphur. Examples of heterocyclyl rings include azirinyl, azetidinyl, oxetanyl, piperidinyl, piperazinyl, azepinyl, pyrrolidinyl, pyrazolidinyl, imidazolinyl, imidazolidinyl, pyridinyl, pyridazinyl, pyrimidinyl, oxazolidinyl, isoxazolidinyl, morpholinyl, thiazolidinyl, isothiazolidinyl, thiadiazolylidinyl, dihydrofuryl, tetrahydrofuryl, dihydropyranyl, tetrahydropyranyl, and thiamorpholinyl. A preferred heterocyclyl group is oxetanyl.

The term "lower heterocyclylalkyl" or "heterocyclyl-C$_{1-7}$-alkyl" refers to lower alkyl groups as defined above wherein at least one of the hydrogen atoms of the lower alkyl group is replaced by a heterocyclyl group as defined above.

"N-heterocyclyl" means a 3-, 4-, 5-, 6- or 7-membered saturated heterocyclic ring containing a nitrogen atom ("N") and optionally containing a further heteroatom selected from nitrogen, oxygen or sulfur. Preferably, the N-heterocyclyl ring is connected by the nitrogen atom to the carbon atom the ring is attached to. Preferred N-heterocyclyl rings are selected from the group consisting of azirinyl, azetidinyl, pyrrolidinyl, imidazolidinyl, pyrazolidinyl, oxazolidinyl, isoxazolidinyl, thiazolidinyl, isothiazolidinyl, piperidinyl, piperazinyl, morpholinyl, thiomorpholinyl and azepanyl.

The term "heteroaryl" in general refers to an aromatic 5- or 6-membered ring which comprises one, two or three atoms selected from nitrogen, oxygen and/or sulphur, such as pyridyl, pyrazinyl, pyrimidinyl, pyridazinyl, 2-oxo-1,2-dihydropyridinyl, oxazolyl, oxadiazolyl, isoxazolyl, thiadiazolyl, tetrazolyl, pyrazolyl, imidazolyl, furyl, thiazolyl and thienyl. The term "heteroaryl" further refers to bicyclic aromatic groups comprising two 5- or 6-membered rings, in which one or both rings can contain one, two or three atoms selected from nitrogen, oxygen or sulphur, such as quinolinyl, isoquinolinyl, cinnolinyl, pyrazolo[1,5-a]pyridyl, imidazo[1,2-a]pyridyl, quinoxalinyl, benzothiazolyl, benzotriazolyl, indolyl and indazolyl. Preferred heteroaryl group is furyl.

The term "lower heteroarylalkyl" or "heteroaryl-$C_{1-7}$-alkyl" refers to lower alkyl groups as defined above wherein at least one of the hydrogen atoms of the lower alkyl group is replaced by a heteroaryl group as defined above.

The term "heteroarylcarbonyl" refers to the group —CO—R" wherein R" is heteroaryl as defined above.

The term "lower heteroarylcarbonylalkyl" or "heteroarylcarbonyl-$C_{1-7}$-alkyl" refers to lower alkyl groups as defined above wherein at least one of the hydrogen atoms of the lower alkyl group is replaced by a heteroarylcarbonyl group as defined above.

The term "heteroarylaminocarbonyl" refers to the group —CO—NH—R" wherein R" is heteroaryl as defined above.

The term "lower heteroarylalkylaminocarbonyl" or "heteroaryl-$C_{1-7}$-alkylaminocarbonyl" refers to a group —CO—NH—$R^x$ wherein $R^x$ is heteroaryl-$C_{1-7}$-alkyl as defined above.

The term "a five-membered heteroaryl" refers to an aromatic 5-membered ring which comprises at least one nitrogen atom and can in addition comprise one to three atoms selected from nitrogen, oxygen and/or sulphur. Preferred five-membered heteroaryl rings are selected from the group consisting of pyrrolyl, pyrazolyl, imidazolyl, triazolyl, tetrazolyl, oxazolyl, oxadiazolyl, isoxazolyl, thiadiazolyl, and thiazolyl. Preferably, the five-membered heteroaryl ring is connected by a nitrogen atom to the carbon atom the ring is attached to. Most preferably, the five-membered heteroaryl group is pyrrolyl.

Compounds of formula I can form pharmaceutically acceptable salts. The term "pharmaceutically acceptable salts" refers to those salts which retain the biological effectiveness and properties of the free bases or free acids, which are not biologically or otherwise undesirable. The salts are for example acid addition salts of compounds of formula I with physiologically compatible mineral acids, such as hydrochloric acid, sulfuric acid, sulfurous acid or phosphoric acid; or with organic acids, such as methanesulfonic acid, ethanesulfonic acid, p-toluenesulfonic acid, acetic acid, propionic acid, glycolic acid, pyruvic acid, oxylic acid, lactic acid, trifluoroacetic acid, citric acid, fumaric acid, maleic acid, malonic acid, tartaric acid, benzoic acid, cinnamic acid, mandelic acid, succinic acid or salicylic acid. In addition, pharmaceutically acceptable salts may be prepared from addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polymine resins and the like. The compound of formula I can also be present in the form of zwitterions. Particularly preferred pharmaceutically acceptable salts of compounds of formula I are the hydrochloride salts.

The compounds of formula I can also be solvated, e.g., hydrated. The solvation can be effected in the course of the manufacturing process or can take place e.g. as a consequence of hygroscopic properties of an initially anhydrous compound of formula I (hydration). The term "pharmaceutically acceptable salts" also includes physiologically acceptable solvates.

"Isomers" are compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four nonidentical substituents is termed a "chiral center".

In detail, the present invention relates to compounds of formula I,

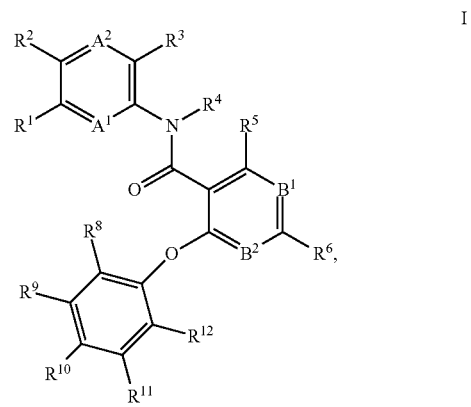

wherein
$A^1$ is $CR^{13}$ or N;
$A^2$ is $CR^{14}$ or N;
$R^1$ and $R^2$ are independently from each other selected from the group consisting of hydrogen, $C_{1-7}$-alkyl, halogen, halogen-$C_{1-7}$-alkyl, cyano and $C_{1-7}$-alkoxy;
$R^{13}$ and $R^{14}$ are independently from each other selected from the group consisting of hydrogen, $C_{1-7}$-alkyl, halogen, halogen-$C_{1-7}$-alkyl, cyano, $C_{1-7}$-alkoxy, amino and $C_{1-7}$-alkylsulfanyl;
$R^3$ is selected from the group consisting of hydrogen, $C_{1-7}$-alkyl, halogen, halogen-$C_{1-7}$-alkyl, $C_{1-7}$-alkoxy, cyano, $C_{3-7}$-cycloalkyl, N-heterocyclyl, five-membered heteroaryl, phenyl and —$NR^{15}R^{16}$, wherein $R^{15}$ and $R^{16}$ independently from each other are selected from hydrogen, $C_{1-7}$-alkyl and $C_{3-7}$-cycloalkyl;
$R^4$ is selected from the group consisting of hydrogen, $C_{1-7}$-alkyl, halogen-$C_{1-7}$-alkyl and $C_{3-7}$-cycloalkyl; or
$R^3$ and $R^4$ or $R^3$ and $R^{14}$ together are —X—$(CR^{17}R^{18})_n$— and form part of a ring; wherein
X is selected from the group consisting of —$CR^{19}R^{20}$—, O, S, C=O and $NR^{21}$;
$R^{17}$ and $R^{18}$ are independently from each other hydrogen or $C_{1-7}$-alkyl;
$R^{19}$ and $R^{20}$ are independently from each other selected from the group consisting of hydrogen, $C_{1-7}$-alkyl, $C_{1-7}$-alkoxycarbonyl, and heterocyclyl optionally substituted by one or two groups selected from $C_{1-7}$-alkyl and halogen,
or $R^{19}$ and $R^{20}$ together with the C atom they are attached to form a cyclopropyl or oxetanyl ring or together form a =$CH_2$ or =$CF_2$ group;
$R^{21}$ is selected from the group consisting of hydrogen, $C_{1-7}$-alkyl, halogen-$C_{1-7}$-alkyl, $C_{3-7}$-cycloalkyl optionally substituted by carboxyl-$C_{1-7}$-alkyl or $C_{1-7}$-alkoxycarbonyl, $C_{3-7}$-cycloalkyl-$C_{1-7}$-alkyl wherein the $C_{3-7}$- cycloalkyl is optionally substituted by carboxyl-$C_{1-7}$-alkyl or $C_{1-7}$-alkoxycarbonyl, heterocyclyl, heterocyclyl-$C_{1-7}$-alkyl, heteroaryl, heteroaryl-$C_{1-7}$-alkyl, carboxyl-$C_{1-7}$-alkyl, $C_{1-7}$-alkoxycarbonyl-$C_{1-7}$-alkyl, $C_{1-7}$-alkylcarbonyloxy-$C_{1-7}$-alkyl, $C_{1-7}$-alkylsulfonyl, phenyl optionally substituted by carboxyl-$C_{1-7}$-alkyl or $C_{1-7}$-alkoxycarbonyl, phenylcarbonyl wherein the phenyl is optionally substituted by carboxyl-$C_{1-7}$-alkyl or $C_{1-7}$-alkoxycarbonyl, and phenylsulfonyl wherein the phenyl is optionally substituted by carboxyl-$C_{1-7}$-alkyl or $C_{1-7}$-alkoxycarbonyl, or $R^{21}$ and a $R^{17}$ together are $-(CH_2)_3-$ and form part of a ring, or $R^{21}$ together with a pair of $R^{17}$ and $R^{18}$ are $-CH=CH-CH=$ and form part of a ring;

and n is 1, 2 or 3;

$B^1$ is N or $N^+-O^-$;

$B^2$ is $CR^7$ or N;

$R^5$, $R^6$ and $R^7$ independently from each other are selected from the group consisting of hydrogen, halogen, $C_{1-7}$-alkyl, $C_{1-7}$-alkoxy, halogen-$C_{1-7}$-alkyl, halogen-$C_{1-7}$-alkoxy, and cyano;

and $R^8$, $R^9$, $R^{10}$, $R^{11}$ and $R^{12}$ are independently from each other selected from the group consisting of hydrogen, $C_{1-7}$-alkyl, $C_{2-7}$-alkenyl, $C_{2-7}$-alkinyl, halogen, halogen-$C_{1-7}$-alkyl, $C_{1-7}$-alkoxy, halogen-$C_{1-7}$-alkoxy, hydroxy, hydroxy-$C_{1-7}$-alkoxy, hydroxy-$C_{1-7}$-alkyl, hydroxy-$C_{3-7}$-alkenyl, hydroxy-$C_{3-7}$-alkinyl, cyano, carboxyl, $C_{1-7}$-alkoxycarbonyl, aminocarbonyl, carboxyl-$C_{1-7}$-alkyl, carboxyl-$C_{2-7}$-alkenyl, carboxyl-$C_{2-7}$-alkinyl, $C_{1-7}$-alkoxycarbonyl-$C_{1-7}$-alkyl, $C_{1-7}$-alkoxycarbonyl-$C_{2-7}$-alkenyl, $C_{1-7}$-alkoxycarbonyl-$C_{2-7}$-alkinyl, carboxyl-$C_{1-7}$-alkoxy, $C_{1-7}$-alkoxycarbonyl-$C_{1-7}$-alkoxy, carboxyl-$C_{1-7}$-alkyl-aminocarbonyl, carboxyl-$C_{1-7}$-alkyl-($C_{1-7}$-alkylamino)-carbonyl, $C_{1-7}$-alkoxycarbonyl-$C_{1-7}$-alkyl-aminocarbonyl, $C_{1-7}$-alkoxycarbonyl-$C_{1-7}$-alkyl-($C_{1-7}$-alkylamino)-carbonyl, carboxyl-$C_{1-7}$-alkyl-aminocarbonyl-$C_{1-7}$-alkyl, carboxyl-$C_{1-7}$-alkyl-($C_{1-7}$-alkylamino)-carbonyl-$C_{1-7}$-alkyl, $C_{1-7}$-alkoxycarbonyl-$C_{1-7}$-alkyl-aminocarbonyl-$C_{1-7}$-alkyl, $C_{1-7}$-alkoxycarbonyl-$C_{1-7}$-alkyl-($C_{1-7}$-alkylamino)-carbonyl-$C_{1-7}$-alkyl, hydroxy-$C_{1-7}$-alkyl-aminocarbonyl, di-(hydroxy-$C_{1-7}$-alkyl)aminocarbonyl, aminocarbonyl-$C_{1-7}$-alkyl-aminocarbonyl, hydroxysulfonyl-$C_{1-7}$-alkyl-aminocarbonyl, hydroxysulfonyl-$C_{1-7}$-alkyl-($C_{1-7}$-alkyl-amino)-carbonyl, di-($C_{1-7}$-alkoxycarbonyl-$C_{1-7}$-alkyl)-methylaminocarbonyl, phenyl optionally substituted by one to three groups selected from halogen, $C_{1-7}$-alkoxy, carboxyl or $C_{1-7}$-alkoxycarbonyl, phenyl-carbonyl wherein the phenyl is optionally substituted by one to three groups selected from halogen, $C_{1-7}$-alkoxy, carboxyl and $C_{1-7}$-alkoxycarbonyl, phenyl-aminocarbonyl wherein the phenyl is optionally substituted by one to three groups selected from halogen, $C_{1-7}$-alkoxy, carboxyl and $C_{1-7}$-alkoxycarbonyl, phenyl-$C_{1-7}$-alkyl wherein the phenyl is optionally substituted by one to three groups selected from halogen, $C_{1-7}$-alkoxy, carboxyl and $C_{1-7}$-alkoxycarbonyl, phenyl-$C_{2-7}$-alkinyl wherein the phenyl is optionally substituted by one to three groups selected from halogen, $C_{1-7}$-alkoxy, carboxyl and $C_{1-7}$-alkoxycarbonyl, heteroaryl optionally substituted by one to three groups selected from halogen, $C_{1-7}$-alkoxy, carboxyl and $C_{1-7}$-alkoxycarbonyl, heteroaryl-carbonyl wherein the heteroaryl is optionally substituted by one to three groups selected from halogen, $C_{1-7}$-alkoxy, carboxyl and $C_{1-7}$-alkoxycarbonyl, heteroaryl-aminocarbonyl wherein the heteroaryl is optionally substituted by one to three groups selected from halogen, $C_{1-7}$-alkoxy, carboxyl and $C_{1-7}$-alkoxycarbonyl, heteroaryl-$C_{1-7}$-alkyl wherein the heteroaryl is optionally substituted by one to three groups selected from halogen, $C_{1-7}$-alkyl, $C_{1-7}$-alkoxy, carboxyl and $C_{1-7}$-alkoxycarbonyl, heteroaryl-$C_{1-7}$-alkyl-aminocarbonyl wherein the heteroaryl is optionally substituted by one to three groups selected from halogen, $C_{1-7}$-alkoxy, carboxyl and $C_{1-7}$-alkoxycarbonyl, and heteroaryl-carbonyl-$C_{1-7}$-alkyl wherein the heteroaryl is optionally substituted by one to three groups selected from halogen, $C_{1-7}$-alkoxy, carboxyl and $C_{1-7}$-alkoxycarbonyl;

and pharmaceutically acceptable salts thereof.

Compounds of formula I according to the present invention include those, wherein $A^1$ is $CR^{13}$ and $A^2$ is $CR^{14}$ or wherein $A^1$ is $CR^{13}$ and $A^2$ is N, with $R^{13}$ and $R^{14}$ being independently from each other selected from the group consisting of hydrogen, $C_{1-7}$-alkyl, halogen, halogen-$C_{1-7}$-alkyl, cyano, $C_{1-7}$-alkoxy, amino and $C_{1-7}$-alkylsulfanyl.

Preferred are those compounds of formula I according to the present invention, wherein $A^1$ is $CR^{13}$ and $A^2$ is $CR^{14}$ and wherein $R^{13}$ and $R^{14}$ are independently from each other selected from the group consisting of hydrogen, halogen, halogen-$C_{1-7}$-alkyl and $C_{1-7}$-alkoxy. These are compounds of the formula

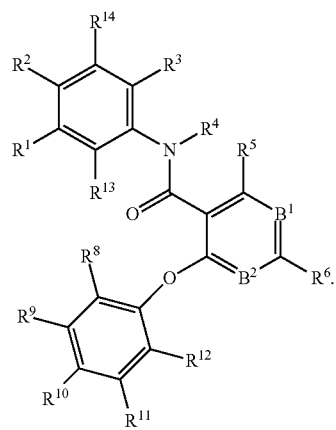

I-a

Furthermore, compounds of formula I are preferred, wherein $A^1$ is $CR^{13}$, $A^2$ is N, and $R^{13}$ is selected from the group consisting of hydrogen, halogen, halogen-$C_{1-7}$-alkyl and $C_{1-7}$-alkoxy. These are compounds of the formula

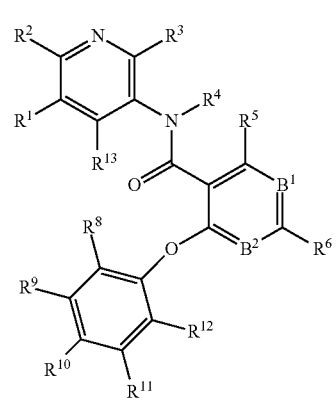

I-b

In addition, compounds of formula I are preferred, wherein $R^1$ and $R^2$ are independently from each other selected from the group consisting of hydrogen, halogen and halogen-$C_{1-7}$-alkyl.

Compounds of formula I are further preferred, wherein $R^3$ and $R^4$ together are —X—$(CR^{17}R^{18})_n$— and form part of a ring; wherein X is —$CR^{19}R^{20}$— or —$NR^{21}$—;

$R^{17}$ and $R^{18}$ are independently from each other hydrogen or $C_{1-7}$-alkyl;

$R^{19}$ and $R^{20}$ are independently from each other selected from the group consisting of hydrogen, $C_{1-7}$-alkyl, $C_{1-7}$-alkoxycarbonyl, and heterocyclyl optionally substituted by one or two groups selected from $C_{1-7}$-alkyl and halogen, or $R^{19}$ and $R^{20}$ together with the C atom they are attached to form a cyclopropyl or oxetanyl ring or together form a =$CH_2$ or =$CF_2$ group;

$R^{21}$ is selected from the group consisting of hydrogen, $C_{1-7}$-alkyl, halogen-$C_{1-7}$-alkyl, $C_{3-7}$-cycloalkyl optionally substituted by carboxyl-$C_{1-7}$-alkyl or $C_{1-7}$-alkoxycarbonyl, $C_{3-7}$-cycloalkyl-$C_{1-7}$-alkyl wherein the $C_{3-7}$-cycloalkyl is optionally substituted by carboxyl-$C_{1-7}$-alkyl or $C_{1-7}$-alkoxycarbonyl, heterocyclyl, heterocyclyl-$C_{1-7}$-alkyl, heteroaryl, heteroaryl-$C_{1-7}$-alkyl, carboxyl-$C_{1-7}$-alkyl, $C_{1-7}$-alkoxycarbonyl-$C_{1-7}$-alkyl, $C_{1-7}$-alkylcarbonyloxy-$C_{1-7}$-alkyl, $C_{1-7}$-alkylsulfonyl, phenyl optionally substituted by carboxyl-$C_{1-7}$-alkyl or $C_{1-7}$-alkoxycarbonyl, phenylcarbonyl wherein the phenyl is optionally substituted by carboxyl-$C_{1-7}$-alkyl or $C_{1-7}$-alkoxycarbonyl, and phenylsulfonyl wherein the phenyl is optionally substituted by carboxyl-$C_{1-7}$-alkyl or $C_{1-7}$-alkoxycarbonyl, or $R^{21}$ and a $R^{17}$ together are —$(CH_2)_3$— and form part of a ring, or $R^{21}$ together with a pair of $R^{17}$ and $R^{18}$ are —CH=CH—CH= and form part of a ring;

and n is 1, 2 or 3.

Within this group, compounds are preferred, wherein X is —$NR^{21}$—, $R^{21}$ is selected from the group consisting of hydrogen, $C_{1-7}$-alkyl, $C_{3-7}$-cycloalkyl optionally substituted by carboxyl-$C_{1-7}$-alkyl or $C_{1-7}$-alkoxycarbonyl, $C_{3-7}$-cycloalkyl-$C_{1-7}$-alkyl, wherein the $C_{3-7}$-cycloalkyl is optionally substituted by carboxyl-$C_{1-7}$-alkyl or $C_{1-7}$-alkoxycarbonyl, and $C_{1-7}$-alkylsulfonyl, $R^{17}$ and $R^{18}$ are independently from each other hydrogen or methyl, and n is 2. These are compounds having the formula

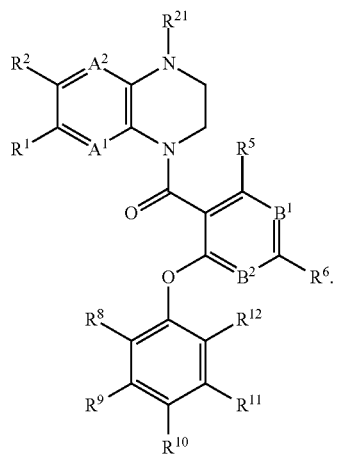

I-c

In an embodiment within this group, $R^{17}$ and $R^{18}$ are both hydrogen.

Furthermore, compounds of formula I are especially preferred, wherein X is —$CH_2$—, $R^{17}$ and $R^{18}$ are each independently hydrogen or methyl, and n is 2. These are compounds of the formula

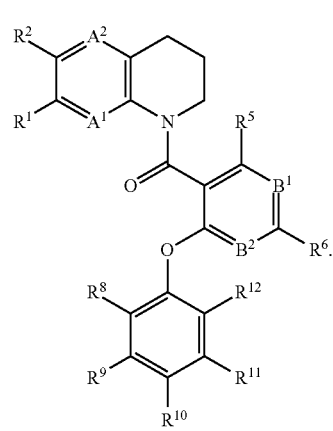

I-d

In an embodiment within this group, $R^{17}$ and $R^{18}$ are both hydrogen.

In addition, compounds of formula I according to the invention are preferred, wherein $R^3$ and $R^{14}$ together are —X—$(CR^{17}R^{18})_n$— and form part of a ring; wherein X is —$NR^{21}$—, $R^{21}$ is selected from the group consisting of hydrogen, $C_{1-7}$-alkyl and $C_{3-7}$-cycloalkyl, $R^{17}$ and $R^{18}$ are independently from each other hydrogen or methyl, and n is 2. These are the compounds of the formula

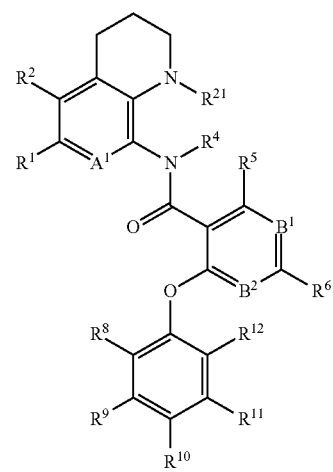

I-e

In an embodiment within this group, $R^{17}$ and $R^{18}$ are both hydrogen, and n is 2.

$R^4$ is preferably hydrogen or $C_{1-7}$-alkyl. More preferably, $R^4$ is methyl.

Further preferred compounds of formula I of the present invention are those, wherein $R^3$ is selected from the group consisting of hydrogen, $C_{1-7}$-alkyl, $C_{1-7}$-alkoxy, N-heterocyclyl and —$NR^{15}R^{16}$, wherein $R^{15}$ and $R^{16}$ independently from each other are selected from hydrogen, $C_{1-7}$-alkyl and $C_{3-7}$-cycloalkyl, and $R^4$ is hydrogen or methyl, more preferably methyl.

Furthermore, compounds of formula I are preferred, wherein $B^1$ is N or $N^+$—$O^-$ and $B^2$ is $CR^7$, with $R^7$ being selected from the group consisting of hydrogen, halogen and $C_{1-7}$-alkyl. More preferably, $B^1$ is N. These are compounds of the formula

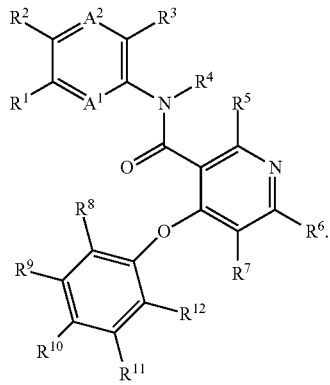

I-f

Also preferred are compounds of formula I of the present invention, wherein $B^1$ is N and $B^2$ is N.

These are compounds of the formula

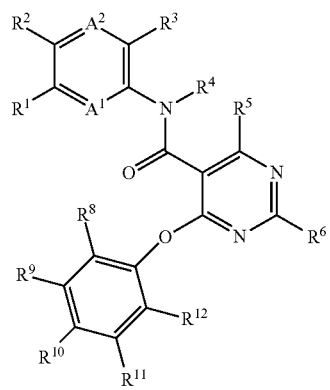

I-g $R^5$ and $R^6$ are independently from each other selected from the group consisting of hydrogen, halogen, $C_{1-7}$-alkyl, $C_{1-7}$-alkoxy, halogen-$C_{1-7}$-alkyl, halogen-$C_{1-7}$-alkoxy, and cyano. Preferred are compounds of formula I, wherein $R^5$ and $R^6$ are independently from each other selected from the group consisting of hydrogen, halogen and $C_{1-7}$-alkyl.

Compounds of the present invention are further preferred, wherein and at least one or, in case $R^4$ is hydrogen or $C_{1-7}$-alkyl, at least two of $R^8$, $R^9$, $R^{10}$, $R^{11}$ and $R^{12}$ are selected from the group consisting of
$C_{1-7}$-alkyl, $C_{2-7}$-alkenyl, $C_{2-7}$-alkinyl, halogen, halogen-$C_{1-7}$-alkyl, $C_{1-7}$-alkoxy, halogen-$C_{1-7}$-alkoxy, hydroxy, hydroxy-$C_{1-7}$-alkoxy, hydroxy-$C_{1-7}$-alkyl, hydroxy-$C_{3-7}$-alkenyl, hydroxy-$C_{3-7}$-alkinyl, cyano, carboxyl, $C_{1-7}$-alkoxycarbonyl, aminocarbonyl, carboxyl-$C_{1-7}$-alkyl, carboxyl-$C_{2-7}$-alkenyl, carboxyl-$C_{2-7}$-alkinyl, $C_{1-7}$-alkoxycarbonyl-$C_{1-7}$-alkyl, $C_{1-7}$-alkoxycarbonyl-$C_{2-7}$-alkenyl, $C_{1-7}$-alkoxycarbonyl-$C_{2-7}$-alkinyl, carboxyl-$C_{1-7}$-alkoxy, $C_{1-7}$-alkoxycarbonyl-$C_{1-7}$-alkoxy, carboxyl-$C_{1-7}$-alkyl-aminocarbonyl, carboxyl-$C_{1-7}$-alkyl-($C_{1-7}$-alkylamino)-carbonyl, $C_{1-7}$-alkoxycarbonyl-$C_{1-7}$-alkyl-aminocarbonyl, $C_{1-7}$-alkoxycarbonyl-$C_{1-7}$-alkyl-($C_{1-7}$-alkylamino)-carbonyl, carboxyl-$C_{1-7}$-alkyl-aminocarbonyl-$C_{1-7}$-alkyl, carboxyl-$C_{1-7}$-alkyl-($C_{1-7}$-alkylamino)-carbonyl-$C_{1-7}$-alkyl, $C_{1-7}$-alkoxycarbonyl-$C_{1-7}$-alkyl-aminocarbonyl-$C_{1-7}$-alkyl, $C_{1-7}$-alkoxycarbonyl-$C_{1-7}$-alkyl-($C_{1-7}$-alkylamino)-carbonyl-$C_{1-7}$-alkyl, hydroxy-$C_{1-7}$-alkyl-aminocarbonyl, di-(hydroxy-$C_{1-7}$-alkyl)aminocarbonyl, aminocarbonyl-$C_{1-7}$-alkyl-aminocarbonyl, hydroxysulfonyl-$C_{1-7}$-alkyl-aminocarbonyl, hydroxysulfonyl-$C_{1-7}$-alkyl-($C_{1-7}$-alkyl-amino)-carbonyl, di-($C_{1-7}$-alkoxycarbonyl-$C_{1-7}$-alkyl)-methylaminocarbonyl, phenyl optionally substituted by one to three groups selected from halogen, $C_{1-7}$-alkoxy, carboxyl and $C_{1-7}$-alkoxycarbonyl, phenyl-carbonyl wherein the phenyl is optionally substituted by one to three groups selected from halogen, $C_{1-7}$-alkoxy, carboxyl and $C_{1-7}$-alkoxycarbonyl, phenyl-aminocarbonyl wherein the phenyl is optionally substituted by one to three groups selected from halogen, $C_{1-7}$-alkoxy, carboxyl and $C_{1-7}$-alkoxycarbonyl, phenyl-$C_{1-7}$-alkyl wherein the phenyl is optionally substituted by one to three groups selected from halogen, $C_{1-7}$-alkoxy, carboxyl and $C_{1-7}$-alkoxycarbonyl, phenyl-$C_{2-7}$-alkinyl wherein the phenyl is optionally substituted by one to three groups selected from halogen, $C_{1-7}$-alkoxy, carboxyl and $C_{1-7}$-alkoxycarbonyl, heteroaryl optionally substituted by one to three groups selected from halogen, $C_{1-7}$-alkoxy, carboxyl and $C_{1-7}$-alkoxycarbonyl, heteroaryl-carbonyl wherein the heteroaryl is optionally substituted by one to three groups selected from halogen, $C_{1-7}$-alkoxy, carboxyl and $C_{1-7}$-alkoxycarbonyl, heteroaryl-aminocarbonyl wherein the heteroaryl is optionally substituted by one to three groups selected from halogen, $C_{1-7}$-alkoxy, carboxyl and $C_{1-7}$-alkoxycarbonyl, heteroaryl-$C_{1-7}$-alkyl wherein the heteroaryl is optionally substituted by one to three groups selected from halogen, $C_{1-7}$-alkyl, $C_{1-7}$-alkoxy, carboxyl and $C_{1-7}$-alkoxycarbonyl, heteroaryl-$C_{1-7}$-alkyl-aminocarbonyl wherein the heteroaryl is optionally substituted by one to three groups selected from halogen, $C_{1-7}$-alkoxy, carboxyl and $C_{1-7}$-alkoxycarbonyl, and heteroaryl-carbonyl-$C_{1-7}$-alkyl wherein the heteroaryl is optionally substituted by one to three groups selected from halogen, $C_{1-7}$-alkoxy, carboxyl and $C_{1-7}$-alkoxycarbonyl, and the other ones of $R^8$, $R^9$, $R^{10}$, $R^{11}$ and $R^{12}$ are hydrogen.

More preferably, compounds of formula I are those, wherein at least two of $R^8$, $R^9$, $R^{10}$, $R^{11}$ and $R^{12}$ are selected from the group consisting of halogen, hydroxy, hydroxy-$C_{1-7}$-alkoxy, hydroxy-$C_{1-7}$-alkyl, cyano, carboxyl, $C_{1-7}$-alkoxycarbonyl, aminocarbonyl, carboxyl-$C_{1-7}$-alkoxy, $C_{1-7}$-alkoxycarbonyl-$C_{1-7}$-alkoxy, carboxyl-$C_{1-7}$-alkyl-aminocarbonyl, carboxyl-$C_{1-7}$-alkyl-($C_{1-7}$-alkylamino)-carbonyl, $C_{1-7}$-alkoxycarbonyl-$C_{1-7}$-alkyl-aminocarbonyl, hydroxy-$C_{1-7}$-alkyl-aminocarbonyl, di-(hydroxy-$C_{1-7}$-alkyl)aminocarbonyl, aminocarbonyl-$C_{1-7}$-alkyl-aminocarbonyl, hydroxysulfonyl-$C_{1-7}$-alkyl-aminocarbonyl, hydroxysulfonyl-$C_{1-7}$-alkyl-($C_{1-7}$-alkyl-amino)-carbonyl, di-($C_{1-7}$-alkoxycarbonyl-$C_{1-7}$-alkyl)-methylaminocarbonyl, phenyl-aminocarbonyl wherein the phenyl is optionally substituted by one to three groups selected from halogen, $C_{1-7}$-alkoxy, carboxyl and $C_{1-7}$-alkoxycarbonyl, heteroaryl-aminocarbonyl wherein the heteroaryl is optionally substituted by one to three groups selected from halogen, $C_{1-7}$-alkoxy, carboxyl and $C_{1-7}$-alkoxycarbonyl, heteroaryl-$C_{1-7}$-alkyl wherein the heteroaryl is optionally substituted by one to three groups selected from halogen, $C_{1-7}$-alkyl, $C_{1-7}$-alkoxy, carboxyl and $C_{1-7}$-alkoxycarbonyl, heteroaryl-$C_{1-7}$-alkyl-aminocarbonyl wherein the heteroaryl is optionally substituted by one to three groups selected from halogen, $C_{1-7}$-alkoxy, carboxyl and $C_{1-7}$-alkoxycarbonyl, and heteroaryl-carbonyl-$C_{1-7}$-alkyl wherein the heteroaryl is optionally substituted by one to three groups selected from halogen, $C_{1-7}$-alkoxy, carboxyl and $C_{1-7}$-alkoxycarbonyl, and the other ones of $R^8$, $R^9$, $R^{10}$, $R^{11}$ and $R^{12}$ are hydrogen.

Especially preferred are compounds of formula I, wherein $R^8$ and $R^{11}$ are halogen and $R^9$, $R^{10}$ and $R^{12}$ are hydrogen.

Examples of preferred compounds are the following:
[4-(2,5-dichloro-phenoxy)-pyridin-3-yl]-(3,4-dihydro-2H-quinolin-1-yl)-methanone,
[4-(2,5-dichloro-phenoxy)-pyridin-3-yl]-(6,7-difluoro-3,4-dihydro-2H-quinolin-1-yl)-methanone,
[4-(2,5-dichloro-phenoxy)-pyridin-3-yl]-(3,4-dihydro-2H-quinoxalin-1-yl)-methanone,
[4-(2,5-dichloro-phenoxy)-pyridin-3-yl]-(4-methyl-3,4-dihydro-2H-quinoxalin-1-yl)-methanone,
2-{-[4-(2,5-dichloro-phenoxy)-pyridine-3-carbonyl]-3,4-dihydro-2H-quinoxalin-1-ylmethyl}-cyclopropanecarboxylic acid ethyl ester,
(4-cyclopropylmethyl-3,4-dihydro-2H-quinoxalin-1-yl)-[4-(2,5-dichloro-phenoxy)-pyridin-3-yl]-methanone,
[4-(2,5-dichloro-phenoxy)-pyridin-3-yl]-(4-methanesulfonyl-3,4-dihydro-2H-quinoxalin-1-yl)-methanone,
(4-cyclopropyl-3,4-dihydro-2H-quinoxalin-1-yl)-[4-(2,5-dichloro-phenoxy)-pyridin-3-yl]-methanone,
(6-chloro-4-cyclopropyl-7-fluoro-3,4-dihydro-2H-quinoxalin-1-yl)-[4-(2,5-dichloro-phenoxy)-pyridin-3-yl]-methanone,
[4-(2,5-dichloro-phenoxy)-1-oxy-pyridin-3-yl]-(3,4-dihydro-2H-quinolin-1-yl)-methanone,
(6-chloro-4-cyclopropyl-3,4-dihydro-2H-quinoxalin-1-yl)-[4-(2,5-dichloro-phenoxy)-pyridin-3-yl]-methanone,
and pharmaceutically-acceptable salts thereof.

Examples of preferred compounds also include the following:
4-(2,5-dichloro-phenoxy)-N-(5-fluoro-2-methoxy-phenyl)-N-methyl-nicotinamide,
4-(2,5-dichloro-phenoxy)-N-methyl-N-o-tolyl-nicotinamide,
4-(2,5-dichloro-phenoxy)-N-(2-methoxy-phenyl)-N-methyl-nicotinamide,
4-(2,5-dichloro-phenoxy)-N-(2-methoxy-pyridin-3-yl)-N-methyl-nicotinamide,
4-(2,5-dichloro-phenoxy)-N-(2-dimethylamino-phenyl)-N-methyl-nicotinamide,
4-(2,5-dichloro-phenoxy)-N-methyl-N-(2-piperidin-1-yl-phenyl)-nicotinamide,
N-(3,5-Bis-trifluoromethyl-phenyl)-4-(2,5-dichloro-phenoxy)-N-methyl-nicotinamide,
4-(2,5-dichloro-phenoxy)-N-(4,5-difluoro-2-methoxy-phenyl)-N-methyl-nicotinamide,
N-(5-chloro-2-dimethylamino-phenyl)-4-(2,5-dichloro-phenoxy)-N-methyl-nicotinamide,
4-(2,5-dichloro-phenoxy)-N-(4,5-difluoro-2-methylamino-phenyl)-N-methyl-nicotinamide,
4-(2,5-dichloro-phenoxy)-N-(1,2,3,4-tetrahydro-quinolin-8-yl)-nicotinamide,
4-(2,5-dichloro-phenoxy)-N-(2-dimethylamino-pyridin-3-yl)-N-methyl-nicotinamide,
4-(2,5-dichloro-phenoxy)-N-methyl-N-(1,2,3,4-tetrahydro-quinolin-8-yl)-nicotinamide,
N-[4-chloro-2-(cyclopropyl-methyl-amino)-5-fluoro-phenyl]-4-(2,5-dichloro-phenoxy)-N-methyl-nicotinamide,
and pharmaceutically-acceptable salts thereof.

Examples of preferred compounds also include the following:
[4-(4-bromo-2,5-dichloro-phenoxy)-pyridin-3-yl]-(4-cyclopropyl-3,4-dihydro-2H-quinoxalin-1-yl)-methanone,
2,5-dichloro-4-[3-(4-cyclopropyl-3,4-dihydro-2H-quinoxaline-1-carbonyl)-pyridin-4-yloxy]-benzoic acid methyl ester,
4-chloro-5-[3-(4-cyclopropyl-3,4-dihydro-2H-quinoxaline-1-carbonyl)-pyridin-4-yloxy]-phthalic acid dimethyl ester,
{2,5-dichloro-4-[3-(4-cyclopropyl-3,4-dihydro-2H-quinoxaline-1-carbonyl)-pyridin-4-yloxy]-benzoylamino}-acetic acid methyl ester,
{2,5-dichloro-4-[3-(4-cyclopropyl-3,4-dihydro-2H-quinoxaline-1-carbonyl)-pyridin-4-yloxy]-benzoylamino}-acetic acid,
({2,5-dichloro-4-[3-(4-cyclopropyl-3,4-dihydro-2H-quinoxaline-1-carbonyl)-pyridin-4-yloxy]-benzoyl}-methyl-amino)-acetic acid methyl ester,
({2,5-dichloro-4-[3-(4-cyclopropyl-3,4-dihydro-2H-quinoxaline-1-carbonyl)-pyridin-4-yloxy]-benzoyl}-methyl-amino)-acetic acid,
3-{2,5-dichloro-4-[3-(4-cyclopropyl-3,4-dihydro-2H-quinoxaline-1-carbonyl)-pyridin-4-yloxy]-benzoylamino}-propionic acid ethyl ester,
and pharmaceutically-acceptable salts thereof.

Examples of preferred compounds also include the following:
3-{2,5-dichloro-4-[3-(4-cyclopropyl-3,4-dihydro-2H-quinoxaline-1-carbonyl)-pyridin-4-yloxy]-benzoylamino}-propionic acid,
2-{2,5-dichloro-4-[3-(4-cyclopropyl-3,4-dihydro-2H-quinoxaline-1-carbonyl)-pyridin-4-yloxy]-benzoylamino}-ethanesulfonic acid,
2-({2,5-dichloro-4-[3-(4-cyclopropyl-3,4-dihydro-2H-quinoxaline-1-carbonyl)-pyridin-4-yloxy]-benzoyl}-methyl-amino)-ethanesulfonic acid,
3-{2,5-dichloro-4-[3-(4-cyclopropyl-3,4-dihydro-2H-quinoxaline-1-carbonyl)-pyridin-4-yloxy]-benzoylamino}-propane-1-sulfonic acid,
and pharmaceutically-acceptable salts thereof.

Examples of preferred compounds also include the following:
2,5-dichloro-4-[3-(4-cyclopropyl-3,4-dihydro-2H-quinoxaline-1-carbonyl)-pyridin-4-yloxy]-N-(1H-tetrazol-5-yl)-benzamide,
2,5-dichloro-4-[3-(4-cyclopropyl-3,4-dihydro-2H-quinoxaline-1-carbonyl)-pyridin-4-yloxy]-N-(1H-tetrazol-5-ylmethyl)-benzamide,
4-{2,5-dichloro-4-[3-(4-cyclopropyl-3,4-dihydro-2H-quinoxaline-1-carbonyl)-pyridin-4-yloxy]-benzoylamino}-butyric acid,
4-{2,5-dichloro-4-[3-(4-cyclopropyl-3,4-dihydro-2H-quinoxaline-1-carbonyl)-pyridin-4-yloxy]-benzoylamino}-1-methyl-1H-pyrrole-2-carboxylic acid methyl ester,
4-{2,5-dichloro-4-[3-(4-cyclopropyl-3,4-dihydro-2H-quinoxaline-1-carbonyl)-pyridin-4-yloxy]-benzoylamino}-1-methyl-1H-pyrrole-2-carboxylic acid,
4-{2,5-dichloro-4-[3-(4-cyclopropyl-3,4-dihydro-2H-quinoxaline-1-carbonyl)-pyridin-4-yloxy]-benzoylamino}-benzoic acid methyl ester,
4-{2,5-dichloro-4-[3-(4-cyclopropyl-3,4-dihydro-2H-quinoxaline-1-carbonyl)-pyridin-4-yloxy]-benzoylamino}-benzoic acid,
2-{2,5-dichloro-4-[3-(4-cyclopropyl-3,4-dihydro-2H-quinoxaline-1-carbonyl)-pyridin-4-yloxy]-benzoylamino}-4-methyl-thiazole-5-carboxylic acid ethyl ester,
2-{2,5-dichloro-4-[3-(4-cyclopropyl-3,4-dihydro-2H-quinoxaline-1-carbonyl)-pyridin-4-yloxy]-benzoylamino}-4-methyl-thiazole-5-carboxylic acid,
5-{2,5-dichloro-4-[3-(4-cyclopropyl-3,4-dihydro-2H-quinoxaline-1-carbonyl)-pyridin-4-yloxy]-benzoylamino}-[1,3,4]thiadiazole-2-carboxylic acid ethyl ester,
2,5-dichloro-4-[3-(4-cyclopropyl-3,4-dihydro-2H-quinoxaline-1-carbonyl)-pyridin-4-yloxy]-N-[1,3,4]thiadiazol-2-yl-benzamide,
2,5-dichloro-4-[3-(4-cyclopropyl-3,4-dihydro-2H-quinoxaline-1-carbonyl)-pyridin-4-yloxy]-N-(2-hydroxy-ethyl)-benzamide,
2,5-dichloro-4-[3-(4-cyclopropyl-3,4-dihydro-2H-quinoxaline-1-carbonyl)-pyridin-4-yloxy]-N,N-bis-(2-hydroxy-ethyl)-benzamide,
2,5-dichloro-4-[3-(4-cyclopropyl-3,4-dihydro-2H-quinoxaline-1-carbonyl)-pyridin-4-yloxy]-N-(2-hydroxy-1-hydroxymethyl-ethyl)-benzamide,
2,5-dichloro-4-[3-(4-cyclopropyl-3,4-dihydro-2H-quinoxaline-1-carbonyl)-pyridin-4-yloxy]-benzamide, N-(2-carbamoyl-ethyl)-2,5-dichloro-4-[3-(4-cyclopropyl-3,4-dihydro-2H-quinoxaline-1-carbonyl)-pyridin-4-yloxy]-benzamide,
4-{2,5-dichloro-4-[3-(4-cyclopropyl-3,4-dihydro-2H-quinoxaline-1-carbonyl)-pyridin-4-yloxy]-benzoylamino}-heptanedioic acid dimethyl ester,
(4-cyclopropyl-3,4-dihydro-2H-quinoxalin-1-yl)-[4-(2,5-dichloro-4-hydroxymethyl-phenoxy)-pyridin-3-yl]-methanone,
2,5-dichloro-4-[3-(4-cyclopropyl-3,4-dihydro-2H-quinoxaline-1-carbonyl)-pyridin-4-yloxy]-benzonitrile,
(4-cyclopropyl-3,4-dihydro-2H-quinoxalin-1-yl)-[4-(2,5-dichloro-4-hydroxy-phenoxy)-pyridin-3-yl]-methanone,
{2,5-dichloro-4-[3-(4-cyclopropyl-3,4-dihydro-2H-quinoxaline-1-carbonyl)-pyridin-4-yloxy]-phenoxy}-acetic acid ethyl ester,
{2,5-dichloro-4-[3-(4-cyclopropyl-3,4-dihydro-2H-quinoxaline-1-carbonyl)-pyridin-4-yloxy]-phenoxy}-acetic acid,
2-{2,5-dichloro-4-[3-(4-cyclopropyl-3,4-dihydro-2H-quinoxaline-1-carbonyl)-pyridin-4-yloxy]-phenoxy}-2-methyl-propionic acid ethyl ester,
2-{2,5-dichloro-4-[3-(4-cyclopropyl-3,4-dihydro-2H-quinoxaline-1-carbonyl)-pyridin-4-yloxy]-phenoxy}-2-methyl-propionic acid,
(4-cyclopropyl-3,4-dihydro-2H-quinoxalin-1-yl)-{4-[2,5-dichloro-4-(2-hydroxy-ethoxy)-phenoxy]-pyridin-3-yl}-methanone,
(4-cyclopropyl-3,4-dihydro-2H-quinoxalin-1-yl)-[4-(2,5-dichloro-phenoxy)-6-methyl-pyridin-3-yl]-methanone,
[4-(4-bromo-2,5-dichloro-phenoxy)-6-methyl-pyridin-3-yl]-(4-cyclopropyl-3,4-dihydro-2H-quinoxalin-1-yl)-methanone,
2,5-dichloro-4-[5-(4-cyclopropyl-3,4-dihydro-2H-quinoxaline-1-carbonyl)-2-methyl-pyridin-4-yloxy]-benzoic acid methyl ester,
2,5-dichloro-4-[5-(4-cyclopropyl-3,4-dihydro-2H-quinoxaline-1-carbonyl)-2-methyl-pyridin-4-yloxy]-benzoic acid,
3-{2,5-dichloro-4-[5-(4-cyclopropyl-3,4-dihydro-2H-quinoxaline-1-carbonyl)-2-methyl-pyridin-4-yloxy]-benzoylamino}-propionic acid ethyl ester,
3-{2,5-dichloro-4-[5-(4-cyclopropyl-3,4-dihydro-2H-quinoxaline-1-carbonyl)-2-methyl-pyridin-4-yloxy]-benzoylamino}-propionic acid,
{2,5-dichloro-4-[5-(4-cyclopropyl-3,4-dihydro-2H-quinoxaline-1-carbonyl)-2-methyl-pyridin-4-yloxy]-benzoylamino}-acetic acid methyl ester,
{2,5-dichloro-4-[5-(4-cyclopropyl-3,4-dihydro-2H-quinoxaline-1-carbonyl)-2-methyl-pyridin-4-yloxy]-benzoylamino}-acetic acid,
2,5-dichloro-4-[5-(4-cyclopropyl-3,4-dihydro-2H-quinoxaline-1-carbonyl)-2-methyl-pyridin-4-yloxy]-N-(1H-tetrazol-5-yl)-benzamide,
2,5-dichloro-4-[5-(4-cyclopropyl-3,4-dihydro-2H-quinoxaline-1-carbonyl)-2-methyl-pyridin-4-yloxy]-N-(1H-tetrazol-5-ylmethyl)-benzamide,
[2-chloro-4-(2,5-dichloro-phenoxy)-6-methyl-pyridin-3-yl]-(4-cyclopropyl-3,4-dihydro-2H-quinoxalin-1-yl)-methanone,
[6-chloro-4-(2,5-dichloro-phenoxy)-pyridin-3-yl]-(3,4-dihydro-2H-quinolin-1-yl)-methanone,
(4-cyclopropyl-3,4-dihydro-2H-quinoxalin-1-yl)-[4-(2,5-dichloro-phenoxy)-1-oxy-pyridin-3-yl]-methanone,
[4-(2,5-dichloro-phenoxy)-pyrimidin-5-yl]-(3,4-dihydro-2H-quinolin-1-yl)-methanone,
[4-(2,5-dichloro-phenoxy)-pyrimidin-5-yl]-(6-fluoro-3,4-dihydro-2H-quinolin-1-yl)-methanone,
[4-(2,5-dichloro-phenoxy)-pyrimidin-5-yl]-(3,4-dihydro-2H-quinoxalin-1-yl)-methanone,
[4-(2,5-dichloro-phenoxy)-pyrimidin-5-yl]-(4-methyl-3,4-dihydro-2H-quinoxalin-1-yl)-methanone,
4-(2,5-dichloro-phenoxy)-pyrimidine-5-carboxylic acid (2-methoxy-pyridin-3-yl)-methyl-amide and pharmaceutically acceptable salts thereof.

Particularly advantageous compounds of formula I of the present invention are the following:
[4-(2,5-dichloro-phenoxy)-pyridin-3-yl]-(4-methyl-3,4-dihydro-2H-quinoxalin-1-yl)-methanone,
(4-cyclopropylmethyl-3,4-dihydro-2H-quinoxalin-1-yl)-[4-(2,5-dichloro-phenoxy)-pyridin-3-yl]-methanone,
(4-cyclopropyl-3,4-dihydro-2H-quinoxalin-1-yl)-[4-(2,5-dichloro-phenoxy)-pyridin-3-yl]-methanone,
(6-chloro-4-cyclopropyl-3,4-dihydro-2H-quinoxalin-1-yl)-[4-(2,5-dichloro-phenoxy)-pyridin-3-yl]-methanone,
[4-(4-bromo-2,5-dichloro-phenoxy)-pyridin-3-yl]-(4-cyclopropyl-3,4-dihydro-2H-quinoxalin-1-yl)-methanone,
{2,5-dichloro-4-[3-(4-cyclopropyl-3,4-dihydro-2H-quinoxaline-1-carbonyl)-pyridin-4-yloxy]-benzoylamino}-acetic acid,
3-{2,5-dichloro-4-[3-(4-cyclopropyl-3,4-dihydro-2H-quinoxaline-1-carbonyl)-pyridin-4-yloxy]-benzoylamino}-propionic acid,
2,5-dichloro-4-[3-(4-cyclopropyl-3,4-dihydro-2H-quinoxaline-1-carbonyl)-pyridin-4-yloxy]-N-(1H-tetrazol-5-yl)-benzamide,
2,5-dichloro-4-[3-(4-cyclopropyl-3,4-dihydro-2H-quinoxaline-1-carbonyl)-pyridin-4-yloxy]-N-(1H-tetrazol-5-ylmethyl)-benzamide,
4-{2,5-dichloro-4-[3-(4-cyclopropyl-3,4-dihydro-2H-quinoxaline-1-carbonyl)-pyridin-4-yloxy]-benzoylamino}-1-methyl-1H-pyrrole-2-carboxylic acid,
4-{2,5-dichloro-4-[3-(4-cyclopropyl-3,4-dihydro-2H-quinoxaline-1-carbonyl)-pyridin-4-yloxy]-benzoylamino}-benzoic acid,
2-{2,5-dichloro-4-[3-(4-cyclopropyl-3,4-dihydro-2H-quinoxaline-1-carbonyl)-pyridin-4-yloxy]-benzoylamino}-4-methyl-thiazole-5-carboxylic acid,
2,5-dichloro-4-[3-(4-cyclopropyl-3,4-dihydro-2H-quinoxaline-1-carbonyl)-pyridin-4-yloxy]-benzonitrile,
(4-cyclopropyl-3,4-dihydro-2H-quinoxalin-1-yl)-[4-(2,5-dichloro-phenoxy)-6-methyl-pyridin-3-yl]-methanone,
3-{2,5-dichloro-4-[5-(4-cyclopropyl-3,4-dihydro-2H-quinoxaline-1-carbonyl)-2-methyl-pyridin-4-yloxy]-benzoylamino}-propionic acid,
2,5-dichloro-4-[5-(4-cyclopropyl-3,4-dihydro-2H-quinoxaline-1-carbonyl)-2-methyl-pyridin-4-yloxy]-N-(1H-tetrazol-5-yl)-benzamide,
(4-cyclopropyl-3,4-dihydro-2H-quinoxalin-1-yl)-[4-(2,5-dichloro-phenoxy)-1-oxy-pyridin-3-yl]-methanone,
[4-(2,5-dichloro-phenoxy)-pyrimidin-5-yl]-(4-methyl-3,4-dihydro-2H-quinoxalin-1-yl)-methanone,
and pharmaceutically acceptable salts thereof.

The pharmaceutically acceptable salts of the compounds of formula I also individually constitute advantageous compounds of the present invention.

Compounds of formula I can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbens or eluant). The invention embraces all of these forms.

It will be appreciated, that the compounds of general formula I in this invention may be derivatized at functional groups to provide derivatives which are capable of conversion back to the parent compound in vivo. Physiologically acceptable and metabolically labile derivatives, which are capable of producing the parent compounds of general formula I in vivo are also within the scope of this invention.

A further aspect of the present invention is the process for the manufacture of compounds of formula I as defined above, which process comprises a) reacting a carboxylic acid of the formula II

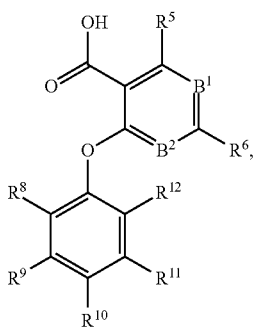

wherein $B^1$, $B^2$ and $R^5$ to $R^{12}$ are as defined above, with an amine of the formula III

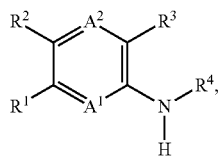

wherein $A^1$, $A^2$ and $R^1$ to $R^4$ are as defined above, in the presence of a coupling reagent under basic conditions to obtain a compound of the formula I

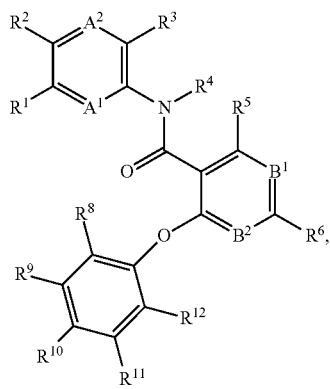

wherein $A^1$, $A^2$, $B^1$, $B^2$ and $R^1$ to $R^{12}$ are as defined above, and, if desired,
converting the compound obtained into a pharmaceutically acceptable salt.
or, alternatively,
b) coupling a compound of the formula IV

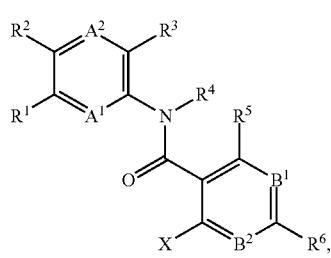

wherein $A^1$, $A^2$, $B^1$, $B^2$ and $R^1$ to $R^6$ are as defined above and X means a halogen atom or sulfonate, with a phenol of the formula V

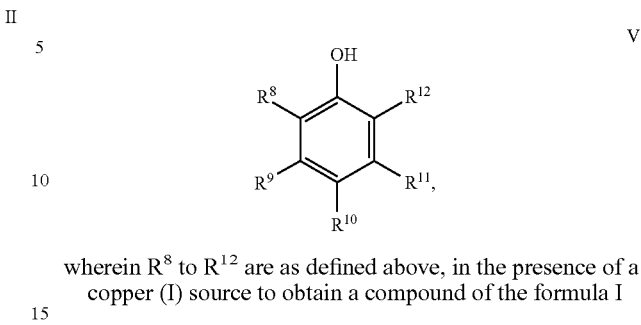

wherein $R^8$ to $R^{12}$ are as defined above, in the presence of a copper (I) source to obtain a compound of the formula I

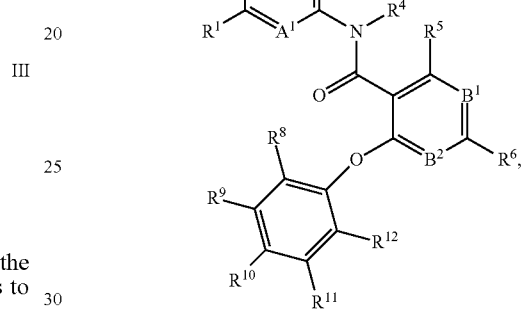

wherein $A^1$, $A^2$, $B^1$, $B^2$ and $R^1$ to $R^{12}$ are as defined above, and, if desired,
converting the compound obtained into a pharmaceutically acceptable salt.

Appropriate coupling agents are for example N,N'-carbonyldiimidazole (CDI), N,N'-dicyclohexylcarbodiimide (DCC), N-(3-dimethylaminopropyl)-N'-ethyl-carbodiimide-hydrochloride (EDCI), O-(benzotriazol-1-yl)-N,N,N',N'-tetramethyluronium tetrafluoroborate (TBTU), 1-[bis(dimethylamino)methylene]-1H-1,2,3-triazolo[4,5-b]pyridinium-3-oxide hexafluorophosphate (HATU), 1-hydroxy-1,2,3-benzotriazole (HOBT), 2-chloro-1-methylpyridinium iodide or benzotriazol-1-yloxytris(dimethylamino)phosphonium hexafluorophoshate (BOP). "Under basic conditions" means the presence of a base such as diisopropylethylamine, triethylamine, N-methylmorpholine or 4-(dimethylamino)-pyridine. The reaction is carried out in a suitable solvent such as for example N,N-dimethylformamide (DMF), dimethylacetamide (DMAc), dichloromethane or dioxane, at temperatures between 0° C. and ambient temperature.

A copper (I) source means a copper (I) salt such as copper (I) bromide or copper (I) iodide or copper (I) complexes such as tetrakis(acetonitrile)copper(I) hexafluorophosphate. The coupling is preferably carried out under heating or microwave assisted heating (typically to a temperature between 100 and 200° C., or up to the boiling temperature of the solvent) in an aprotic solvent such as N,N-dimethylformamide (DMF), dimethylacetamide (DMAc), N-methylpyrrolidone (NMP), ethylene glycol, acetonitrile and THF or mixtures thereof. Optionally a tertiary amine such as triethylamine, N-ethyl diisopropylamine (Hünigs base) or pyridine is also present.

The invention further relates to compounds of formula I as defined above obtainable according to a process as defined above.

In more detail, compounds of formula I according to the present invention can be prepared by the methods and procedures given below. A typical procedure for the preparation of compounds of formula I is illustrated in Scheme 1.

Scheme 1

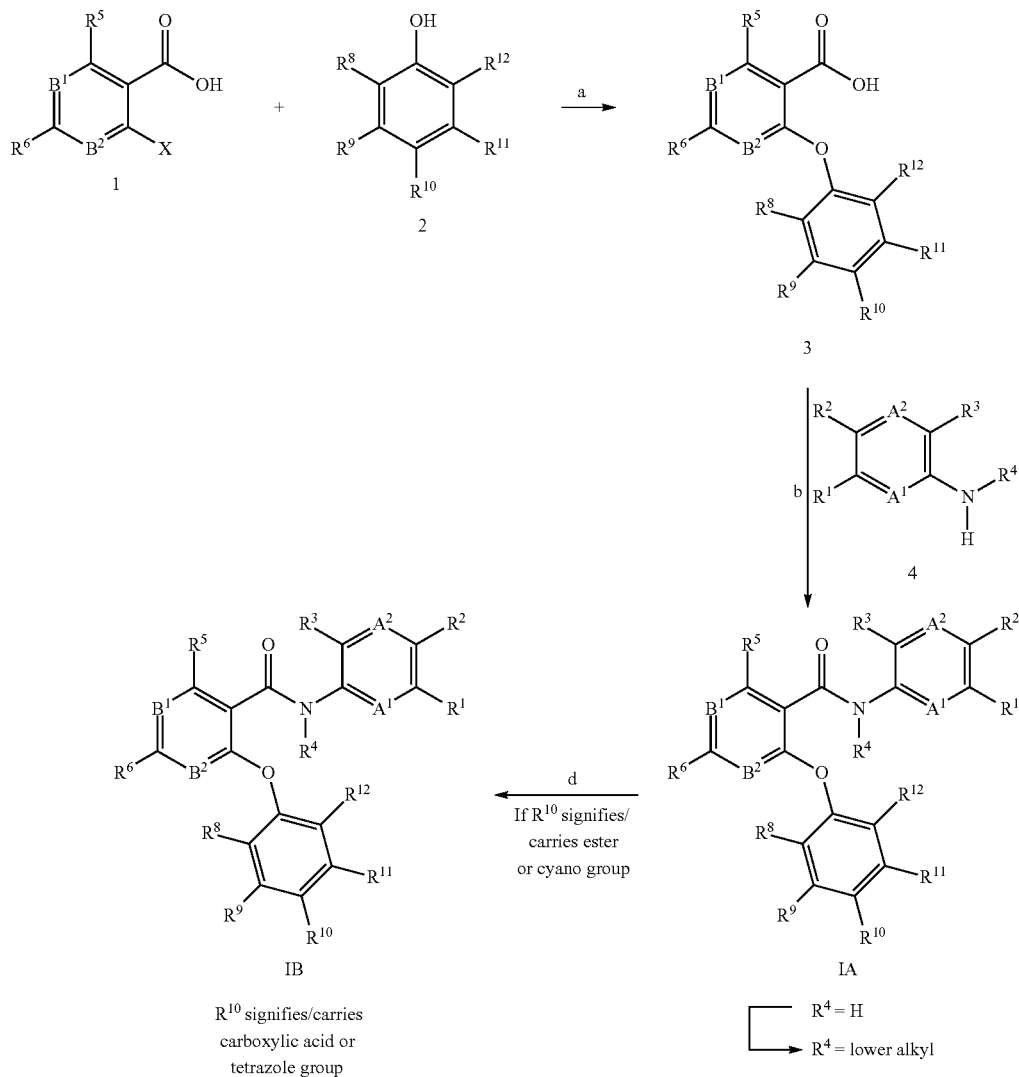

Compounds of general formula IA and IB can be prepared for example as outlined in Scheme 1 by reacting nicotinic acids of the general structure 1 in which X usually signifies a halogen such as iodine, bromine or chlorine with phenols 2 to provide bi-aryl ethers 3 (step a). In order to enhance the rate of conversion heating might be applied, whereby conventional heating or microwave assisted heating might be employed using a suitable microwave irradiation apparatus. Furthermore the reaction can be conducted in the presence of or without solvent (typically an aprotic polar solvent such as DMF (N,N-dimethylformamide), DMAc (dimethylacetamide), NMP (N-methylpyrrolidone), ethylene glycol, acetonitrile and THF or mixtures thereof; in some cases also a less polar solvent such as toluene might be appropriate) and in the presence of or without a tertiary amine base such as triethylamine, N,N-diisopropylethylamine (Huenig's base) or pyridine and in the presence of or without a copper(I) source such as copper(I) bromide or copper(I) iodide. In some cases it might be advisable to conduct the reaction in the presence of copper (I) complexes with higher solubility such as tetrakis(acetonitrile)copper(I) hexafluorophosphate (e.g., US 06/028 7297 A1 (Johnson & Johnson)). Said reaction might be conducted with or without copper metal (e.g., copper(0) nanopowder). Alternatively, the copper-mediated C(aryl)-O coupling reaction can be executed under basic conditions by using potassium- or cesium carbonate, potassium hydroxide, sodium methoxide, potassium tert-butylate or sodium hydride (nucleophilic aromatic substitution type reaction), whereby X is a suitable leaving group such as chlorine, bromine, iodine, $OSO_2$alkyl, $OSO_2$fluoroalkyl, $OSO_2$aryl, mesylate (methanesulfonate) or triflate (trifluoromethanesulfonate). The starting materials of general structure 1 (e.g., 4-chloro- or 4-bromo-nicotinic acids) are known compounds and are commercially available or can be prepared by numerous methods using conventional reaction procedures generally known in the art. For instance, the carboxylic acid function in pyridine derivatives 1 might be prepared from the corresponding benzonitriles or from the corresponding carboxylic esters by applying standard reaction conditions used for such type of conversions known to a person skilled in the art such as, e.g. by acid catalyzed hydrolysis (e.g., sulfuric acid or hydrochloric acid) or by stirring with alkaline hydroxides (e.g., lithium hydroxide, sodium hydroxide, potassium hydroxide) in a solvent mixture consisting typically of tetrahydrofuran and water, optionally in the presence of alcohols such as methanol or ethanol, whereby conventional heating or heating by microwave irradiation might be applied. These reactions can take place over a wide range of temperatures ranging from ambient temperature to the reflux temperature of the solvent employed. The phenols of formula 2 are also known compounds and are commercially available or can be prepared by numerous methods using conventional reaction procedures generally known in the art.

Amide coupling of bi-aryl ether intermediates 3 with optionally substituted aryl- or heteroaryl-amines 4 (either commercially available or accessible by methods described in references or by methods known in the art) gives access to target structures of general structure IA (step b). Amide couplings of this type are widely described in the literature (e.g., Comprehensive Organic Transformations: A Guide to Functional Group Preparations, $2^{nd}$ Edition, Richard C. Larock, John Wiley & Sons, New York, N.Y. 1999) and can be accomplished by employing the usage of coupling reagents such as, e.g., N,N-carbonyldiimidazole (CDI), N,N-dicyclohexylcarbodiimide (DCC), 1-(3-dimethylaminopropyl)-3-ethylcarbodiimide hydrochloride (EDCI), 1-[bis(dimethylamino)methylene]-1H-1,2,3-triazolo[4,5-b]pyridinium-3-oxide hexafluorophosphate (HATU), 1-hydroxy-1,2,3-benzotriazole (HOBT), O-benzotriazol-1-yl-N,N,N,N-tetramethyluronium tetrafluoroborate (TBTU) or 2-chloro-1-methylpyridinium iodide (Mukaiyama reagent; E. Bald, K. Saigo and T. Mukaiyama *Chem. Lett.* 1975, 4, 1163-1166) in a suitable solvent like, e.g., N,N-dimethylformamide (DMF), dimethylacetamide (DMAc), dichloromethane or dioxane, optionally in the presence of a base (e.g., triethylamine, N,N-diisopropylethylamine (Huenig's base) or 4-(dimethylamino)pyridine). Alternatively, target structures IA can be obtained by converting intermediates 3 into their acid chlorides by treatment with, e.g., thionyl chloride, neat or optionally in a solvent such as, e.g., dichloromethane and reaction of the acid chloride with amines 4 in an appropriate solvent such as, e.g., dichloromethane or DMF (N,N-dimethylformamide) and a base such as, e.g., triethylamine, N,N-diisopropylethylamine (Huenig's base), pyridine diisopropylethylamine, 4-(dimethylamino)pyridine or lithium bis(trimethylsilyl)amide whereby theses reactions can take place over a wide range of temperatures ranging from ambient temperature to the reflux temperature of the solvent employed.

In cases where aniline 4 is a primary amine ($R^4$=H) leading to secondary amides, alkylation (e.g., methylation, $R^4$=Me) of the amide bond can be achieved by reaction with alkyl halides (e.g., methyl iodide or methyl bromide) in the presence of a base such as, e.g. sodium hydride or potassium tert-butoxide in an appropriate solvent like DMF (N,N-dimethylformamide), THF or mixtures thereof, at room temperature to elevated temperatures (step c).

Alternatively, compounds IA in which $R^4$ signifies a lower alkyl group can be obtained by amide coupling of intermediates 3 with secondary aryl- or heteroaryl-amines 4 ($R^4$ as defined before) applying the conditions described before. Amines of this type are either commercially available or can be prepared by methods described in literature.

In those cases where the substituent $R^{10}$ in compounds of formula IA signifies or carries a carboxylic ester functionality (e.g. an alkyl ester such as, e.g. methyl, ethyl or tert-butyl), the ester functionality can be cleaved under basic (e.g. methyl or ethyl esters with lithium or sodium hydroxide in polar solvents such as, e.g. methanol, water or tetrahydrofuran or mixtures of said solvents) or under acidic conditions (e.g. a tert-butyl ester using concentrated hydrochloric acid in tetrahydrofuran or formic acid in an appropriate solvent such as alcohols like, e.g. isopropanol) to furnish compounds IB (step d). Further esters include, but are not limited to, e.g. allyl or benzyl esters that can be cleaved by methods known to those skilled in the art and as described for example in "Protective Groups in Organic Chemistry" by T. W. Greene and P.G.M. Wutts, $2^{nd}$ Ed., 1991, Wiley N.Y.) Optionally the substituent $R^{10}$ in compounds of formula IA can signify or carry a cyano group which can be either hydrolyzed to the carboxylic acid under basic (e.g. with aqueous sodium or lithium hydroxide) or under acidic conditions (e.g. hydrochloric or sulphuric acid), or can be converted to the corresponding tetrazole using standard procedures such as, e.g. by treatment with sodium azide in the presence of a Lewis acid (e.g. zinc(II) bromide) or ammonium chloride in water or organic solvents like dichloromethane or N,N-dimethylformamide at temperatures between 0° C. and the boiling point of the solvent to furnish compounds IB (step d). Compounds IB in which $R^{10}$ carries a tetrazole group can be also prepared by amide coupling of intermediates 3 with amino- or amino-alkyl-substituted tetrazoles, that are either commercially available or can be prepared by literature methods. The tetrazole group in amino- or amino-alkyl-substituted tetrazoles can be optionally protected, for example with a triphenylmethyl (trityl) protective group that can be cleaved off after the reaction step applying methods known to those skilled in the art and as described in literature.

Scheme 2

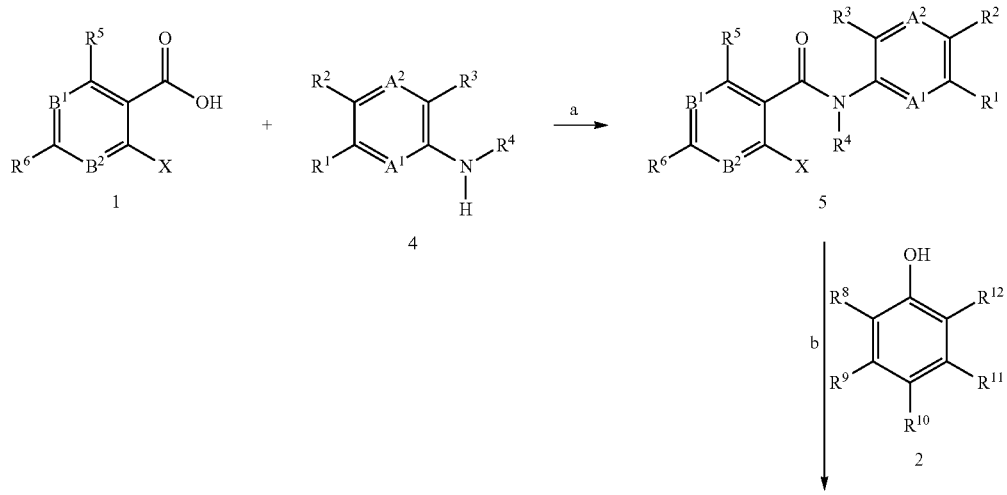

-continued

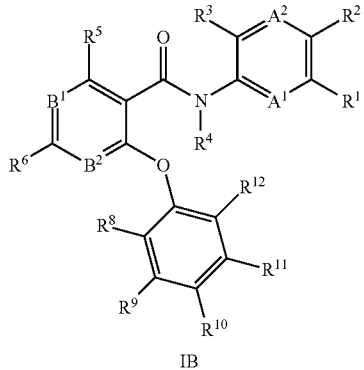

IB

R[10] signifies/carries
carboxylic acid or
tetrazole group

← d
If R[10] signifies/
carries ester
or cyano group

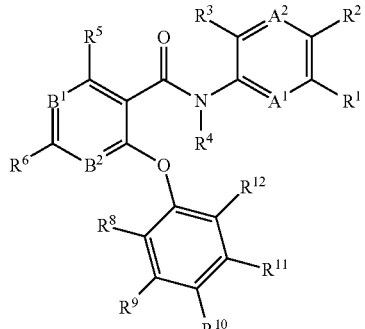

IA

R[4] = H
→ R[4] = lower alkyl

Synthesis of structures of formula IA and IB can also be accomplished as outlined in Scheme 2, employing an inverted reaction sequence, namely by first forming the amide bond between pyridyl carboxylic acids 1 and aryl- or heteroaryl-amines 4 (step a), followed by copper-mediated C(pyridyl)-O coupling of the resulting intermediates 5 with phenols 2 (step b). This provides then access to the target structures IA, which in case of a secondary amide (if primary amines 4 were used) can optionally be further alkylated applying the methods described before (step c). In cases where the amine moiety is the desired group of variation the strategy outlined in Scheme 1 is of particular interest. In contrary, the strategy depicted in Scheme 2 allows the phenol part of the structure to be varied in a rapid and parallel fashion. As described under Scheme 1, compounds of formula IA can be further converted into structures IB applying the methods outlined before.

Scheme 3

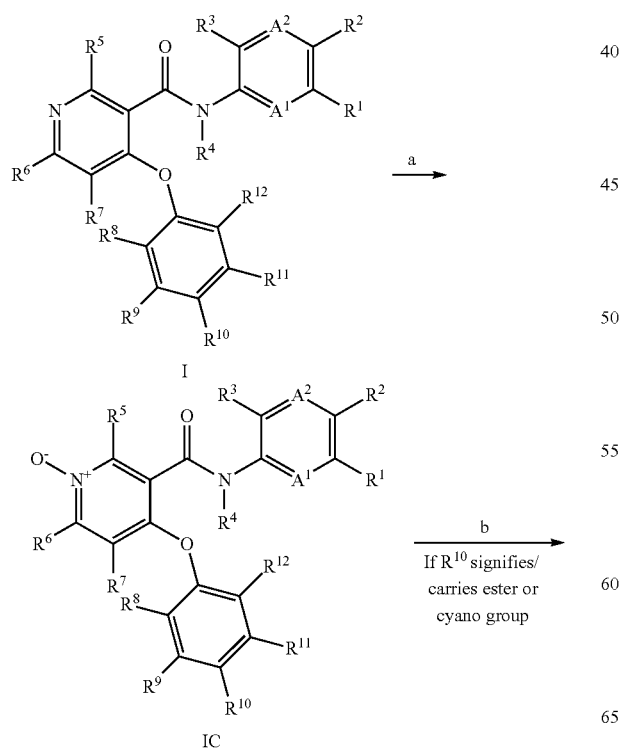

-continued

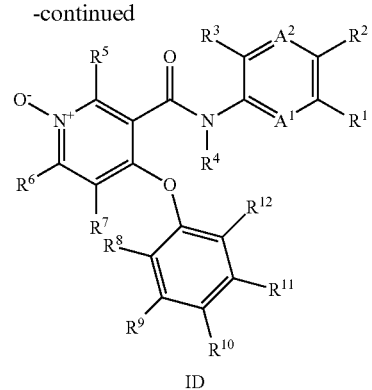

ID

R[10] signifies/carries
carboxylic acid or
tetrazole group

Compounds of the general structure IC and ID in which B[2] signifies CR[7] can be prepared according to Schemes 3 and 4. The synthesis of pyridine N-oxides via oxidation of the corresponding pyridines is widely described in literature and can be accomplished by a variety of methods. For example, by using aqueous solutions of hydrogen peroxide in acetic acid or using dimethyl dioxirane or meta-chloroperbenzoic acid in an appropriate solvent such as, e.g. dichloromethane.

In those cases where compounds I contain other functional groups that are reactive or can be oxidized under the applied reaction conditions it can be advantageous to perform the oxidation of the nicotinic acid intermediates 1 as a the first synthetic step (Scheme 4, step a) with subsequent amide coupling of the resulting N-oxide intermediates 6 with aryl- or heteroaryl-amines 4 (step b) and reacting the resulting intermediates 7 with phenols 2 under the conditions outlined before to furnish compounds IC. Compounds of formula IC can be further converted into structures ID applying the methods described above.

Scheme 4

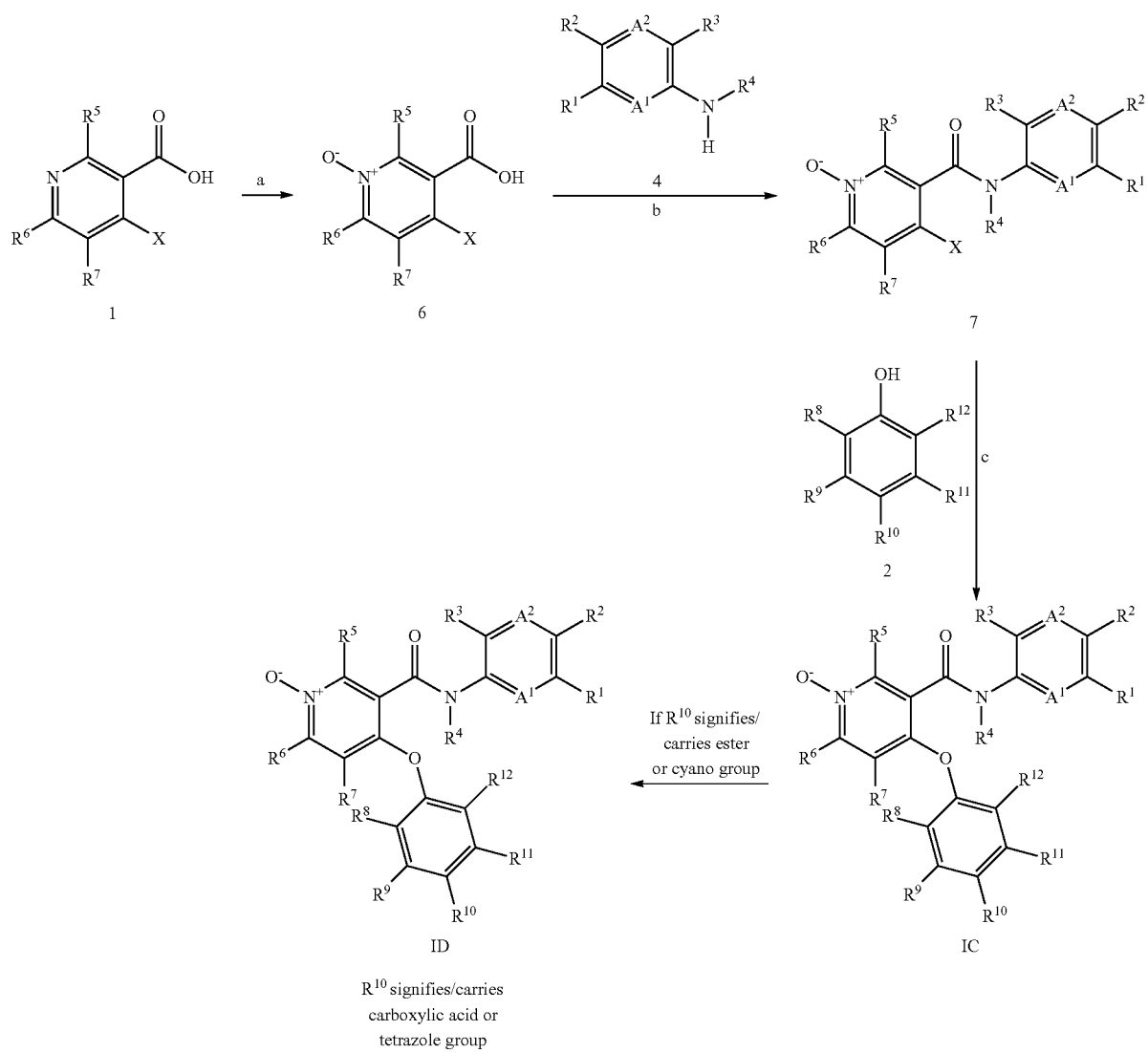

If desired or required, functional groups present in I (such as —CO₂alkyl, amino groups, cyano groups and others) may be derivatized to other functional groups using typical standard procedures known to those skilled in the art (e.g. reduction of —CO₂alkyl to —CH₂OH with LiAlH₄, hydrolysis of —CO₂alkyl to CO₂H and subsequent optional conversion to an amide, acylation of amino groups and the like).

As described herein before, the compounds of formula I of the present invention can be used as medicaments for the treatment of diseases which are associated with the modulation of GPBAR1 activity.

As compounds of formula I of the invention are agonists of the GPBAR1 receptor, the compounds will be useful for lowering glucose, lipids, and insulin resistance in diabetic patients and in non-diabetic patients who have impaired glucose tolerance or who are in a pre-diabetic condition. The compounds of formula I are further useful to ameliorate hyperinsulinemia, which often occurs in diabetic or pre-diabetic patients, by modulating the swings in the level of serum glucose that often occurs in these patients. The compounds of formula I are also useful in reducing the risks associated with metabolic syndrome, in reducing the risk of developing atherosclerosis or delaying the onset of atherosclerosis, and reducing the risk of angina, claudication, heart attack, stroke, and coronary artery disease. By keeping hyperglycemia under control, the compounds are useful to delay or for preventing vascular restenosis and diabetic retinopathy.

The compounds of formula I of the present invention are useful in improving or restoring β-cell function, so that they may be useful in treating type 1 diabetes or in delaying or preventing a patient with type 2 diabetes from needing insulin therapy. The compounds may be useful for reducing appetite and body weight in obese subjects and may therefore be useful in reducing the risk of co-morbidities associated with obesity such as hypertension, atherosclerosis, diabetes, and dyslipidemia. By elevating the levels of active GLP-1 in vivo, the compounds are useful in treating neurological disorders such as Alzheimer's disease, multiple sclerosis, and schizophrenia.

Thus, the expression "diseases which are associated with the modulation of GPBAR1 activity" means diseases such as metabolic, cardiovascular, and inflammatory diseases, for example diabetes, particularly type 2 diabetes or gestational diabetes, impaired fasting glucose, impaired glucose tolerance, insulin resistance, hyperglycemia, obesity, metabolic syndrome, ischemia, myocardial infarction, retinopathy, vascular restenosis, hypercholesterolemia, hypertriglyceridemia, dyslipidemia or hyperlipidemia, lipid disorders such as low HDL cholesterol or high LDL cholesterol, high blood pressure, angina pectoris, coronary artery disease, atherosclerosis, cardiac hypertrophy, rheumatoid arthritis, asthma, chronic obstructive pulmonary disease (COPD), psoriasis, ulcerative colitis, Crohn's disease, disorders associated with parenteral nutrition especially during small bowel syndrome, irritable bowl syndrome (IBS), allergy diseases, fatty liver, non-alcoholic fatty liver disease (NAFLD), liver fibrosis, non-alcoholic steatohepatitis (NASH), primary sclerosing cholangitis (PSC), liver cirrhosis, primary biliary cirrhosis (PBC), kidney fibrosis, anorexia nervosa, bulimia nervosa and neurological disorders such as Alzheimer's disease, multiple sclerosis, schizophrenia and impaired cognition.

In a preferable aspect, the expression 'diseases which are associated with the modulation of GPBAR1 activity' relates to diabetes, particularly type II diabetes, impaired fasting glucose, impaired glucose tolerance, hyperglycemia, metabolic syndrome, obesity, hypercholesterolemia and dyslipidemia.

The invention also relates to pharmaceutical compositions comprising a compound as defined above and a pharmaceutically acceptable carrier and/or adjuvant. More specifically, the invention relates to pharmaceutical compositions useful for the treatment of diseases which are associated with the modulation of GPBAR1 activity.

Further, the invention relates to compounds of formula I as defined above for use as therapeutically active substances, particularly as therapeutically active substances for the treatment of diseases which are associated with the modulation of GPBAR1 activity. Especially preferred are compounds of formula I for use in diabetes, preferably type II diabetes, or hyperglycemia.

In another aspect, the invention relates to a method for the treatment a of diseases which are associated with the modulation of GPBAR1 activity, which method comprises administering a therapeutically active amount of a compound of formula I to a human being or animal. A method for the treatment of diabetes, preferably type II diabetes, or hyperglycemia is preferred.

The invention further relates to the use of compounds of formula I as defined above for the treatment of diseases which are associated with the modulation of GPBAR1 activity.

In addition, the invention relates to the use of compounds of formula I as defined above for the preparation of medicaments for the treatment of diseases which are associated with the modulation of GPBAR1 activity. The use of compounds of formula I as defined above for the preparation of medicaments for the treatment of diabetes, preferably type II diabetes, or hyperglycemia is especially preferred.

Also contemplated herein is a combination therapy using one or more compounds of formula I or compositions of the present invention, or a pharmaceutically acceptable salts thereof, in combination with one or more other pharmaceutically active compounds independently selected from the group consisting of the following:

(a) human peroxisome proliferator activated receptor (PPAR) gamma agonists (e.g., thiazolidinediones and glitazones, e.g., rosiglitazone, troglitazone, pioglitazone, englitazone, balaglitazone, and netoglitazone),
(b) biguanides such as metformin, metformin hydrochloride, buformin and phenformin,
(c) dipeptidyl peptidase IV (DPP-4) inhibitors, such as sitagliptin, sitagliptin phosphate, saxagliptin, vildagliptin, alogliptin, carmegliptin, denagliptin sitagliptin, saxagliptin, and SYR-322,
(d) incretins such as glucagon-like peptide-1 (GLP-1) receptor agonists (e.g., Exenatide (Byetta™), NN2211 (Liraglutide), GLP-1(7-36) amide and its analogs, GLP-1(7-37) and its analogs, AVE-0010 (ZP-10), R1583 (taspoglutide), GSK-716155 (albiglutide, GSK/Human Genome Sciences), BRX-0585 (Pfizer/Biorexis) and CJC-1134-PC (Exendin-4:PC-DAC™) or glucose-dependent insulinotropic peptide (GIP),
(e) insulin or insulin analogs such as LysPro insulin or inhaled formulations comprising insulin,
(f) sulfonylureas such as tolazamide, chlorpropamide, glipizide, glimepiride, glyburide, glibenclamide, tolbutamide, acetohexamide or glypizide,
(g) α-glucosidase inhibitors such as miglitol, acarbose, epalrestat, or voglibose,
(h) cholesterol biosynthesis inhibitors such as HMG CoA reductase inhibitors, e.g., lovastatin, simvastatin, pravastatin, fluvastatin, atorvastatin, cerivastatin, itavastin, nisvastatin and rivastatin, or squalene epoxidase inhibitors, e.g., terbinafine,
(i) plasma HDL-raising agents such as CETP inhibitors e.g., anacetrapib, torcetrapib and dalcetrapib, or PPAR alpha agonists, e.g., gemfibronzil, clofibrate, fenofibrate and bezafibrate,
(j) PPAR dual alpha/gamma agonists such as muraglitazar, naveglitazar, aleglitazar, tesaglitazar, peliglitazar, farglitazar and JT-501,
(k) bile acid sequestrants, e.g., anion exchange resins, or quaternary amines (e.g., cholestyramine or colestipol)), or ileal bile acid transporter inhibitors (BATi);
(l) nicotinyl alcohol, nicotinic acid, niacinamide or salts thereof,
(m) cholesterol absorption inhibitors such as ezetimibe or acyl-Coenzyme A:cholesterol O-acyl transferase (ACAT) inhibitors such as avasimibe,
(n) selective estrogen receptor modulators such as raloxifene or tamoxifen) or LXR alpha or beta agonists, antagonists or partial agonists (e.g., 22(R)-hydroxycholesterol, 24(S)-hydroxycholesterol, T0901317 or GW3965);
(o) microsomal triglyceride transfer protein (MTP) inhibitors, alpha2-antagonists and imidazolines (e.g., midaglizole, isaglidole, deriglidole, idazoxan, efaroxan, fluparoxan),
(p) insulin secretagogues such as linogliride, nateglinide, repaglinide, mitiglinide calcium hydrate or meglitinide);
(q) SGLT-2 inhibitors (e.g., dapagliflozin, sergliflozin and AVE 2268),
(s) glucokinase activators such as the compounds disclosed in e.g., WO 00/58293 A1;
(t) protein tyrosine phosphatase-1B (PTP-1B) inhibitors,
(u) glucagon receptor antagonists,
(v) anti-obesity agents such as fenfluramine, dexfenfluramine, phentiramine, sibutramine, orlistat, neuropeptide Y1 or Y5 antagonists, neuropeptide Y2 agonists, MC4R (melanocortin 4 receptor) agonists, cannabinoid receptor 1 (CB-1) antagonists/inverse agonists, and B3 adrenergic receptor agonists (e.g., GW-320659), nerve growth factor agonist (e.g., axokine), growth hormone agonists (e.g., AOD-9604), 5-HT (serotonin) reuptake/transporter inhibitors (e.g., Prozac), DA (dopamine) reuptake inhibitors (e.g., Buprorion), 5-HT, NA and DA reuptake blockers, steroidal plant extracts (e.g., P57), CCK-A (cholecystokinin-A) agonists, GHSR1a (growth hormone secretagogue receptor) antagonist/inverse agonists, ghrelin antibody, MCH1R (melanin concentrating hormone 1R) antagonists (e.g., SNAP 7941), MCH2R (melanin concentrating hormone 2R) agonist/antagonists, H3 (histamine receptor 3) inverse agonists or antagonists, H1 (histamine 1 receptor) agonists, FAS (Fatty acid synthase) inhibitors, ACC-2 (acetyl-CoA carboxylase-1) inhibitors, DGAT-2 (diacylglycerol acyltransferase 2) inhibitors, DGAT-1 (diacylglycerol acyltransferase 1) inhibitors, CRF (corticotropin releasing factor) agonists, Galanin antagonists, UCP-1 (uncoupling protein-1), 2 or 3 activators, leptin or a leptin derivatives, opioid antagonists, orexin antagonists, BRS3 agonists, GLP-1 (glucagons-like peptide-1) agonists, IL-6 agonists, a-MSH agonists, AgRP antagonists, BRS3 (bombesin receptor subtype 3) agonists, 5-HT1B agonists, POMC antagonists, CNTF (ciliary neurotrophic factor or CNTF derivative), NN2211, Topiramate, glucocorticoid antagonist, Exendin-4 agonists, 5-HT$_{2C}$ (serotonin receptor 2C) agonists (e.g., Lorcaserin), PDE (phosphodiesterase) inhibitors, fatty acid transporter inhibitors, dicarboxylate transporter inhibitors, glucose transporter inhibitors, (w) anti-inflammatory agents such as cyclooxygenase-2 (COX-2) inhibitors (e.g., rofecoxib and celecoxib); glucocorticoids, azulfidine, thrombin inhibitors (e.g., heparin, argatroban, melagatran, dabigatran), platelet aggregation inhibitors (e.g., glycoprotein IIb/IIIa fibrinogen receptor antagonists or aspirin), and ursodeoxycholic acid (UDCA) and norursodeoxycholic acid (norUDCA), and (y) antihypertensives such as beta blockers (e.g., angiotensin II receptor antagonists such as losartan, eprosartan, irbesartan, tasosartan, telmisartan or valsartan; angiotensin converting enzyme inhibitors such as enalapril, captopril, cilazapril, ramapril, zofenopril, lisinopril and fosinopril; calcium channel blockers such as nifedipine and diltiazem and endothelian antagonists.

Such other pharmaceutically active compounds may be administered in an amount commonly used therefore, contemporaneously or sequentially with a compound of the formula I or a pharmaceutically acceptable salt thereof. In the treatment of patients who have type 2 diabetes, insulin resistance, obesity, metabolic syndrome, neurological disorders, and co-morbidities that accompany these diseases, more than one pharmaceutically active compound is commonly administered. The compounds of formula I of this invention may generally be administered to a patient who is already taking one or more other drugs for these conditions. When a compound of formula I is used contemporaneously with one or more other pharmaceutically active compounds, a pharmaceutical composition in an unit dosage form containing such other pharmaceutically active compounds and the compound of the formula I is preferred. Thus, the invention also relates to a pharmaceutical composition containing a compound of formula I in combination with one or more other pharmaceutically active compounds as defined above. When used in combination with one or more other active ingredients, the compound of formula I of the present invention and the other pharmaceutically active compounds may be used in lower doses than when each is used singly. These kinds of pharmaceutical compositions are also included in the invention.

However, the combination therapy also includes therapies in which the compound of formula I and one or more other pharmaceutically active compounds are administered in different dosage forms, but with overlapping schedules. The invention thus also relates to a method for the treatment a of diseases which are associated with the modulation of GPBAR1 activity, which method comprises administering a therapeutically active amount of a compound of formula I in combination with one or more other pharmaceutically active compounds to a human being or animal.

The following test was carried out in order to determine the activity of the compounds of formula I:

The cDNA of the human GPBAR1 receptor (Genbank: NM_170699 with the exception of a silent C:G mutation at position 339 from the start codon) was amplified by polymerase chain reaction (PCR) from human cDNA and inserted into pCineo (Promega) by standard methods (Current Protocols in Molecular Biology, Wiley Press, ed. Ausubel et al.). The final clone was verified by DNA sequence analysis. The plasmid was transfected into CHO cells deficient in dihydrofolate reductase activity (CHO-dhfr–) using Lipofectamine plus (Invitrogen). Clones were isolated in limited dilution conditions and identified by activities in the cAMP assay using lithocholic acid as agonist. A clonal cell line displaying the greatest activity in cAMP increases was selected and identified as giving consistently good responses for up to at least 20 passages.

cAMP Assay

CHO-dhfr(minus) cells expressing human GPBAR1 receptors are seeded 17-24 hours prior to the experiment 50.000 cells per well in a black 96 well plate with flat clear bottom (Corning Costar #3904) in DMEM (Invitrogen No. 31331), 1×HT supplement, with 10% fetal calf serum and incubated at 5% $CO_2$ and 37° C. in a humidified incubator. The growth medium was exchanged with Krebs Ringer Bicarbonate buffer with 1 mM IBMX and incubated at 30° C. for 30 min. Compounds were added to a final assay volume of 100 µl and incubated for 30 min at 30° C. The assay was stopped by the addition of 50 µA lysis reagent (Tris, NaCl, 1.5% Triton X100, 2.5% NP40, 10% $NaN_3$) and 50 µl detection solutions (20 µM mAb Alexa700-cAMP 1:1, and 48 µM Ruthenium-2-AHA-cAMP) and shaked for 2 h at room temperature. The time-resolved energy transfer is measured by a TRF reader (Evotec Technologies GmbH, Hamburg Germany), equipped with a ND:YAG laser as excitation source. The plate is measured twice with the excitation at 355 nm and at the emission with a delay of 100 ns and a gate of 100 ns, total exposure time 10 s at 730 (bandwith 30 nm) or 645 nm (bandwith 75 nm), respectively. The measured signal at 730 nm has to be corrected for the ruthenium background, the direct excitation of Alexa and the buffer control. The FRET signal is calculated as follows: FRET=T730-Alexa730-P (T645-B645) with P=Ru730-B730/Ru645-B645, where T730 is the test well measured at 730 nM, T645 is the test well measured at 645 nm, B730 and B645 are the buffer controls at 730 nm and 645 nm, respectively. cAMP content is determined from the function of a standard curve spanning from 10 µM to 0.13 nM cAMP.

$EC_{50}$ values were determined using Activity Base analysis (ID Business Solution, Limited). The $EC_{50}$ values for a wide range of bile acids generated from this assay were in agreement with the values published in the scientific literature. Specificity for GPBAR1 was tested in non-transfected CHO cells in the same assay as above.

The compounds according to formula I have an activity in the above assay ($EC_{50}$) preferably of 0.5 nM to 10 µM, more preferably of 0.5 nM to 1 µM and most preferably of 0.5 nM to 100 nM.

For example, the following compounds showed the following human $EC_{50}$ values in the functional cAMP assay described above:

| Example | human $EC_{50}$ [µM] |
| --- | --- |
| 1 | 0.04 |
| 2 | 0.1 |
| 3 | 0.1 |
| 4 | 0.003 |
| 5 | 1.8 |
| 6 | 0.003 |
| 7 | 0.3 |
| 8 | 0.002 |
| 9 | 0.05 |
| 10 | 0.7 |
| 11 | 0.01 |
| 12 | 0.1 |
| 13 | 0.2 |
| 14 | 0.1 |
| 15 | 0.1 |
| 16 | 0.04 |
| 17 | 1.9 |
| 18 | 1.4 |
| 19 | 0.1 |
| 20 | 0.4 |
| 21 | 0.4 |

-continued

| Example | human $EC_{50}$ [µM] |
|---|---|
| 22 | 0.9 |
| 23 | 0.2 |
| 24 | 0.1 |
| 25 | 1.7 |
| 26 | 0.004 |
| 27 | 0.004 |
| 28 | 0.004 |
| 29 | 0.1 |
| 30 | 0.4 |
| 31 | 0.1 |
| 32 | 0.9 |
| 33 | 0.02 |
| 34 | 0.3 |
| 35 | 0.1 |
| 36 | 0.3 |
| 37 | 0.9 |
| 38 | 0.04 |
| 39 | 0.4 |
| 40 | 0.2 |
| 41 | 0.1 |
| 42 | 0.1 |
| 43 | 0.1 |
| 44 | 0.02 |
| 45 | 0.6 |
| 46 | 0.03 |
| 47 | 0.1 |
| 48 | 0.2 |
| 49 | 0.04 |
| 50 | 1.1 |
| 51 | 0.3 |
| 52 | 0.01 |
| 53 | 0.1 |
| 54 | 0.3 |
| 55 | 0.003 |
| 56 | 0.003 |
| 57 | 0.01 |
| 58 | 0.03 |
| 59 | 0.5 |
| 60 | 0.2 |
| 61 | 0.4 |
| 62 | 0.012 |
| 63 | 0.001 |
| 64 | 0.02 |
| 65 | 0.02 |
| 66 | 0.3 |
| 67 | 0.02 |
| 68 | 0.2 |
| 69 | 0.04 |
| 70 | 0.4 |
| 71 | 0.1 |
| 72 | 0.4 |
| 73 | 0.05 |
| 74 | 0.022 |
| 75 | 0.01 |
| 76 | 0.04 |
| 77 | 0.4 |
| 78 | 0.3 |
| 79 | 0.01 |
| 80 | 0.09 |

The compounds of formula I and their pharmaceutically acceptable salts can be used as medicaments, e.g., in the form of pharmaceutical preparations for enteral, parenteral or topical administration. They can be administered, for example, perorally, e.g., in the form of tablets, coated tablets, dragées, hard and soft gelatin capsules, solutions, emulsions or suspensions, rectally, e.g., in the form of suppositories, parenterally, e.g., in the form of injection solutions or suspensions or infusion solutions, or topically, e.g., in the form of ointments, creams or oils. Oral administration is preferred.

The production of the pharmaceutical preparations can be effected in a manner which will be familiar to any person skilled in the art by bringing the described compounds of formula I and their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatin capsules. Suitable carrier materials for soft gelatin capsules are, for example, vegetable oils, waxes, fats and semi-solid and liquid polyols (depending on the nature of the active ingredient no carriers might, however, be required in the case of soft gelatin capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavor-improving agents, salts for varying the osmotic pressure, buffer substances, solubilizers, colorants and masking agents and anti-oxidants come into consideration as pharmaceutical adjuvants.

The dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 to 1000 mg, especially about 1 to 300 mg, comes into consideration. Depending on severity of the disease and the precise pharmacokinetic profile the compound could be administered with one or several daily dosage units, e.g., in 1 to 3 dosage units.

The pharmaceutical preparations conveniently contain about 1-500 mg, preferably 1-100 mg, of a compound of formula I.

The following examples serve to illustrate the present invention in more detail. They are, however, not intended to limit its scope in any manner.

EXAMPLES

Abbreviations:

CAS RN=chemical abstracts registration number, DMAc=dimethylacetamide, DMAP=4-dimethylaminopyridine, DMF=N,N-dimethylformamide, DMSO=dimethyl sulfoxide, EI=electron impact, ESI=electrospray ionization, h=hour, HATU=1-[bis(dimethylamino)methylene]-1H-1,2,3-triazolo[4,5-b]pyridinium-3-oxide hexafluorophosphate, HCl=hydrogen chloride, HPLC=high performance liquid chromatography, ISP=ion spray positive (mode), ISN=ion spray negative (mode), min=minutes, LiOH=lithium hydroxide, $MgSO_4$=magnesium sulfate, MPLC=medium performance liquid chromatography, MS=mass spectrum, $NaHCO_3$=sodium hydrogen carbonate, NaOH=sodium hydroxide, $Na_2SO_4$=sodium sulfate, $NH_4Cl$=ammonium chloride, NMR=nuclear magnetic resonance, KOH=potassium hydroxide, P=protecting group, R=any group, rt=room temperature, $SiO_2$=silica gel, THF=tetrahydrofuran, X=halogen.

Example 1

[4-(2,5-Dichloro-phenoxy)-pyridin-3-yl]-(3,4-dihydro-2H-quinolin-1-yl)-methanone

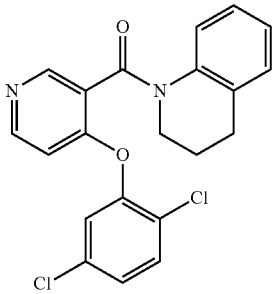 [SMILES: O=C(c1cnccc1Oc1cc(Cl)ccc1Cl)N1CCCc2ccccc21]

To a solution of 0.16 g (0.56 mmol) 4-(2,5-dichloro-phenoxy)-nicotinic acid in 3 mL N,N-dimethylformamide were added 0.225 g (0.59 mmol) O-(7-azabenzotriazol-1-yl)-N,N,N',N'-tetramethyluronium hexafluorophosphate (HATU, commercially available, CAS RN 148893-10-1) and 0.29 mL (1.69 mmol) N,N-diisopropylethylamine. To the light yellow solution 0.07 mL (0.59 mmol) 1,2,3,4-tetrahydroquinoline (commercially available; CAS RN 635-46-1) was added and the resulting light yellow solution was stirred at room temperature for 23 hours. The reaction mixture was poured on water and extracted three times with ethyl acetate. The combined organic layers were washed with water and brine, dried over magnesium sulfate, filtered, treated with silica gel and evaporated. The resulting powder was purified by silica gel chromatography using a MPLC system (20 g silica gel column, CombiFlash Companion, Isco Inc.) eluting with a gradient of n-heptane:ethyl acetate (100:0 to 50:50). The product-containing fractions were combined and evaporated to give 165 mg (73%) of the desired compound as a light brown solid. MS (ESI): m/z=399.06 [M+H]$^+$.

Intermediate 4-(2,5-Dichloro-phenoxy)-nicotinic acid

To a suspension of 10 g (63.47 mmol) 4-chloronicotinic acid (commercially available; CAS RN 10177-29-4) and 11.38 g (69.81 mmol) 2,5-dichlorophenol (commercially available CAS RN 583-78-8) in 50 mL dry N,N-dimethylformamide were added 17.55 g (126.94 mmol) potassium carbonate, 1.21 g (6.35 mmol) copper(I)iodide and 1.21 g (19.04 mmol) copper nanopowder. The green suspension was stirred at 120° C. (oil bath temperature) for 3 hours and then cooled down to 80° C. At that temperature, 400 mL water were added, the suspension was stirred at 80° C. for 5 min., filtered over Dicalite® speed plus (Acros) and the filter cake washed twice with 50 mL water. The resulting filtrate was extracted three times with ethyl acetate and then the pH was adjusted to 4-5 using 140 mL 1M aqueous hydrochloric acid. The resulting green, turbid solution was treated with ethyl acetate, stirred for 5 min. and filtered. The blue solid that had formed was filtered off and the layers of the filtrate were separated. The aqueous layer was saturated with solid sodium chloride and extracted three times with ethyl acetate. The combined organic layers were washed with brine, dried over magnesium sulfate, filtered and evaporated. To the resulting solid 200 mL saturated aqueous potassium carbonate solution and 200 mL ethyl acetate were added. The aqueous layer was extracted twice with 200 mL ethyl acetate and the pH was adjusted to 4 using 25% aqueous hydrochloric acid. The resulting suspension was extracted three times with ethyl acetate. The combined organic layers were washed three times with water and once with brine, dried over magnesium sulfate, filtered and evaporated to give the desired compound as a light brown solid (7.29 g, 40%). MS (ESI): m/z=281.8 [M−H]$^−$.

Example 2

[4-(2,5-Dichloro-phenoxy)-pyridin-3-yl]-(6,7-difluoro-3,4-dihydro-2H-quinolin-1-yl)-methanone

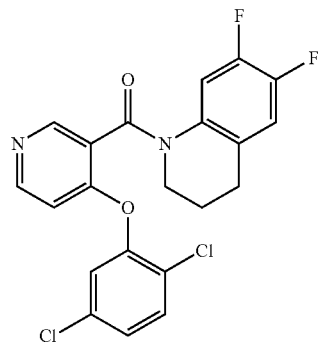 [SMILES: O=C(c1cnccc1Oc1cc(Cl)ccc1Cl)N1CCCc2cc(F)c(F)cc21]

The title compound was prepared in analogy to Example 1, from 6,7-difluoro-1,2,3,4-tetrahydro-quinoline (commercially available; CAS RN 953717-64-1) and 4-(2,5-dichloro-phenoxy)-nicotinic acid (Example 1, intermediate). Light brown gum (28%). MS (ESI): m/z=435.04 [M+H]$^+$.

Example 3

[4-(2,5-Dichloro-phenoxy)-pyridin-3-yl]-(3,4-dihydro-2H-quinoxalin-1-yl)-methanone

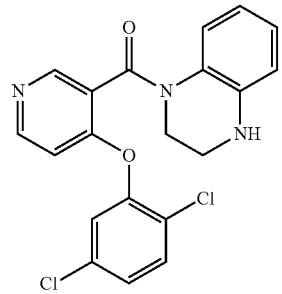 [SMILES: O=C(c1cnccc1Oc1cc(Cl)ccc1Cl)N1CCNc2ccccc21]

The title compound was prepared in analogy to Example 1, from 1,2,3,4-tetrahydro-quinoxaline (commercially available; CAS RN 3476-89-9) and 4-(2,5-dichloro-phenoxy)-nicotinic acid (Example 1, intermediate). Light yellow foam (99%). MS (ESI): m/z=400.06 [M+H]$^+$.

Example 4

[4-(2,5-Dichloro-phenoxy)-pyridin-3-yl]-(4-methyl-3,4-dihydro-2H-quinoxalin-1-yl)-methanone

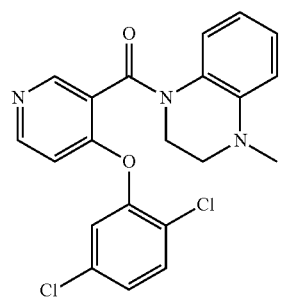 [SMILES: CN1CCN(C(=O)c2cnccc2Oc2cc(Cl)ccc2Cl)c2ccccc21]

A solution of 0.12 g (0.30 mmol) [4-(2,5-dichloro-phenoxy)-pyridin-3-yl]-(3,4-dihydro-2H-quinoxalin-1-yl)-methanone (Example 3) in 1 mL N,N-dimethylformamide was treated with 0.014 g (0.32 mmol) sodium hydride (60% suspension in mineral oil) upon which gas evolution set in and a colour change occurred. After stirring for 30 min., 0.022 mL (0.36 mmol) iodomethane were added. After stirring for 7 hours at room temperature, the reaction mixture was poured onto water and was extracted three times with ethyl acetate. The combined organic layers were washed with water and brine, dried over magnesium sulfate, filtered, treated with silica gel and evaporated to dryness. The resulting powder was purified by silica gel chromatography using a MPLC system (20 g silica gel column, CombiFlash Companion, Isco Inc.) eluting with a gradient of n-heptane:ethyl acetate (100:0 to 50:50) to give the desired compound as an orange solid (32 mg, 26%). MS (ESI): m/z=414.077 [M+H]+.

Example 5

2-{4-[4-(2,5-Dichloro-phenoxy)-pyridine-3-carbonyl]-3,4-dihydro-2H-quinoxalin-1-ylmethyl}-cyclopropanecarboxylic acid ethyl ester

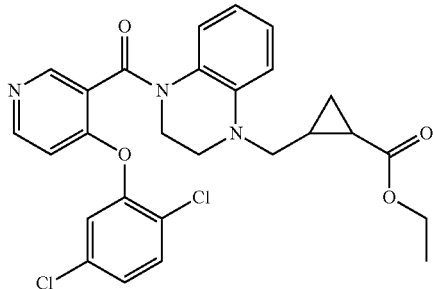 [SMILES: CCOC(=O)C1CC1CN1CCN(C(=O)c2cnccc2Oc2cc(Cl)ccc2Cl)c2ccccc21]

To a solution of 0.10 g (0.25 mmol) [4-(2,5-dichloro-phenoxy)-pyridin-3-yl]-(3,4-dihydro-2H-quinoxalin-1-yl)-methanone (Example 3) were added 0.036 g (0.25 mmol) ethyl 2-formyl-1-cyclopropane-carboxylate (commercially available, CAS RN 20417-61-2), 0.008 g (0.026 mmol) dibutyltin dichloride and 0.06 mL (0.50 mmol) phenylsilane. The resulting solution was heated for 10 min. in a microwave oven at 150° C. The light yellow solution was evaporated and dissolved in acetonitrile containing a few drops of N,N-dimethylformamide. The suspension was filtered using a syringe micro filter and purified on a preparative HPLC system (Phenomenex Gemini column) using a gradient of acetonitrile:water (containing 0.05% formic acid) (10:90 to 98:2) to give 60 mg (46%) of the desired compound as a light brown foam. MS (ESI): m/z=526.13 [M+H]+.

Example 6

(4-Cyclopropylmethyl-3,4-dihydro-2H-quinoxalin-1-yl)-[4-(2,5-dichloro-phenoxy)-pyridin-3-yl]-methanone

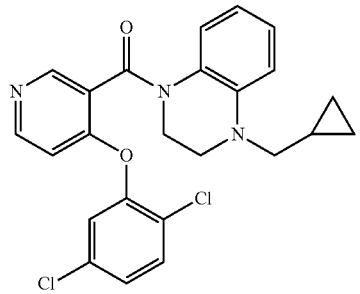 [SMILES: O=C(c1cnccc1Oc1cc(Cl)ccc1Cl)N1CCN(CC2CC2)c2ccccc21]

The title compound was prepared in analogy to Example 5, from [4-(2,5-dichloro-phenoxy)-pyridin-3-yl]-(3,4-dihydro-2H-quinoxalin-1-yl)-methanone (Example 3), cyclopropanecarboxaldehyde (commercially available; CAS RN 1489-69-6), dibutyltin dichloride and phenylsilane. Light brown solid (53%). MS (ESI): m/z=454.109 [M+H]+.

Example 7

[4-(2,5-Dichloro-phenoxy)-pyridin-3-yl]-(4-methanesulfonyl-3,4-dihydro-2H-quinoxalin-1-yl)-methanone

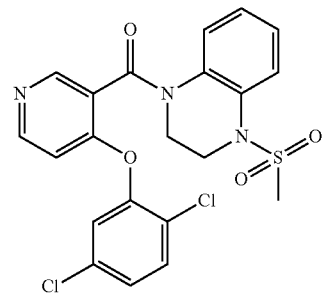 [SMILES: CS(=O)(=O)N1CCN(C(=O)c2cnccc2Oc2cc(Cl)ccc2Cl)c2ccccc21]

To a solution of 0.10 g (0.25 mmol) [4-(2,5-dichloro-phenoxy)-pyridin-3-yl]-(3,4-dihydro-2H-quinoxalin-1-yl)-methanone (Example 3) in 2 mL dichloromethane were added 0.08 mL (0.50 mmol) N,N-diisopropylethylamine followed by dropwise addition of 0.02 mL (0.27 mmol) methanesulfonylchloride. After 16 hours another 0.08 mL (0.50 mmol) N,N-diisopropylethylamine and 0.02 mL (0.27 mmol) methanesulfonylchloride were added. The reaction mixture was poured on water and was extracted three times with dichloromethane. The combined organic layers were washed with brine, dried over magnesium sulfate, filtered, treated with silica gel and evaporated. The resulting powder was purified by silica gel chromatography using a MPLC system (10 g silical gel column, CombiFlash Companion, Isco Inc.) eluting with a gradient of n-heptane:ethyl acetate (100:0 to 50:50) followed by a second chromatography on a 10 g silica gel column using a gradient from n-heptane:tert-butyl methyl ether (100:0 to 25:75) to give 31 mg (26%) of the desired compound as a light brown foam. MS (ESI): m/z=478.039 [M+H]+.

Example 8

(4-Cyclopropyl-3,4-dihydro-2H-quinoxalin-1-yl)-[4-(2,5-dichloro-phenoxy)-pyridin-3-yl]-methanone

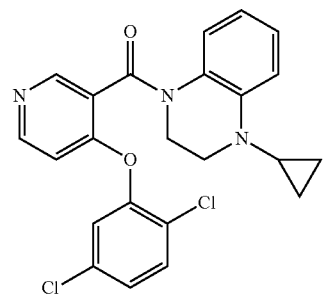 [SMILES: O=C(c1cnccc1Oc1cc(Cl)ccc1Cl)N1CCN(C2CC2)c2ccccc21]

The title compound was prepared in analogy to Example 1, from 4-(2,5-dichloro-phenoxy)-nicotinic acid (Example 1, intermediate) and 1-cyclopropyl-1,2,3,4-tetrahydro-quinoxaline. Light yellow foam (72%). MS (ESI): m/z=440.092 [M+H]⁺.

Intermediates a) 1-Cyclopropyl-1,2,3,4-tetrahydro-quinoxaline

To a stirred suspension of 1-cyclopropyl-1,4-dihydro-quinoxaline-2,3-dione (10.0 g, 49.45 mmol, 1.0 equiv) in tetrahydrofuran (500 mL) was added dropwise a 1 M solution of borane-tetrahydrofuran complex (108.8 mL, 108.8 mmol, 2.2 equiv; [CAS RN 14044-65-6]) and the reaction mixture stirred at room temperature over night. The solvent was removed by evaporation under reduced pressure and the crude reaction mixture extracted from a saturated aqueous solution of sodium bicarbonate (100 mL) with ethyl acetate (three times 100 mL). The combined organic phases were dried over sodium sulfate and purified by silica gel column chromatography using a MPLC system (CombiFlash Companion, Isco Inc.) eluting with a gradient of n-heptane:ethyl acetate to give 4.2 g (49%) of the title compound as a light yellow solid. MS (ISP): m/z=175.4 [M+H]⁺.

b) 1-Cyclopropyl-1,4-dihydro-quinoxaline-2,3-dione

To a solution of 1-cyclopropyl-4-hydroxy-1,4-dihydro-quinoxaline-2,3-dione (31.0 g, 0.14 mol, 1.0 equiv) in N,N-dimethylformamide (250 mL) was added triphenylphosphine (55.9 g, 0.21 mol, 1.5 equiv; [CAS RN 603-35-0]) and the reaction mixture stirred at 135° C. for 4 hours. The reaction mixture was cooled down to 0° C. and dichloromethane (400 mL) was added. The suspension was stirred for 30 min., filtered and washed with dichloromethane (200 mL) providing 23.8 g (83%) of the title compound as a white solid. MS (ISN): m/z=203.1 [M+H]⁺.

c) 1-Cyclopropyl-4-hydroxy-1,4-dihydro-quinoxaline-2,3-dione

To a solution of N-cyclopropyl-N-(2-nitro-phenyl)-oxalamic acid methyl ester (45.0 g, 0.17 mol, 1.0 equiv) in methanol (400 mL) was added palladium on carbon (4.52 g, 0.0043 mol, 0.025 equiv; 10% Pd/C; [CAS RN 7440-05-3]) and the reaction mixture stirred under an atmosphere of hydrogen (1.2 bar) at room temperature for 2 hours. The reaction mixture was diluted with ethyl acetate (400 mL), filtered over Celite® and the solvent mixture removed by evaporation under reduced pressure to give 31.2 g (84%) of the title compound as a light yellow solid. MS (ISN): m/z=219.1 [M+H]⁺.

d) N-Cyclopropyl-N-(2-nitro-phenyl)-oxalamic acid methyl ester

To a solution of cyclopropyl-(2-nitro-phenyl)-amine (32.0 g, 0.18 mol, 1.0 equiv) in dichloromethane (320 mL) was added triethylamine (18.2 g, 25.0 mL, 0.18 mol, 1.0 equiv; [CAS RN 121-44-8]) and methyl oxalyl chloride (22.0 g, 16.5 mL, 0.18 mol, 1.0 equiv; [CAS RN 5781-53-3]) slowly at 0° C. After the addition was completed the reaction mixture was stirred at room temperature for 72 h. The reaction mixture was extracted from a saturated aqueous sodium bicarbonate solution (300 mL) with dichloromethane (three times 200 mL) and the combined organic phases dried over magnesium sulfate. Purification by silica gel column chromatography using a MPLC Companion, Isco Inc.) eluting with a mixture of n-heptane:ethyl acetate (2:1) afforded 45.2 g (95%) of the title compound as a white solid. MS (ISP): m/z=265.1 [M+H]⁺.

e) Cyclopropyl-(2-nitro-phenyl)-amine

To cyclopropylamine (27.3 g, 33.1 mL, 0.48 mol, 2.25 equiv; [CAS RN 765-30-0]) was added dropwise 2-fluoronitrobenzene (30.0 g, 0.21 mol, 1.0 equiv; [CAS RN 1493-27-2]) over 1 hours at 30° C. and stirring of the reaction mixture continued at room temperature for 18 h. The reaction mixture was extracted from a saturated aqueous solution of sodium bicarbonate (500 mL) with ethyl acetate (three times 300 mL) and the combined organic phases were dried over magnesium sulfate. Purification by silica gel column chromatography using a MPLC system (CombiFlash Companion, Isco Inc.) eluting with a mixture of n-heptane:ethyl acetate (9:1) afforded 32.4 g (86%) of the title compound as a yellow oil. MS (ISP): m/z=178.0 [M+H]⁺.

Example 9

(6-Chloro-4-cyclopropyl-7-fluoro-3,4-dihydro-2H-quinoxalin-1-yl)-[4-(2,5-dichloro-phenoxy)-pyridin-3-yl]-methanone

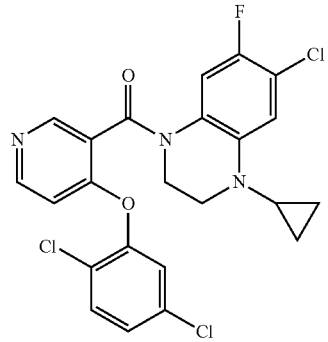 [SMILES: O=C(c1cnccc1Oc1cc(Cl)ccc1Cl)N1CCN(C2CC2)c2cc(Cl)c(F)cc21]

The title compound was prepared in analogy to Example 1, from 4-(2,5-dichloro-phenoxy)-nicotinic acid (Example 1, intermediate) and 7-chloro-1-cyclopropyl-6-fluoro-1,2,3,4-tetrahydro-quinoxaline and using a gradient of n-heptane: ethyl acetate (100:0 to 0:100) for the chromatographic purification. Light yellow solid (19%). MS (ESI): m/z=494.041 [M+H]⁺.

Intermediates a) 7-Chloro-1-cyclopropyl-6-fluoro-1,2,3,4-tetrahydro-quinoxaline

To a suspension of 390 mg (1.532 mmol) 7-chloro-1-cyclopropyl-6-fluoro-1,4-dihydro-quinoxaline-2,3-dione in 20 mL tetrahydrofuran was added 3.37 mL (3.369 mmol) 1M borane tetrahydrofuran complex. The reaction mixture was stirred for 6 hours at room temperature. The reaction mixture was poured on 30 mL 10% aqueous sodium bicarbonate solution and 30 mL ethyl acetate. The mixture was stirred for 30 min. at room temperature and the layers were separated. The aqueous layer was extracted a second time with 30 mL ethyl acetate. The organic layers were washed with 30 mL brine, dried over magnesium sulfate, filtered and concentrated under vacuum. The compound was purified by silica gel chromatography using a MPLC system (CombiFlash Companion, Isco Inc.) eluting with a gradient of n-heptane: ethyl acetate (100:0 to 40:60) to give 211 mg (61%) of the desired compound as a white solid. MS (ESI): m/z=225.0 [M+H]⁺.

b) 7-Chloro-1-cyclopropyl-6-fluoro-1,4-dihydro-quinoxaline-2,3-dione

To a solution of 685 mg (2.531 mmol) 6-chloro-4-cyclopropyl-7-fluoro-1-hydroxy-1,4-dihydro-quinoxaline-2,3-dione in 10 mL N,N-dimethylformamide was added 996 mg (3.796 mmol) triphenylphosphine. The reaction mixture was stirred for 4 hours at 135° C. The reaction mixture was concentrated under vacuum (15 mbar/55° C.). The residue was suspended in 20 mL dichloromethane. The suspension was stirred for 30 min at 0° C. and filtered and washed with 20 mL dichloromethane. White solid (63%). MS (ESI): m/z=255.034 [M+H]$^+$.

c) 6-Chloro-4-cyclopropyl-7-fluoro-1-hydroxy-1,4-dihydro-quinoxaline-2,3-dione To a solution of 1.2 g (3.789 mmol) N-(5-chloro-4-fluoro-2-nitro-phenyl)-N-cyclopropyl-oxalamic acid methyl ester in 15 mL MeOH was added 120 mg Pd(C) 10% on charcoal. The reaction mixture was stirred for 2 hours under hydrogen atmosphere at 1.2 bar at room temperature. 30 mL ethyl acetate was added and the reaction mixture was filtered over Dicalite® speed plus (Acros) speed plus (Acros) and concentrated under vacuum. Light yellow solid (68%). MS (ESI): m/z=269.014 [M+H]$^+$.

d) N-(5-Chloro-4-fluoro-2-nitro-phenyl)-N-cyclopropyl-oxalamic acid methyl ester To a solution of 1.0 g (4.336 mmol) (5-chloro-4-fluoro-2-nitro-phenyl)-cyclopropyl-amine (J. Med. Chem. 1992, 35(8), 1385) in 15 mL dichloromethane was added 439 mg (4.336 mmol) triethylamine and 531 mg (4.336 mmol) monomethyl oxalyl chloride at 0° C. The reaction mixture was stirred for 72 hours at room temperature. The reaction mixture was poured on 30 mL sodium bicarbonate 10% in water and 30 mL dichloromethane. The layers were separated. The aqueous layer was extracted a second time with 30 mL dichloromethane. The organic layers were washed with 30 mL brine, dried over magnesium sulfate, filtered and concentrated under vacuum. The residue was purified by silica gel chromatography using a MPLC system (CombiFlash Companion, Isco Inc.) eluting with a gradient of n-heptane:ethyl acetate (100:0 to 40:60) to give the compound as a light yellow solid (90%). MS (ESI): m/z=316.0 [M+H]$^+$.

Example 10

[4-(2,5-Dichloro-phenoxy)-1-oxy-pyridin-3-yl]-(3,4-dihydro-2H-quinolin-1-yl)-methanone

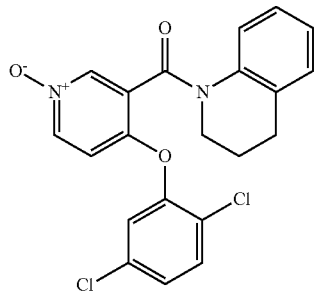 [SMILES: O=C(c1c[n+]([O-])ccc1Oc1cc(Cl)ccc1Cl)N1CCCc2ccccc21]

To an ice-cold solution of 0.27 g (0.68 mmol) [4-(2,5-dichloro-phenoxy)-pyridin-3-yl]-(3,4-dihydro-2H-quinolin-1-yl)-methanone (Example 1) in 3 mL dichloromethane was added 0.189 g (0.84 mmol) m-chloroperbenzoic acid (Aldrich, CAS RN 937-14-4). The light yellow solution was stirred at room temperature for 2.75 hours and then poured on a saturated aqueous sodium bicarbonate solution and extracted three times with dichloromethane. The combined organic layers were washed with brine, dried over magnesium sulfate, filtered, treated with silica gel and evaporated. The resulting powder was purified by silica gel chromatography using a MPLC system (CombiFlash Companion, Isco Inc.) eluting with a gradient of n-heptane:ethyl acetate:methanol (100:0:0 to 0:100:0 to 0:0:100) to give 279 mg (99%) of the desired compound as a light brown foam. MS (ESI): m/z=415.061 [M+H]$^+$.

Example 11

(6-Chloro-4-cyclopropyl-3,4-dihydro-2H-quinoxalin-1-yl)-[4-(2,5-dichloro-phenoxy)-pyridin-3-yl]-methanone

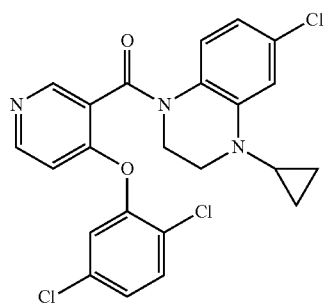 [SMILES: O=C(c1cnccc1Oc1cc(Cl)ccc1Cl)N1CCN(C2CC2)c2cc(Cl)ccc21]

To an ice-cold suspension of 0.61 g (1.39 mmol) (4-cyclopropyl-3,4-dihydro-2H-quinoxalin-1-yl)-[4-(2,5-dichloro-phenoxy)-pyridin-3-yl]-methanone (Example 8) in 3 mL dichloromethane were added 0.388 g (1.73 mmol) m-chloroperbenzoic acid (Aldrich, CAS RN 937-14-4). The cooling bath was removed, the reaction stirred at room temperature for 45 min., poured on a saturated solution of aqueous sodium bicarbonate and extracted three times with dichloromethane. The organic layers were washed with a saturated solution of aqueous sodium bicarbonate and brine, dried over magnesium sulfate, filtered, treated with silica gel and evaporated. The resulting powder was purified by silica gel chromatography using a MPLC system (20 g silica gel column, CombiFlash Companion, Isco Inc.) with a gradient of n-heptane:ethyl acetate:methanol (100:0:0 to 0:100:0 to 0:0:100). From the resulting light brown foam (0.51 g; MS (ESI): m/z=456.087 [M+H]$^+$), 0.20 g (0.44 mmol) were dissolved in 8 mL tetrahydrofuran and 0.09 mL (0.44 mmol) hexamethyldisilazane and 0.08 mL (1.1 mmol) methyl chloroformate were added. The resulting brown, turbid solution was stirred for 1.5 hours at room temperature, poured on saturated aqueous sodium bicarbonate solution and was extracted three times with ethyl acetate. The organic layers were washed with brine, dried over magnesium sulfate, filtered, treated with silica gel and evaporated. The resulting powder was purified by silica gel chromatography using a MPLC system (10 g silica gel column, CombiFlash Companion, Isco Inc.) eluting with a gradient of n-heptane:ethyl acetate (100:0 to 25:75). The resulting orange solid (0.13 g) was dissolved in acetonitrile and a few drops N,N-dimethylformamide, filtered using a syringe micro filter and purified two times on a preparative HPLC system (Phenomenex Gemini column) using a gradient of acetonitrile:water (containing 0.05% formic acid) (10:90 to 98:2) to give 65 mg (31%) of the title compound as a light brown foam. MS (ESI): m/z=474.054 [M+H]$^+$.

Example 12

4-(2,5-Dichloro-phenoxy)-N-(5-fluoro-2-methoxy-phenyl)-N-methyl-nicotinamide

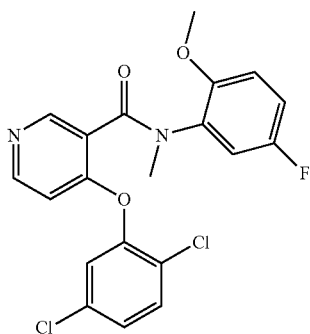 [SMILES: COc1ccc(F)cc1N(C)C(=O)c1cnccc1Oc1cc(Cl)ccc1Cl]

To an ice-cold suspension of 0.07 g (0.17 mmol) 4-(2,5-dichloro-phenoxy)-N-(5-fluoro-2-methoxy-phenyl)-nicotinamide in 1 mL tetrahydrofuran were added 0.019 g (0.17 mmol) potassium tert-butoxide followed by 10 µl (0.18 mmol) iodomethane. The suspension was stirred at room temperature for 16 hours, poured onto 10% aqueous citric acid solution and was extracted three times with ethyl acetate. The combined organic layers were washed with brine, dried over magnesium sulfate, filtered, treated with silica gel and evaporated to dryness. The resulting powder was purified by silica gel chromatography using a MPLC system (CombiFlash Companion, Isco Inc.) eluting with a gradient of n-heptane:ethyl acetate (100:0 to 50:50) to give 32 mg (44%) of the title compound as a white solid. MS (ESI): m/z=421.052 [M+H]$^+$.

Intermediate 4-(2,5-Dichloro-phenoxy)-N-(5-fluoro-2-methoxy-phenyl)-nicotinamide The title compound was prepared in analogy to Example 1, from 4-(2,5-dichloro-phenoxy)-nicotinic acid (Example 1, intermediate) and 5-fluoro-2-methoxy-phenylamine (commercially available; CAS RN 1978-39-8). White solid (74%). MS (ESI): m/z=407.036 [M+H]$^+$.

Example 13

4-(2,5-Dichloro-phenoxy)-N-methyl-N-o-tolyl-nicotinamide

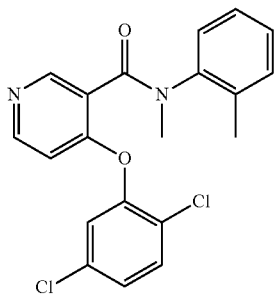 [SMILES: Cc1ccccc1N(C)C(=O)c1cnccc1Oc1cc(Cl)ccc1Cl]

The title compound was prepared in analogy to Example 1, from 4-(2,5-dichloro-phenoxy)-nicotinic acid (Example 1, intermediate) and N-methyl-o-toluidine (commercially available; CAS RN 611-21-2) and using a gradient of n-heptane: ethyl acetate (100:0 to 40:60). The compound was further purified through a second preparative HPLC chromatography (Phenomenex Gemini column) using a gradient of acetonitrile:water (containing 0.05% formic acid) (10:90 to 98:2). White solid (35%). MS (ESI): m/z=387.066 [M+H]$^+$.

Example 14

4-(2,5-Dichloro-phenoxy)-N-(2-methoxy-phenyl)-N-methyl-nicotinamide

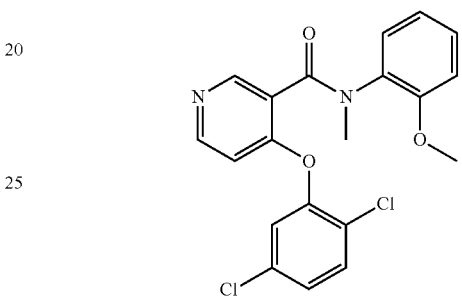

The title compound was prepared in analogy to Example 1, from 4-(2,5-dichloro-phenoxy)-nicotinic acid (Example 1, intermediate) and 2-methoxy-N-methylaniline (commercially available; CAS RN 10541-78-3) and using a gradient of n-heptane:ethyl acetate (100:0 to 40:60). The compound was further purified through a second preparative HPLC chromatography (Phenomenex Gemini column) using a gradient of acetonitrile:water (containing 0.05% formic acid) (50:50 to 95:5). White solid (57%). MS (ESI): m/z=403.062 [M+H]$^+$.

Example 15

4-(2,5-Dichloro-phenoxy)-N-(2-methoxy-pyridin-3-yl)-N-methyl-nicotinamide

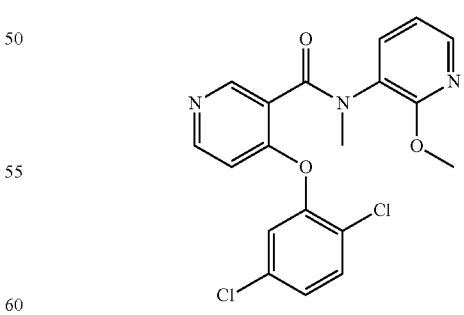

The title compound was prepared in analogy to Example 12, from 4-(2,5-dichloro-phenoxy)-N-(2-methoxy-pyridin-3-yl)-nicotinamide. The compound was purified by preparative HPLC (Phenomenex Gemini column) using a gradient of acetonitrile:water (50:50 to 95:5). Light yellow solid (37%). MS (ESI): m/z=404.057 [M+H]$^+$.

Intermediate 4-(2,5-Dichloro-phenoxy)-N-(2-methoxy-pyridin-3-yl)-nicotinamide The title compound was prepared in analogy to Example 1, from 4-(2,5-dichloro-phenoxy)-nicotinic acid (Example 1, intermediate) and 3-amino-2-methoxypyridine (commercially available, CAS RN 20265-38-7). The compound was purified by preparative HPLC (Phenomenex Gemini column) using a gradient of acetonitrile:water (10:90 to 95:5). Light brown solid (28%). MS (ESI): m/z=390.040 [M+H]$^+$.

Example 16

4-(2,5-Dichloro-phenoxy)-N-(2-dimethylamino-phenyl)-N-methyl-nicotinamide

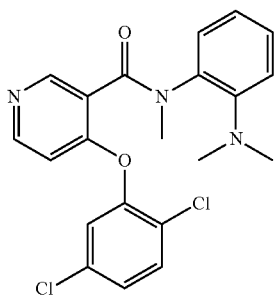 [SMILES: CN(C)c1ccccc1N(C)C(=O)c1cnccc1Oc1cc(Cl)ccc1Cl]

The title compound was prepared in analogy to Example 12, from 4-(2,5-dichloro-phenoxy)-N-(2-dimethylamino-phenyl)-nicotinamide. The compound was purified by silica gel chromatography using a MPLC system (CombiFlash Companion, Isco Inc.) eluting with a gradient of n-heptane:ethyl acetate (100:0 to 50:50), followed by a second chromatography on a preparative HPLC system (Phenomenex Gemini column) eluting with a gradient of acetonitrile:water (containing 0.05% formic acid) (10:90 to 98:2). Colorless oil (47%). MS (ESI): m/z=416.092 [M+H]$^+$.

Intermediate 4-(2,5-Dichloro-phenoxy)-N-(2-dimethylamino-phenyl)-nicotinamide The title compound was prepared in analogy to Example 1, from 4-(2,5-dichloro-phenoxy)-nicotinic acid (Example 1, intermediate) and N,N-dimethylbenzene-1,2-diamine (commercially available, CAS RN 2836-03-5). The compound was purified by preparative HPLC (Phenomenex Gemini column) using a gradient of acetonitrile:water (containing 0.05% formic acid) (10:90 to 98:2). Light brown foam (71%). MS (ESI): m/z=402.078 [M+H]$^+$.

Example 17

4-(2,5-Dichloro-phenoxy)-N-methyl-N-(2-piperidin-1-yl-phenyl)-nicotinamide

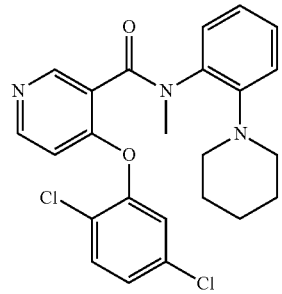 [SMILES: CN(C(=O)c1cnccc1Oc1cc(Cl)ccc1Cl)c1ccccc1N1CCCCC1]

The title compound was prepared in analogy to Example 12, from 4-(2,5-dichloro-phenoxy)-N-(2-piperidin-1-yl-phenyl)-nicotinamide. The compound was purified by preparative HPLC (Phenomenex Gemini column) using a gradient of acetonitrile:water (containing 0.05% formic acid) (10:90 to 98:2). White foam (88%). MS (ESI): 456.125 [M+H]$^+$.

Intermediate 4-(2,5-Dichloro-phenoxy)-N-(2-piperidin-1-yl-phenyl)-nicotinamide The title compound was prepared in analogy to Example 1, from 4-(2,5-dichloro-phenoxy)-nicotinic acid (Example 1, intermediate) and 2-piperidin-1-yl-phenylamine (commercially available; CAS RN 39643-31-7). White foam (90%). MS (ESI): 442.108 [M+H]$^+$.

Example 18

N-(3,5-Bis-trifluoromethyl-phenyl)-4-(2,5-dichloro-phenoxy)-N-methyl-nicotinamide

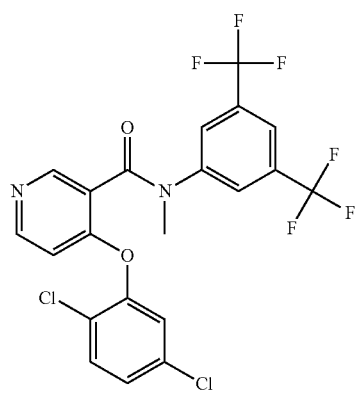 [SMILES: CN(C(=O)c1cnccc1Oc1cc(Cl)ccc1Cl)c1cc(C(F)(F)F)cc(C(F)(F)F)c1]

The title compound was prepared in analogy to Example 12, from N-(3,5-bis-trifluoromethyl-phenyl)-4-(2,5-dichloro-phenoxy)-nicotinamide. The compound was purified by preparative HPLC (Phenomenex Gemini column)

using a gradient of acetonitrile:water (containing 0.05% formic acid) (10:90 to 98:2). White foam (35%). MS (ESI): m/z=509.025 [M+H]⁺.

Intermediate

N-(3,5-Bis-trifluoromethyl-phenyl)-4-(2,5-dichloro-phenoxy)-nicotinamide

The title compound was prepared in analogy to Example 1, from 4-(2,5-dichloro-phenoxy)-nicotinic acid (Example 1, intermediate) and 3,5-bis(trifluoromethyl)aniline (commercially available; CAS RN 328-74-5) and using a gradient of n-heptane:ethyl acetate (100:0 to 40:60) for the chromatographic purification. Light yellow foam (44%). MS (ESI): m/z=495.010 [M+H]⁺.

Example 19

4-(2,5-Dichloro-phenoxy)-N-(4,5-difluoro-2-methoxy-phenyl)-N-methyl-nicotinamide

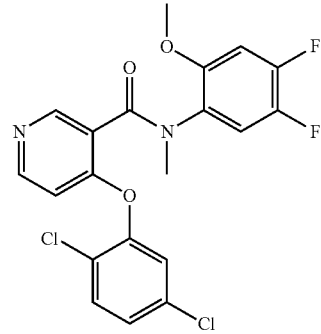 [SMILES: COc1cc(F)c(F)cc1N(C)C(=O)c1cnccc1Oc1cc(Cl)ccc1Cl]

The title compound was prepared in analogy to Example 12, from 4-(2,5-dichloro-phenoxy)-N-(4,5-difluoro-2-methoxy-phenyl)-nicotinamide. The residue was purified by preparative HPLC (Phenomenex Gemini column) using a gradient of acetonitrile:water (containing 0.05% formic acid) (10:90 to 98:2). White solid (51%). MS (ESI): m/z=439.042 [M+H]⁺.

Intermediate 4-(2,5-Dichloro-phenoxy)-N-(4,5-difluoro-2-methoxy-phenyl)-nicotinamide The title compound was prepared in analogy to Example 1, from 4-(2,5-dichloro-phenoxy)-nicotinic acid (Example 1, intermediate) and 4,5-difluoro-2-methoxyaniline (commercially available; CAS RN 1017779-71-3) and using a gradient of n-heptane:ethyl acetate (100:0 to 40:60) for the chromatographic purification. White solid (80%). MS (ESI): m/z=425.027 [M+H]⁺.

Example 20

N-(5-Chloro-2-dimethylamino-phenyl)-4-(2,5-dichloro-phenoxy)-N-methyl-nicotinamide

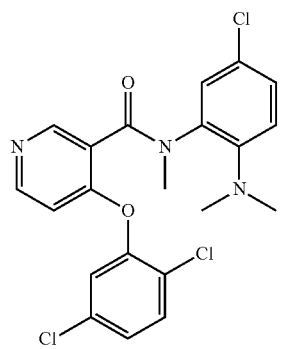 [SMILES: CN(C)c1ccc(Cl)cc1N(C)C(=O)c1cnccc1Oc1cc(Cl)ccc1Cl]

The title compound was prepared in analogy to Example 12, from N-(5-chloro-2-dimethylamino-phenyl)-4-(2,5-dichloro-phenoxy)-nicotinamide. White foam (85%). MS (ESI): m/z=450.054 [M+H]⁺.

Intermediate

N-(5-Chloro-2-dimethylamino-phenyl)-4-(2,5-dichloro-phenoxy)-nicotinamide

The title compound was prepared in analogy to Example 1, from 4-(2,5-dichloro-phenoxy)-nicotinic acid (Example 1, intermediate), (2-amino-4-chlorphenyl)dimethylamine dihydrochloride (commercially available, CAS RN 183251-88-9), using 5 mole equivalents of base and using a gradient of n-heptane:ethyl acetate (100:0 to 50:50) for the chromatographic purification. White solid (72%). MS (ESI): m/z=436.038 [M+H]⁺.

Example 21

4-(2,5-Dichloro-phenoxy)-N-(4,5-difluoro-2-methylamino-phenyl)-N-methyl-nicotinamide

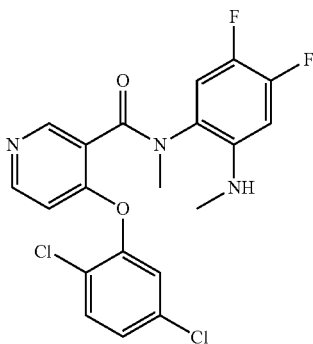 [SMILES: CNc1cc(F)c(F)cc1N(C)C(=O)c1cnccc1Oc1cc(Cl)ccc1Cl]

A solution of 100 mg (0.186 mmol) (2-{[4-(2,5-dichloro-phenoxy)-pyridine-3-carbonyl]-methyl-amino}-4,5-difluoro-phenyl)-methyl-carbamic acid tert-butyl ester in 1.5 mL 1M aqueous hydrochloric acid was stirred for 4 hours at 90° C. The reaction mixture was cooled down to room temperature and 2 mL 1M aqueous sodium hydroxide solution and 1 mL acetonitrile were added. The light yellow solution was directly purified by preparative HPLC (Phenomenex Gemini column) with a gradient of acetonitrile:water (containing 0.05% formic acid) (10:90 to 98:2) to give 18 mg (22%) of the title compound as a colorless solid. MS (ESI): m/z=438.058 [M+H]$^+$.

Intermediates a) (2-{[4-(2,5-Dichloro-phenoxy)-pyridine-3-carbonyl]-methyl-amino}-4,5-difluoro-phenyl)-methyl-carbamic acid tert-butyl ester The title compound was prepared in analogy to Example 12, from (2-{[4-(2,5-dichloro-phenoxy)-pyridine-3-carbonyl]-amino}-4,5-difluoro-phenyl)-carbamic acid tert-butyl ester and using a gradient of n-heptane:ethyl acetate (100:0 to 0:100) for the chromatographic purification. Colorless foam (63%). MS (ESI): m/z=538.111 [M+H]$^+$.

b) (2-{[4-(2,5-Dichloro-phenoxy)-pyridine-3-carbonyl]-amino}-4,5-difluoro-phenyl)-carbamic acid tert-butyl ester The title compound was prepared in analogy to Example 1, from 4-(2,5-dichloro-phenoxy)-nicotinic acid (Example 1, intermediate) and (2-amino-4,5-difluoro-phenyl)-carbamic acid tert-butyl ester (WO2008000643A1) and using a gradient of n-heptane:ethyl acetate (100:0 to 40:60) for the chromatographic purification. Light yellow solid (73%). MS (ESI): m/z=510.080 [M+H]$^+$.

Example 22

4-(2,5-Dichloro-phenoxy)-N-(1,2,3,4-tetrahydroquinolin-8-yl)-nicotinamide

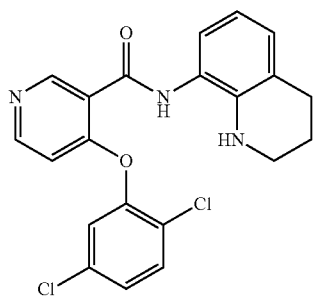 [SMILES: O=C(Nc1cccc2c1NCCC2)c1cnccc1Oc1cc(Cl)ccc1Cl]

The title compound was prepared in analogy to Example 1, from 4-(2,5-dichloro-phenoxy)-nicotinic acid (Example 1, intermediate) and 1,2,3,4-tetrahydro-quinolin-8-ylamine (commercially available; CAS RN 54012-92-9) and using a gradient of n-heptane:ethyl acetate (100:0 to 0:100) for the chromatographic purification. Light yellow solid (88%). MS (ESI): m/z=414.077 [M+H]$^+$.

Example 23

4-(2,5-Dichloro-phenoxy)-N-(2-dimethylamino-pyridin-3-yl)-N-methyl-nicotinamide

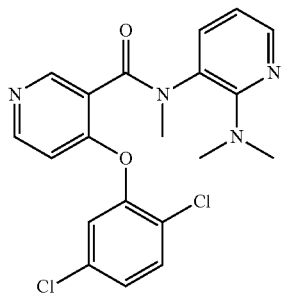 [SMILES: CN(C)c1ncccc1N(C)C(=O)c1cnccc1Oc1cc(Cl)ccc1Cl]

The title compound was prepared in analogy to Example 12, from 4-(2,5-dichloro-phenoxy)-N-(2-dimethylamino-pyridin-3-yl)-nicotinamide and using a gradient of n-heptane:ethyl acetate (100:0 to 0:100) for the chromatographic purification. Colorless oil (67%). MS (ESI): m/z=417.088 [M+H]$^+$.

Intermediate 4-(2,5-dichloro-phenoxy)-N-(2-dimethylamino-pyridin-3-yl)-nicotinamide The title compound was prepared in analogy to Example 1, from 4-(2,5-dichloro-phenoxy)-nicotinic acid (Example 1, intermediate), 3-amino-2-(dimethylamino)pyridine (commercially available, CAS RN 5028-25-1) and using a gradient of n-heptane:ethyl acetate (100:0 to 0:100) for the chromatographic purification. Light yellow solid (73%). MS (ESI): m/z=403.072 [M+H]$^+$.

Example 24

4-(2,5-Dichloro-phenoxy)-N-methyl-N-(1,2,3,4-tetrahydro-quinolin-8-yl)-nicotinamide

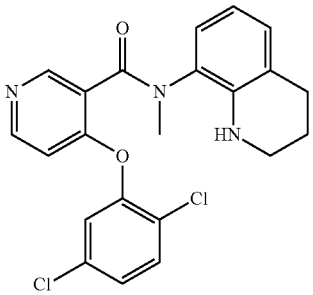 [SMILES: CN(C(=O)c1cnccc1Oc1cc(Cl)ccc1Cl)c1cccc2c1NCCC2]

The title compound was prepared in analogy to Example 12, from 4-(2,5-dichloro-phenoxy)-N-(1,2,3,4-tetrahydro-quinolin-8-yl)-nicotinamide (Example 22) and using a gradient of n-heptane:ethyl acetate (100:0 to 0:100) for the chromatographic purification. Colorless foam (42%). MS (ESI): m/z=428.092 [M+H]+.

Example 25

N-[4-Chloro-2-(cyclopropyl-methyl-amino)-5-fluoro-phenyl]-4-(2,5-dichloro-phenoxy)-N-methyl-nicotinamide

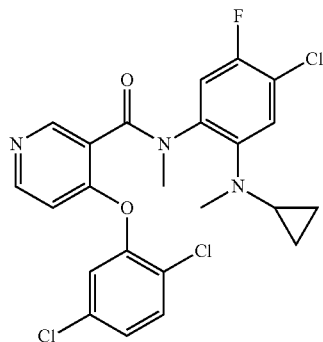 [SMILES: CN(C(=O)c1cnccc1Oc1cc(Cl)ccc1Cl)c1cc(F)c(Cl)cc1N(C)C1CC1]

The title compound was prepared in analogy to Example 12, from N-[4-chloro-2-(cyclopropyl-methyl-amino)-5-fluoro-phenyl]-4-(2,5-dichloro-phenoxy)-nicotinamide and using a gradient of n-heptane:ethyl acetate (100:0 to 0:100) for the chromatographic purification. Colorless solid (79%). MS (ESI): m/z=496.058 [M+H]+.

Intermediates a) N-[4-Chloro-2-(cyclopropyl-methyl-amino)-5-fluoro-phenyl]-4-(2,5-dichloro-phenoxy)-nicotinamide The title compound was prepared in analogy to Example 1, from 4-(2,5-dichloro-phenoxy)-nicotinic acid (Example 1, intermediate) and 4-chloro-N2-cyclopropyl-5-fluoro-N2-methyl-benzene-1,2-diamine and using a gradient of n-heptane:ethyl acetate (100:0 to 30:70) for the chromatographic purification. Colorless solid (70%). MS (ESI): m/z=446.083 [M+H]+.

b) 4-Chloro-N2-cyclopropyl-5-fluoro-N2-methyl-benzene-1,2-diamine

To a solution of 400 mg (16.35 mmol) (5-chloro-4-fluoro-2-nitro-phenyl)-cyclopropyl-methyl-amine in 4 mL methanol was added 40 mg 10% palladium on activated charcoal (Fluka). The reaction mixture was stirred at room temperature under a hydrogen atmosphere of 1.7 bar for two hours. Ethyl acetate (10 mL) was added and the reaction mixture was filtered over Dicalite® speed plus (Acros) and concentrated under vacuum. The residue was purified by silica gel chromatography using a MPLC system (CombiFlash Companion, Isco Inc.) eluting with a gradient of n-heptane:ethyl acetate (100:0 to 60:40) to give 240 mg (68%) of the title compound as a brown liquid. MS (ESI): m/z=215.075 [M+H]+.

c) (5-Chloro-4-fluoro-2-nitro-phenyl)-cyclopropyl-methyl-amine

To a solution of 500 mg (2.17 mmol) (5-chloro-4-fluoro-2-nitro-phenyl)-amine (J. Med. Chem. 1992, 35(8), 1385) in 5 mL N,N-dimethylformamide was added 104 mg (2.385 mmol) sodium hydride (60% dispersion in mineral oil) and 339 mg (2.385 mmol) methyl iodide. The reaction mixture was stirred for 6 hours at room temperature and then poured on 30 mL 10% aqueous sodium bicarbonate solution and 30 mL ethyl acetate. The layers were separated and the aqueous layer was extracted a second time with 30 mL ethyl acetate. The organic layers were washed with 30 mL brine, dried over magnesium sulfate, filtered and concentrated under vacuum. The residue was purified by silica gel chromatography using a MPLC system (CombiFlash Companion, Isco Inc.) eluting with a gradient of n-heptane:ethyl acetate 100:0 to 80:20) to give 433 mg (82%) of the desired compound as a yellow oil. MS (ESI): m/z=245.049 [M+H]+.

Example 26

[4-(4-Bromo-2,5-dichloro-phenoxy)-pyridin-3-yl]-(4-cyclopropyl-3,4-dihydro-2H-quinoxalin-1-yl)-methanone

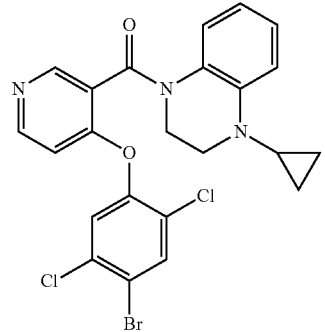 [SMILES: O=C(c1cnccc1Oc1cc(Cl)c(Br)cc1Cl)N1CCN(C2CC2)c2ccccc21]

To a suspension of 5.0 g (13.77 mmol) 4-(4-bromo-2,5-dichloro-phenoxy)-nicotinic acid in 30 mL N,N-dimethylformamide were added 5.50 g (14.46 mmol) O-(7-azabenzotriazol-1-yl)-N,N,N',N'-tetramethyluronium hexafluorophosphate (HATU, commercially available, CAS RN 148893-10-1) and 7.03 mL (41.32 mmol) N,N-diisopropylethylamine. To this brown solution was added 2.52 g (14.46 mmol) 1-cyclopropyl-1,2,3,4-tetrahydro-quinoxaline (Example 8, intermediate a), the resulting clear brown solution was stirred at room temperature for 17 hours and then poured on 120 mL water and 120 mL ethyl acetate. The resulting mixture was filtered, the filter cake was thoroughly washed with water and a very small amount of ethyl acetate to give after drying 6.55 g (92%) of the title compound as a brown solid. MS (ESI): m/z=520.1 [M+H]+.

Intermediate 4-(4-Bromo-2,5-dichloro-phenoxy)-nicotinic acid

To a stirred suspension of 6.0 g (38.08 mmol) 4-chloronicotinic acid (commercially available; CAS RN 10177-29-4) in 200 mL o-xylene were added 10.13 g (41.89 mmol) 4-bromo-2,5-dichlorophenol (commercially available; CAS RN 1940-42-7) and 2.84 g (7.62 mmol) tetrakis-(acetonitrile)-copper hexafluorophosphate (commercially available; CAS RN 64443-05-6). Then 31.31 g (95.20 mmol) cesium carbonate were added and the resulting dark brown suspension as heated to 120° C. for 16 hours. After cooling to room temperature, the sovent was evaporated, the residue dissolved in 1.25 l water, extracted four times with 250 mL ethyl acetate and filtered. The pH of the green filtrate was adjusted to 6 using 25% aqueous hydrochloric acid. The formed precipitate was filtered off to give a first batch of the desired compound.

The pH of the filtrate was adjusted to pH 3 using 25% aqueous hydrochloric acid, the suspension stirred for 0.25 hours at room temperature and then kept in the fridge for 64 hours. The suspension was filtered and washed with water to yield another batch of compound. Brown solid (overall yield 5.63 g (41%)). MS (ESI): m/z=363.9 [M+H]+.

Examples 27 and 28

2,5-Dichloro-4-[3-(4-cyclopropyl-3,4-dihydro-2H-quinoxaline-1-carbonyl)-pyridin-4-yloxy]-benzoic acid methyl ester and 4-Chloro-5-[3-(4-cyclopropyl-3,4-dihydro-2H-quinoxaline-1-carbonyl)-pyridin-4-yloxy]-phthalic acid dimethyl ester

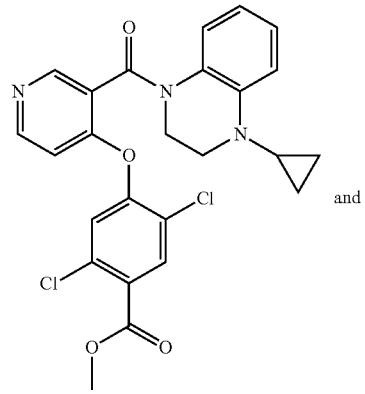

and

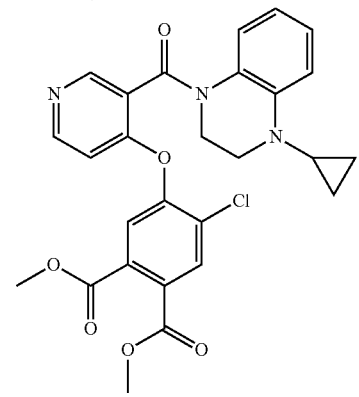

To a solution of 1.0 g (1.93 mmol) [4-(4-bromo-2,5-dichloro-phenoxy)-pyridin-3-yl]-(4-cyclopropyl-3,4-dihydro-2H-quinoxalin-1-yl)-methanone in 25 mL methanole and 25 mL ethyl acetate were added 0.40 mL (2.89 mmol) triethylamine and 0.094 g (0.12 mmol) 1,1'-bis(diphenylphosphino)ferrocene-palladium(II)dichloride dichloromethane adduct (commercially available, CAS RN 851232-71-8). Then, a 70 bar carbon monoxide atmosphere was installed and the reaction mixture was stirred at 120° C. for 20 hours. After cooling down, the reaction mixture was filtered and the filtrate was treated with silica gel and evaporated. The resulting powder was then purified by silica gel chromatography using a MPLC system (50 g silica gel column, CombiFlash Companion, Isco Inc.) eluting with a gradient of n-heptane:ethyl acetate (100:0 to 50:50) to give a first batch of each compound. The remaining fractions containing impurities were combined and again chromatographed (20 g silica gel column, CombiFlash Companion, Isco Inc.) using a gradient of n-heptane:ethyl acetate (100:0 to 40:60) to give a second batch of the desired compounds.

2,5-Dichloro-4-[3-(4-cyclopropyl-3,4-dihydro-2H-quinoxaline-1-carbonyl)-pyridin-4-yloxy]-benzoic acid methyl ester (Example 27): 0.413 g (43%) light brown foam. MS (ESI): m/z=498.3 [M+H]+.

4-Chloro-5-[3-(4-cyclopropyl-3,4-dihydro-2H-quinoxaline-1-carbonyl)-pyridin-4-yloxy]-phthalic acid dimethyl ester (Example 28): 0.278 g (27%) light brown foam. MS (ESI): m/z=522.142 [M+H]+.

Example 29

{2,5-Dichloro-4-[3-(4-cyclopropyl-3,4-dihydro-2H-quinoxaline-1-carbonyl)-pyridin-4-yloxy]-benzoylamino}-acetic acid methyl ester

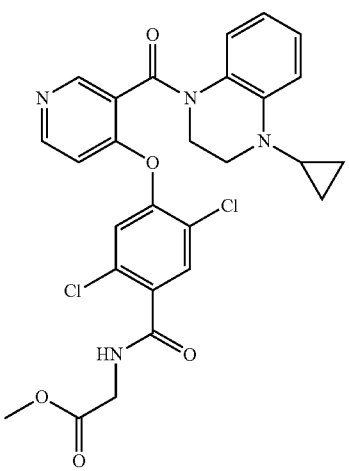 [SMILES: COC(=O)CNC(=O)c1cc(Cl)c(Oc2ccncc2C(=O)N2CCN(C3CC3)c3ccccc32)cc1Cl]

To a solution of 0.18 g (0.37 mmol) 2,5-dichloro-4-[3-(4-cyclopropyl-3,4-dihydro-2H-quinoxaline-1-carbonyl)-pyridin-4-yloxy]-benzoic acid in 2 mL N,N-dimethylformamide were added 0.148 g (0.39 mmol) O-(7-azabenzotriazol-1-yl)-N,N,N',N'-tetramethyluronium hexafluorophosphate (HATU, commercially available, CAS RN 148893-10-1) and 0.25 mL (1.49 mmol) N,N-diisopropylethylamine. To the light brown solution 0.049 g (0.39 mmol) glycine methyl ester hydrochloride (commercially available, CAS RN 5680-79-5) was added and the solution was stirred at room temperature for 2.5 hours. The solution was poured on water and extracted three times with ethyl acetate. The combined organic layers were washed twice with water and brine, dried over magnesium sulfate, filtered, treated with silica gel and evaporated. The resulting powder was purified by silica gel chromatography using a MPLC system (10 g silica gel column, CombiFlash Companion, Isco Inc.) with a gradient of n-heptane:ethyl acetate (100:0 to 0:100) to yield 0.169 g (82%) of the desired compound as a light brown solid. MS (ESI): m/z=555.12 [M+H]+.

Intermediate 2,5-Dichloro-4-[3-(4-cyclopropyl-3,4-dihydro-2H-quinoxaline-1-carbonyl)-pyridin-4-yloxy]-benzoic acid To a suspension of 3.68 g (7.38 mmol) 2,5-dichloro-4-[3-(4-cyclopropyl-3,4-dihydro-2H-quinoxaline-1-carbonyl)-pyridin-4-yloxy]-benzoic acid methyl ester (Example 27) in 40 mL dioxane and 40 mL water were added 0.387 g (9.22 mmol) lithium hydroxide mono hydrate. The reaction mixture was stirred 1.5 hours at room temperature upon which a yellow solution formed. Dioxane was removed by evaporation and the resulting suspension was diluted with 50 mL water and the pH was adjusted to 1 using 10 mL 25% aqueous hydrochloric acid. The resulting suspension was stirred for approx. 2 hours at room temperature, filtered, washed with water and dried under high vacuum to give 3.49 g (97%) of the desired compound as a light brown solid. MS (ESI): m/z=484.3 [M+H]+.

Example 30

{2,5-Dichloro-4-[3-(4-cyclopropyl-3,4-dihydro-2H-quinoxaline-1-carbonyl)-pyridin-4-yloxy]-benzoylamino}-acetic acid

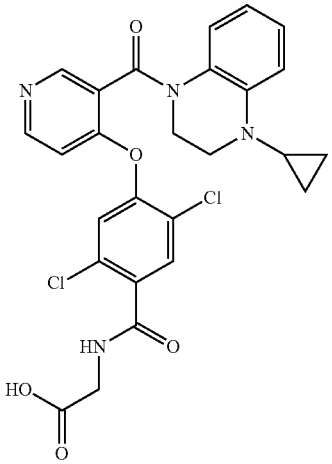 [SMILES: O=C(O)CNC(=O)c1cc(Cl)c(Oc2ccncc2C(=O)N2CCN(C3CC3)c3ccccc32)cc1Cl]

To a suspension of 0.148 g (0.27 mmol) {2,5-dichloro-4-[3-(4-cyclopropyl-3,4-dihydro-2H-quinoxaline-1-carbonyl)-pyridin-4-yloxy]-benzoylamino}-acetic acid methyl ester (Example 29) in 1.5 mL dioxane and 1.5 mL water was added 0.014 g (0.33 mmol) lithium hydroxide monohydrate. After 2 hours stirring at room temperature the organic solvent was evaporated. The pH of the resulting yellow solution was adjusted to 1 with 1M aqueous hydrochloric acid and the solution was extracted three times with ethyl acetate. The combined organic layers were washed with brine, dried over magnesium sulfate, filtered and evaporated to give 0.091 g (63%) of the title compound as a yellow foam. MS (ESI): m/z=541.104 [M+H]$^+$.

Example 31

({2,5-Dichloro-4-[3-(4-cyclopropyl-3,4-dihydro-2H-quinoxaline-1-carbonyl)-pyridin-4-yloxy]-benzoyl}-methyl-amino)-acetic acid methyl ester

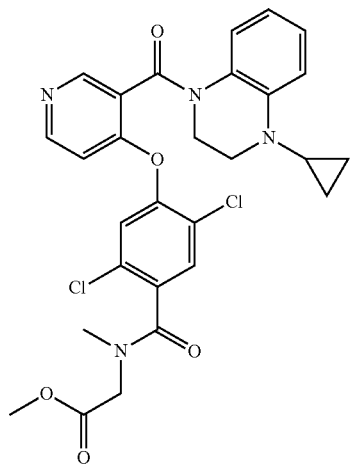 [SMILES: COC(=O)CN(C)C(=O)c1cc(Cl)c(Oc2ccncc2C(=O)N2CCN(C3CC3)c3ccccc32)cc1Cl]

The title compound was prepared in analogy to Example 29, from 2,5-dichloro-4-[3-(4-cyclopropyl-3,4-dihydro-2H-quinoxaline-1-carbonyl)-pyridin-4-yloxy]-benzoic acid (Example 29, intermediate) and sarcosine methylester hydrochloride (commercially available, CAS RN 945218-53-1) and using a gradient of n-heptane:ethyl acetate (100:0 to 0:100) as eluant. Light brown foam (33%). MS (ESI): m/z=569.135 [M+H]$^+$.

Example 32

({2,5-Dichloro-4-[3-(4-cyclopropyl-3,4-dihydro-2H-quinoxaline-1-carbonyl)-pyridin-4-yloxy]-benzoyl}-methyl-amino)-acetic acid

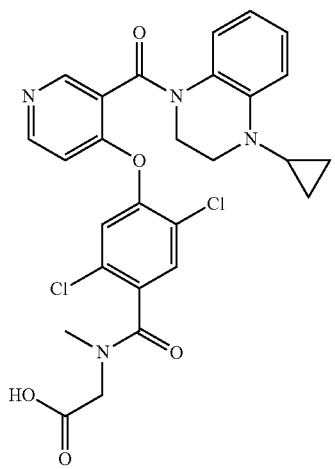 [SMILES: CN(CC(=O)O)C(=O)c1cc(Cl)c(Oc2ccncc2C(=O)N2CCN(C3CC3)c3ccccc32)cc1Cl]

To a solution of 0.057 g (0.10 mmol) ({2,5-dichloro-4-[3-(4-cyclopropyl-3,4-dihydro-2H-quinoxaline-1-carbonyl)-pyridin-4-yloxy]-benzoyl}-methyl-amino)-acetic acid methyl ester (Example 31) in 1 mL dioxane and 1 mL water was added 0.005 g (0.12 mmol) lithium hydroxide monohydrate. After stirring at room temperature for 2 hours, dioxane was removed by evaporation. The pH of the formed yellow solution was adjusted to 1 with 1M aqueous hydrochloric acid. The aqueous solution was saturated with solid sodium chloride and extracted three times with ethyl acetate. The combined organic layers were washed with brine, dried over magnesium sulfate, filtered and evaporated to give 0.053 g (95%) of the title compound as a yellow solid. MS (ESI): m/z=555.12 [M+H]$^+$.

Example 33

3-{2,5-Dichloro-4-[3-(4-cyclopropyl-3,4-dihydro-2H-quinoxaline-1-carbonyl)-pyridin-4-yloxy]-benzoylamino}-propionic acid ethyl ester

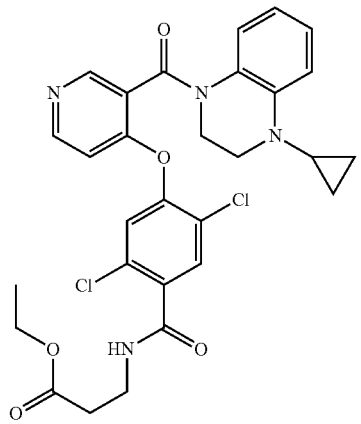 [SMILES: CCOC(=O)CCNC(=O)c1cc(Cl)c(Oc2ccncc2C(=O)N2CCN(C3CC3)c3ccccc32)cc1Cl]

To a solution of 0.18 g (0.37 mmol) 2,5-dichloro-4-[3-(4-cyclopropyl-3,4-dihydro-2H-quinoxaline-1-carbonyl)-pyridin-4-yloxy]-benzoic acid (Example 29, intermediate) in 2 mL N,N-dimethylformamide were added 0.148 g (0.39 mmol) O-(7-azabenzotriazol-1-yl)-N,N,N',N'-tetramethyluronium hexafluorophosphate (HATU, commercially available, CAS RN 148893-10-1) and 0.25 mL (1.49 mmol) N,N-diisopropylethylamine. To the light brown solution 0.060 g (0.39 mmol) beta-alanine ethylester hydrochloride (commercially available, CAS RN 4244-84-2) was added and the solution was stirred at room temperature for 3.5 hours. The solution was poured on water and extracted three times with ethyl acetate. The combined organic layers were washed twice with water and brine, dried over magnesium sulfate, filtered, treated with silica gel and evaporated. The resulting powder was purified by silica gel chromatography using a MPLC system (10 g silica gel column, CombiFlash Companion, Isco Inc.) with a gradient of n-heptane:ethyl acetate (100:0 to 0:100) to afford 0.185 g (85%) of the title compound as a light brown foam. MS (ESI): m/z=583.15 [M+H]$^+$.

Example 34

3-{2,5-Dichloro-4-[3-(4-cyclopropyl-3,4-dihydro-2H-quinoxaline-1-carbonyl)-pyridin-4-yloxy]-benzoylamino}-propionic acid

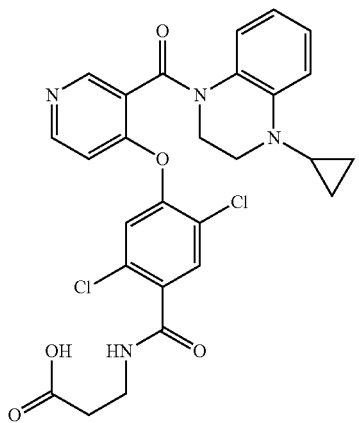

To a solution of 0.85 g (1.46 mmol) 3-{2,5-dichloro-4-[3-(4-cyclopropyl-3,4-dihydro-2H-quinoxaline-1-carbonyl)-pyridin-4-yloxy]-benzoylamino}-propionic acid ethyl ester (Example 33) in 7.5 mL dioxane were added 7.5 mL water and 0.076 g (1.81 mmol) lithium hydroxide monohydrate. The resulting suspension was stirred for 2.25 hours at room temperature and dioxane was removed by evaporation. The pH of the solution was adjusted to 2.5 by adding 1.9 mL 1M aqueous hydrochloric acid and the suspension was stirred for 2 hours at room temperature. The suspension was filtered, the filter cake washed with water and dried under high vacuum to give 0.70 g (86%) of the desired compound as an off-white solid. MS (ESI): m/z=555.12 [M+H]$^+$.

Example 35

2-{2,5-Dichloro-4-[3-(4-cyclopropyl-3,4-dihydro-2H-quinoxaline-1-carbonyl)-pyridin-4-yloxy]-benzoylamino}-ethanesulfonic acid

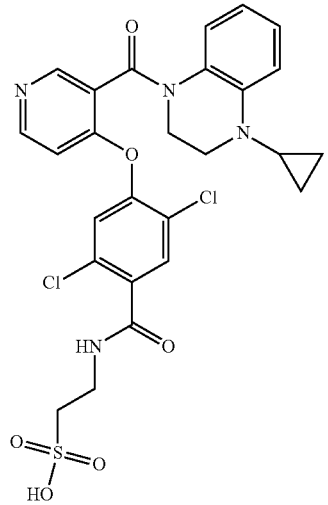 [SMILES: O=C(NCCS(=O)(=O)O)c1cc(Cl)c(Oc2ccncc2C(=O)N2CCN(C3CC3)c3ccccc32)cc1Cl]

To a solution of 0.127 g (0.26 mmol) 2,5-dichloro-4-[3-(4-cyclopropyl-3,4-dihydro-2H-quinoxaline-1-carbonyl)-pyridin-4-yloxy]-benzoic acid (Example 29, intermediate) in 1.5 mL N,N-dimethylformamide were added 0.10 g (0.26 mmol) O-(7-azabenzotriazol-1-yl)-N,N,N',N'-tetramethyluronium hexafluorophosphate (HATU, commercially available, CAS RN 148893-10-1) and 0.13 mL (0.79 mmol) N,N-diisopropylethylamine. To the yellow solution 0.036 g (0.29 mmol) taurine (commercially available, CAS RN 107-35-7) was added and the reaction mixture stirred at room temperature for 4.5 hours. The solution was filtered using a syringe micro filter and purified on a preparative HPLC system (Phenomenex Gemini column) with a gradient of acetonitrile:water (containing 0.05% formic acid) (10:90 to 98:2) to give 0.092 g (59%) of the title compound as a brown solid. MS (ESI): m/z=591.086 [M+H]$^+$.

Example 36

2-({2,5-Dichloro-4-[3-(4-cyclopropyl-3,4-dihydro-2H-quinoxaline-1-carbonyl)-pyridin-4-yloxy]-benzoyl}-methyl-amino)-ethanesulfonic acid

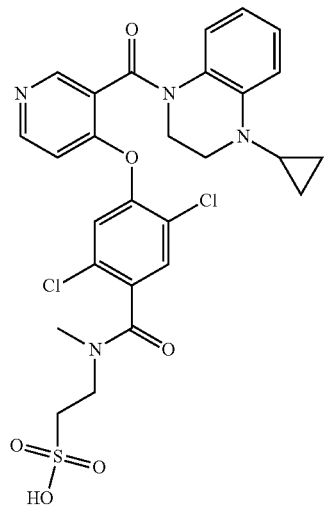 [SMILES: CN(CCS(=O)(=O)O)C(=O)c1cc(Cl)c(Oc2ccncc2C(=O)N2CCN(C3CC3)c3ccccc32)cc1Cl]

The title compound was prepared in analogy to Example 35, from 2,5-dichloro-4-[3-(4-cyclopropyl-3,4-dihydro-2H-quinoxaline-1-carbonyl)-pyridin-4-yloxy]-benzoic acid (Example 29, intermediate) and N-methyl taurine (commercially available, CAS RN 107-68-6). Brown solid (27%). MS (ESI): m/z=605.2 [M+H]⁺.

Example 37

3-{2,5-Dichloro-4-[3-(4-cyclopropyl-3,4-dihydro-2H-quinoxaline-1-carbonyl)-pyridin-4-yloxy]-benzoylamino}-propane-1-sulfonic acid

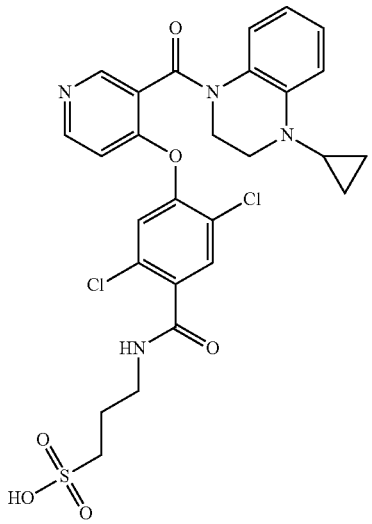 [SMILES: O=C(NCCCS(=O)(=O)O)c1cc(Cl)c(Oc2ccncc2C(=O)N2CCN(C3CC3)c3ccccc32)cc1Cl]

The title compound was prepared in analogy to Example 35, from 2,5-dichloro-4-[3-(4-cyclopropyl-3,4-dihydro-2H-quinoxaline-1-carbonyl)-pyridin-4-yloxy]-benzoic acid (Example 29, intermediate) and 3-amino-1-propanesulfonic acid (commercially available, CAS RN 3687-18-1). Brown solid (18%). MS (ESI): m/z=605.102 [M+H]⁺.

Example 38

2,5-Dichloro-4-[3-(4-cyclopropyl-3,4-dihydro-2H-quinoxaline-1-carbonyl)-pyridin-4-yloxy]-N-(1H-tetrazol-5-yl)-benzamide

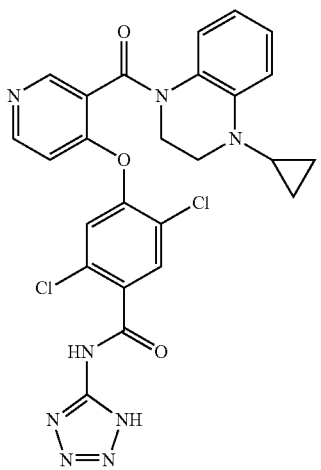 [SMILES: O=C(Nc1nnn[nH]1)c1cc(Cl)c(Oc2ccncc2C(=O)N2CCN(C3CC3)c3ccccc32)cc1Cl]

To a solution of 0.20 g (0.41 mmol) 2,5-dichloro-4-[3-(4-cyclopropyl-3,4-dihydro-2H-quinoxaline-1-carbonyl)-pyridin-4-yloxy]-benzoic acid (Example 29, intermediate) in 2 mL N,N-dimethylformamide were added 0.165 g (0.43 mmol) O-(7-azabenzotriazol-1-yl)-N,N,N',N'-tetramethyluronium hexafluorophosphate (HATU, commercially available, CAS RN 148893-10-1) and 0.21 mL (1.24 mmol) N,N-diisopropylethylamine. To the yellow solution 0.037 g (0.43 mmol) 5-amino-1H-tetrazole (commercially available, CAS RN 4418-61-5) was added and the solution was stirred at room temperature for 3.25 hours. Then the solution was heated to 60° C. and stirred at this temperature for 88 hours. After filtration over a syringe micro filter, the reaction mixture was purified by preparative HPLC (Phenomenex Gemini column) with a gradient of acetonitrile:water (containing 0.05% formic acid) (10:90 to 98:2) to give the desired compound as a light brown solid (0.051 g, 22%). MS (ESI): m/z=551.11 [M+H]⁺.

Example 39

2,5-Dichloro-4-[3-(4-cyclopropyl-3,4-dihydro-2H-quinoxaline-1-carbonyl)-pyridin-4-yloxy]-N-(1H-tetrazol-5-ylmethyl)-benzamide

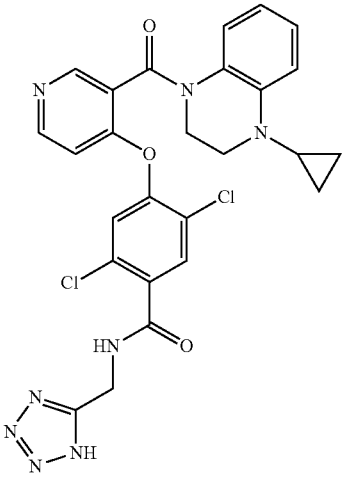 [SMILES: O=C(NCc1nnn[nH]1)c1cc(Cl)c(Oc2ccncc2C(=O)N2CCN(C3CC3)c3ccccc32)cc1Cl]

The title compound was prepared in analogy to Example 38, from 2,5-dichloro-4-[3-(4-cyclopropyl-3,4-dihydro-2H-quinoxaline-1-carbonyl)-pyridin-4-yloxy]-benzoic acid (Example 29, intermediate) and 5-(aminomethyl)-tetrazole (commercially available, CAS RN 31602-63-8) to provide 0.078 g (58%) of the title compound as a light yellow solid. MS (ESI): m/z=565.126 [M+H]⁺.

Example 40

4-{2,5-Dichloro-4-[3-(4-cyclopropyl-3,4-dihydro-2H-quinoxaline-1-carbonyl)-pyridin-4-yloxy]-benzoylamino}-butyric acid

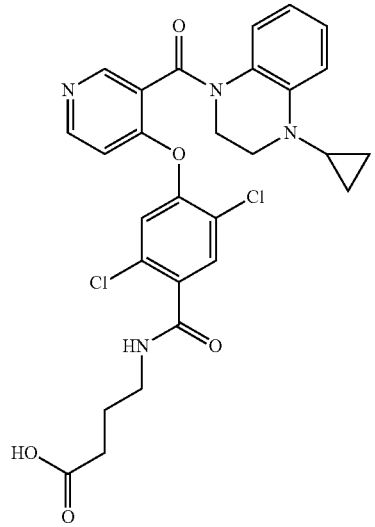 [SMILES: O=C(O)CCCNC(=O)c1cc(Cl)c(Oc2ccncc2C(=O)N2CCN(C3CC3)c3ccccc32)cc1Cl]

The title compound was prepared in analogy to Example 30, from 4-{2,5-dichloro-4-[3-(4-cyclopropyl-3,4-dihydro-2H-quinoxaline-1-carbonyl)-pyridin-4-yloxy]-benzoylamino}-butyric acid methyl ester. Light brown solid (62%). MS (ESI): m/z=569.136 [M+H]+.

Intermediate

4-{2,5-Dichloro-4-[3-(4-cyclopropyl-3,4-dihydro-2H-quinoxaline-1-carbonyl)-pyridin-4-yloxy]-benzoylamino}-butyric acid methyl ester The title compound was prepared in analogy to Example 1, from 2,5-dichloro-4-[3-(4-cyclopropyl-3,4-dihydro-2H-quinoxaline-1-carbonyl)-pyridin-4-yloxy]-benzoic acid (Example 29, intermediate) and methyl 4-aminobutyrate (commercially available, CAS RN 3251-07-8) and using a gradient of n-heptane:ethyl acetate (100:0 to 0:100) for the chromatographic purification. Light brown foam (42%). MS (ESI): m/z=583.150 [M+H]+.

Example 41

4-{2,5-Dichloro-4-[3-(4-cyclopropyl-3,4-dihydro-2H-quinoxaline-1-carbonyl)-pyridin-4-yloxy]-benzoylamino}-1-methyl-1H-pyrrole-2-carboxylic acid methyl ester

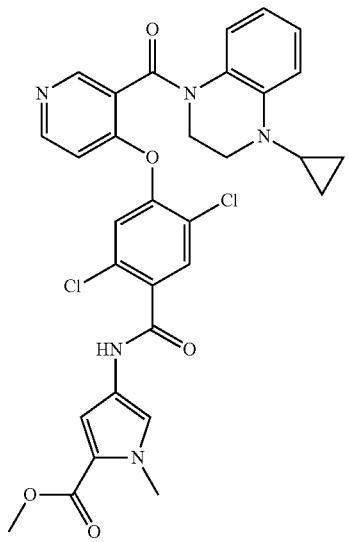 [SMILES: COC(=O)c1cc(NC(=O)c2cc(Cl)c(Oc3ccncc3C(=O)N3CCN(C4CC4)c4ccccc43)cc2Cl)cn1C]

The title compound was prepared in analogy to Example 1, from 2,5-dichloro-4-[3-(4-cyclopropyl-3,4-dihydro-2H-quinoxaline-1-carbonyl)-pyridin-4-yloxy]-benzoic acid (Example 29, intermediate) and 4-amino-1-methyl-1H-pyrrole-2-carboxylic acid methyl ester (commercially available, CAS RN 180258-45-1) and using a gradient of n-heptane:ethyl acetate (100:0 to 0:100) for the chromatographic purification. Light brown foam (70%). MS (ESI): m/z=620.147 [M+H]+.

Example 42

4-{2,5-Dichloro-4-[3-(4-cyclopropyl-3,4-dihydro-2H-quinoxaline-1-carbonyl)-pyridin-4-yloxy]-benzoylamino}-1-methyl-1H-pyrrole-2-carboxylic acid

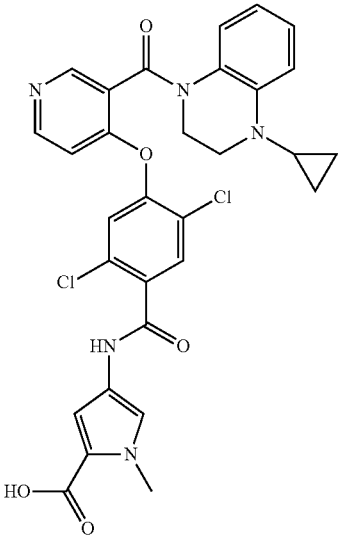 [SMILES: Cn1cc(NC(=O)c2cc(Cl)c(Oc3ccncc3C(=O)N3CCN(C4CC4)c4ccccc43)cc2Cl)cc1C(=O)O]

To a solution of 0.10 g (0.16 mmol) 4-{2,5-dichloro-4-[3-(4-cyclopropyl-3,4-dihydro-2H-quinoxaline-1-carbonyl)-pyridin-4-yloxy]-benzoylamino}-1-methyl-1H-pyrrole-2-carboxylic acid methyl ester (Example 41) in 1 mL dioxane were added 1 mL water and 0.008 g (0.19 mmol) lithiumhydroxide monohydrate. The resulting suspension was stirred for 2 hours at room temperature, then heated to 80° C. for 5.5 hours. Another 0.001 g (0.024 mmol) lithiumhydroxide monohydrate were added and the reaction mixture was heated for another 1.5 hours at 80° C. After stirring at room temperature for 64 hours the reaction mixture was poured on 1M aqueous hydrochloric acid and ethyl acetate and the layers were separated. The aqueous layer was extracted three times with ethyl acetate. The combined organic layers were washed with brine, dried over magnesium sulfate, filtered and evaporated. The residue was dissolved in N,N-dimethylformamide, filtered over a syringe microfilter and purified by preparative HPLC (Phenomenex Gemini column) with a gradient of acetonitrile:water (containing 0.05% formic acid) (10:90 to 98:2) to give the title compound as a light brown solid (0.034 g, 35%). MS (ESI): m/z=606.13 [M+H]+.

Example 43

4-{2,5-Dichloro-4-[3-(4-cyclopropyl-3,4-dihydro-2H-quinoxaline-1-carbonyl)-pyridin-4-yloxy]-benzoylamino}-benzoic acid methyl ester

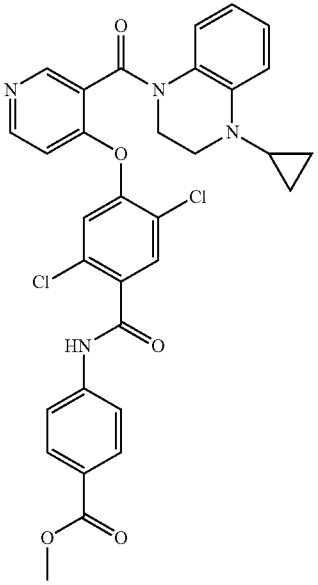 [SMILES: COC(=O)c1ccc(NC(=O)c2cc(Cl)c(Oc3ccncc3C(=O)N3CCN(C4CC4)c4ccccc43)cc2Cl)cc1]

The title compound was prepared in analogy to Example 1, from 2,5-dichloro-4-[3-(4-cyclopropyl-3,4-dihydro-2H-quinoxaline-1-carbonyl)-pyridin-4-yloxy]-benzoic acid (Example 29, intermediate) and 4-amino-benzoic acid methyl ester (commercially available, CAS RN 619-45-4) and using a gradient of n-heptane:ethyl acetate (100:0 to 0:100) for the chromatographic purification. Light brown foam (29%). MS (ESI): m/z=617.136 [M+H]$^+$.

Example 44

4-{2,5-Dichloro-4-[3-(4-cyclopropyl-3,4-dihydro-2H-quinoxaline-1-carbonyl)-pyridin-4-yloxy]-benzoylamino}-benzoic acid

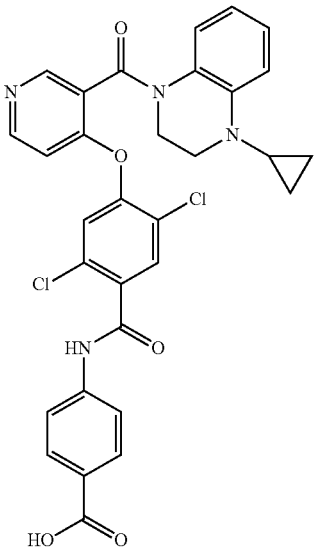 [SMILES: O=C(O)c1ccc(NC(=O)c2cc(Cl)c(Oc3ccncc3C(=O)N3CCN(C4CC4)c4ccccc43)cc2Cl)cc1]

To a solution of 0.040 g (0.065 mmol) 4-{2,5-dichloro-4-[3-(4-cyclopropyl-3,4-dihydro-2H-quinoxaline-1-carbonyl)-pyridin-4-yloxy]-benzoylamino}-benzoic acid methyl ester (Example 43) in 0.5 mL dioxane were added 0.5 mL water and 0.003 g (0.071 mmol) lithiumhydroxide monohydrate. The resulting suspension was stirred at room temperature for 2 h, followed by heating to 80° C. for 1 hour. The organic solvent was removed by evaporation and the pH of the resulting solution was adjusted to 1 to 2 using 1M aqueous hydrochloric acid. The suspension was stirred for 2 hours at room temperature, filtered and washed with water to yield the desired compound as a light brown solid (0.020 g, 51%). MS (ESI): m/z=603.12 [M+H]$^+$.

Example 45

2-{2,5-Dichloro-4-[3-(4-cyclopropyl-3,4-dihydro-2H-quinoxaline-1-carbonyl)-pyridin-4-yloxy]-benzoylamino}-4-methyl-thiazole-5-carboxylic acid ethyl ester

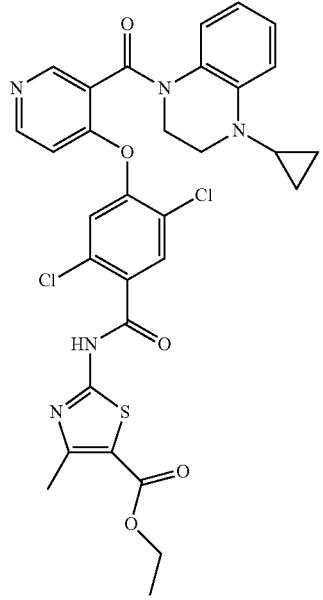 [SMILES: CCOC(=O)c1sc(NC(=O)c2cc(Cl)c(Oc3ccncc3C(=O)N3CCN(C4CC4)c4ccccc43)cc2Cl)nc1C]

The title compound was prepared in analogy to Example 1, from 2,5-dichloro-4-[3-(4-cyclopropyl-3,4-dihydro-2H-quinoxaline-1-carbonyl)-pyridin-4-yloxy]-benzoic acid (Example 29, intermediate) and 2-amino-4-methyl-thiazole-5-carboxylic acid ethyl ester (commercially available, CAS RN 7210-76-6) and using a gradient of n-heptane:ethyl acetate (100:0 to 0:100) for the chromatographic purification. Yellow solid (0.182 g; 67%). MS (ESI): m/z=652.12 [M+H]$^+$.

Example 46

2-{2,5-Dichloro-4-[3-(4-cyclopropyl-3,4-dihydro-2H-quinoxaline-1-carbonyl)-pyridin-4-yloxy]-benzoylamino}-4-methyl-thiazole-5-carboxylic acid

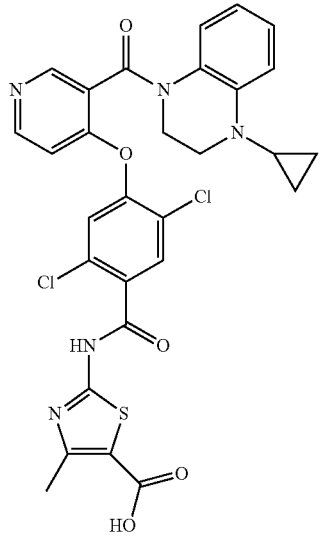 [SMILES: Cc1nc(NC(=O)c2cc(Cl)c(Oc3ccncc3C(=O)N3CCN(C4CC4)c4ccccc43)cc2Cl)sc1C(=O)O]

To a solution of 0.16 g (0.25 mmol) 2-{2,5-dichloro-4-[3-(4-cyclopropyl-3,4-dihydro-2H-quinoxaline-1-carbonyl)-pyridin-4-yloxy]-benzoylamino}-4-methyl-thiazole-5-carboxylic acid ethyl ester (Example 45) in 2 mL dioxane were added 2 mL water and 0.013 g (0.31 mmol) lithiumhydroxide monohydrate. The resulting suspension was stirred at room temperature for 2 hours and then stirred at reflux temperature for 5.5 hours. Another 0.013 g (0.31 mmol) lithiumhydroxide monohydrate were added and heating was continued for another 8 hours. The oil bath was removed and the reaction mixture was stirred at room temperature overnight. After evaporation of the organic solvent the pH of the resulting solution was adjusted to 2 to 3 using 1M aqueous hydrochloric acid and the solution was extracted three times with ethyl acetate. The combined organic layers were washed with brine, dried over magnesium sulfate, filtered and evaporated. The product was purified by preparative HPLC (Phenomenex Gemini Column) with a gradient of acetonitrile:water (containing 0.05% formic acid) (10:90 to 98:2) to give 0.058 g (37%) of the title compound as a light brown solid. MS (ESI): m/z=624.1 [M+H]+.

Example 47

5-{2,5-Dichloro-4-[3-(4-cyclopropyl-3,4-dihydro-2H-quinoxaline-1-carbonyl)-pyridin-4-yloxy]-benzoylamino}-[1,3,4]thiadiazole-2-carboxylic acid ethyl ester

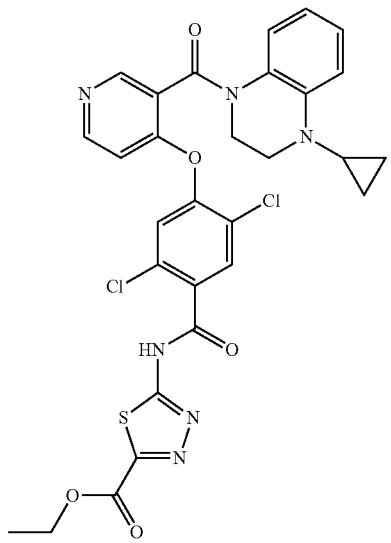 [SMILES: CCOC(=O)c1nnc(NC(=O)c2cc(Cl)c(Oc3ccncc3C(=O)N3CCN(C4CC4)c4ccccc43)cc2Cl)s1]

The title compound was prepared in analogy to Example 1, from 2,5-dichloro-4-[3-(4-cyclopropyl-3,4-dihydro-2H-quinoxaline-1-carbonyl)-pyridin-4-yloxy]-benzoic acid (Example 29, intermediate) and 5-amino-[1,3,4]thiadiazole-2-carboxylic acid ethyl ester (commercially available, CAS RN 64837-53-2) and using a gradient of n-heptane:ethyl acetate (100:0 to 0:100) for the chromatographic purification. Yellow solid (67%). MS (ESI): m/z=652.12 [M+H]+.

Example 48

2,5-Dichloro-4-[3-(4-cyclopropyl-3,4-dihydro-2H-quinoxaline-1-carbonyl)-pyridin-4-yloxy]-N-[1,3,4]thiadiazol-2-yl-benzamide

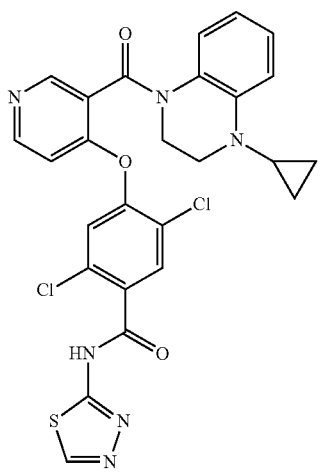 [SMILES: O=C(Nc1nncs1)c1cc(Cl)c(Oc2ccncc2C(=O)N2CCN(C3CC3)c3ccccc32)cc1Cl]

To a solution of 0.10 g (0.16 mmol) 5-{2,5-dichloro-4-[3-(4-cyclopropyl-3,4-dihydro-2H-quinoxaline-1-carbonyl)-pyridin-4-yloxy]-benzoylamino}-[1,3,4]thiadiazole-2-carboxylic acid ethyl ester (Example 47) in 1 mL dioxane were added 1 mL water and 0.008 g (0.19 mmol) lithiumhydroxide monohydrate. The resulting suspension was stirred for 2 hours at room temperature and then at 80° C. for 5.5 hours. Another 0.001 g (0.024 mmol) lithiumhydroxide monohydrate was added and the reaction mixture was heated for another 1.5 hours at 80° C. After stirring at room temperature for 64 hours the reaction mixture was poured on 1M aqueous hydrochloric acid and ethyl acetate and the layers were separated. The aqueous layer was extracted three times with ethyl acetate. The combined organic layers were washed with brine, dried over magnesium sulfate, filtered and evaporated. The residue was dissolved in N,N-dimethylformamide, filtered over a syringe microfilter and purified by preparative HPLC (Phenomenex Gemini column) with a gradient of acetonitrile:water (containing 0.05% formic acid) (10:90 to 98:2) to give 0.030 g (33%) of the product as a light yellow solid. MS (ESI): m/z=567.08 [M+H]⁺.

Example 49

2,5-Dichloro-4-[3-(4-cyclopropyl-3,4-dihydro-2H-quinoxaline-1-carbonyl)-pyridin-4-yloxy]-N-(2-hydroxy-ethyl)-benzamide

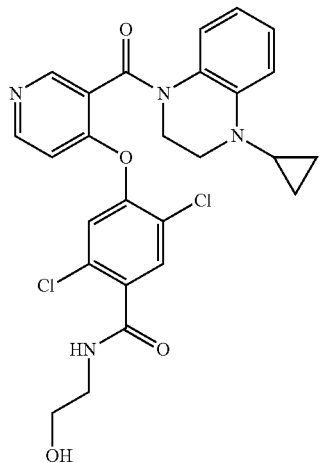 [SMILES: O=C(NCCO)c1cc(Cl)c(Oc2ccncc2C(=O)N2CCN(C3CC3)c3ccccc32)cc1Cl]

The title compound was prepared in analogy to Example 1, from 2,5-dichloro-4-[3-(4-cyclopropyl-3,4-dihydro-2H-quinoxaline-1-carbonyl)-pyridin-4-yloxy]-benzoic acid (Example 29, intermediate) and 2-amino-ethanol (commercially available, CAS RN 141-43-5). The product was purified on a preparative HPLC system (Phenomenex Gemini column) using a gradient of acetonitrile:water (containing 0.05% formic acid) (10:90 to 98:2) to give the desired compound as a light brown foam (60%). MS (ESI): m/z=527.124 [M+H]⁺.

Example 50

2,5-Dichloro-4-[3-(4-cyclopropyl-3,4-dihydro-2H-quinoxaline-1-carbonyl)-pyridin-4-yloxy]-N,N-bis-(2-hydroxy-ethyl)-benzamide

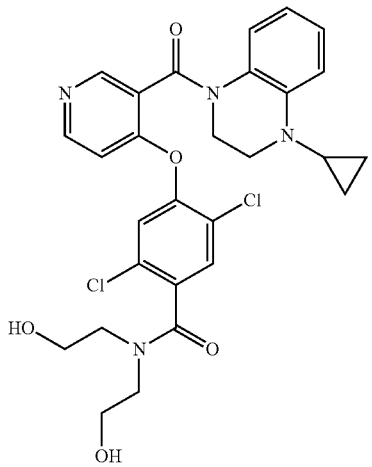 [SMILES: O=C(c1cc(Cl)c(Oc2ccncc2C(=O)N2CCN(C3CC3)c3ccccc32)cc1Cl)N(CCO)CCO]

The title compound was prepared in analogy to Example 1, from 2,5-dichloro-4-[3-(4-cyclopropyl-3,4-dihydro-2H-quinoxaline-1-carbonyl)-pyridin-4-yloxy]-benzoic acid (Example 29, intermediate) and 2-(2-hydroxy-ethylamino)-ethanol (commercially available, CAS RN 111-42-2). The product was purified on a preparative HPLC system (Phenomenex Gemini column) using a gradient of acetonitrile:water (containing 0.05% formic acid) (10:90 to 98:2) to give the desired compound as a light brown solid (71%). MS (ESI): m/z=571.150 [M+H]⁺.

Example 51

2,5-Dichloro-4-[3-(4-cyclopropyl-3,4-dihydro-2H-quinoxaline-1-carbonyl)-pyridin-4-yloxy]-N-(2-hydroxy-1-hydroxymethyl-ethyl)-benzamide

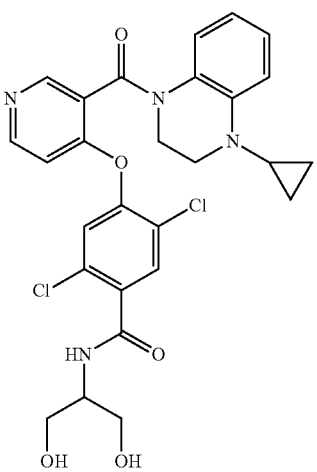 [SMILES: O=C(NC(CO)CO)c1cc(Cl)c(Oc2ccncc2C(=O)N2CCN(C3CC3)c3ccccc32)cc1Cl]

The title compound was prepared in analogy to Example 1, from 2,5-dichloro-4-[3-(4-cyclopropyl-3,4-dihydro-2H-quinoxaline-1-carbonyl)-pyridin-4-yloxy]-benzoic acid (Example 29, intermediate) and 2-amino-propane-1,3-diol (commercially available, CAS RN 534-03-2). The product was purified on a preparative HPLC system (Phenomenex Gemini column) using a gradient of acetonitrile:water (containing 0.05% formic acid) (10:90 to 98:2) to give the desired compound as a light brown foam (72%). MS (ESI): m/z=559.2 [M+H]$^+$.

Example 52

2,5-Dichloro-4-[3-(4-cyclopropyl-3,4-dihydro-2H-quinoxaline-1-carbonyl)-pyridin-4-yloxy]-benzamide

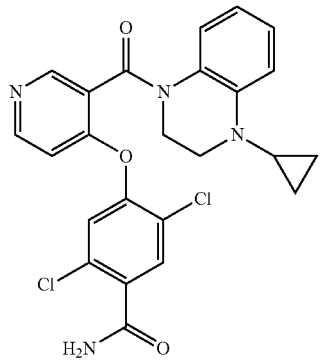 [SMILES: NC(=O)c1cc(Cl)c(Oc2ccncc2C(=O)N2CCN(C3CC3)c3ccccc32)cc1Cl]

To a solution of 0.10 g (0.21 mmol) 2,5-dichloro-4-[3-(4-cyclopropyl-3,4-dihydro-2H-quinoxaline-1-carbonyl)-pyridin-4-yloxy]-benzoic acid (Example 29, intermediate) in 1 mL N,N-dimethylformamide were added 0.022 g (0.41 mmol) ammonium chloride, 0.028 g (0.21 mmol) 1-hydroxybenzotriazole, 0.07 mL N,N-diisopropylethylamine and 0.040 g (0.21 mmol) N-(3-dimethylaminopropyl)-N'-ethylcarbodiimide hydrochloride. The resulting mixture was stirred at room temperature overnight, filtered over a syringe micro filter and purified on a preparative HPLC system (Phenomenex Gemini column) using a gradient of acetonitrile:water (containing 0.05% formic acid) (10:90 to 98:2) to afford 80 mg (80%) of the desired compound as a light brown solid. MS (ESI): m/z=483.098 [M+H]$^+$.

Example 53

N-(2-Carbamoyl-ethyl)-2,5-dichloro-4-[3-(4-cyclopropyl-3,4-dihydro-2H-quinoxaline-1-carbonyl)-pyridin-4-yloxy]-benzamide

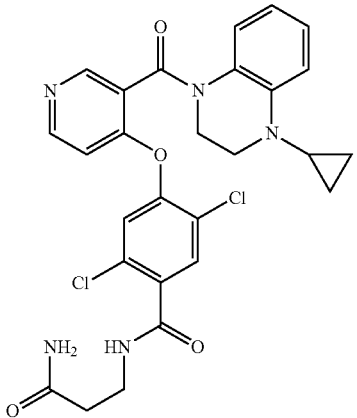 [SMILES: NC(=O)CCNC(=O)c1cc(Cl)c(Oc2ccncc2C(=O)N2CCN(C3CC3)c3ccccc32)cc1Cl]

The title compound was prepared in analogy to Example 52, from 3-{2,5-dichloro-4-[3-(4-cyclopropyl-3,4-dihydro-2H-quinoxaline-1-carbonyl)-pyridin-4-yloxy]-benzoylamino}-propionic acid (Example 34) and 3-amino-propionamide (commercially available, CAS RN 4726-85-6). Light brown foam (74%). MS (ESI): m/z=554.136 [M+H]$^+$.

Example 54

4-{2,5-Dichloro-4-[3-(4-cyclopropyl-3,4-dihydro-2H-quinoxaline-1-carbonyl)-pyridin-4-yloxy]-benzoylamino}-heptanedioic acid dimethyl ester

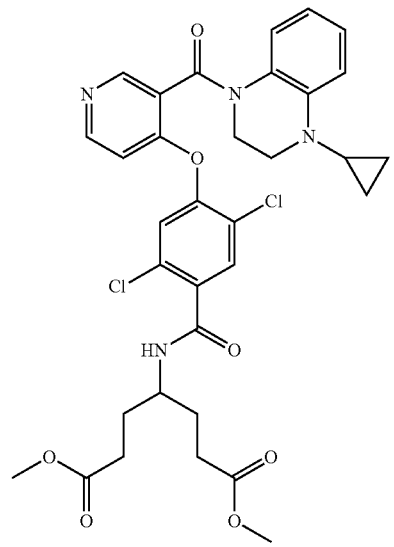 [SMILES: COC(=O)CCC(CCC(=O)OC)NC(=O)c1cc(Cl)c(Oc2ccncc2C(=O)N2CCN(C3CC3)c3ccccc32)cc1Cl]

The title compound was prepared in analogy to Example 1, from 2,5-dichloro-4-[3-(4-cyclopropyl-3,4-dihydro-2H-quinoxaline-1-carbonyl)-pyridin-4-yloxy]-benzoic acid (Example 29, intermediate) and 4-amino-heptanedioic acid dimethyl ester (J. Am. Chem. Soc. 2005, 127 (50), 17877-17887) and using a gradient of n-heptane:ethyl acetate (100:0 to 0:100) for the chromatographic purification. Light brown foam (69%). MS (ESI): m/z=669.19 [M+H]$^+$.

Example 55

(4-Cyclopropyl-3,4-dihydro-2H-quinoxalin-1-yl)-[4-(2,5-dichloro-4-hydroxymethyl-phenoxy)-pyridin-3-yl]-methanone

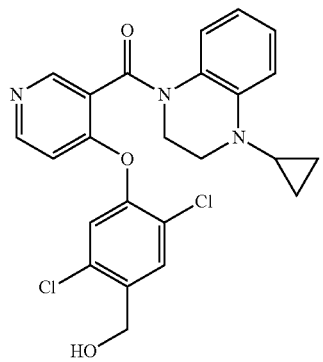 [SMILES: O=C(c1cnccc1Oc1cc(Cl)c(CO)cc1Cl)N1CCN(C2CC2)c2ccccc21]

To a solution of 0.10 g (0.20 mmol) 2,5-dichloro-4-[3-(4-cyclopropyl-3,4-dihydro-2H-quinoxaline-1-carbonyl)-pyridin-4-yloxy]-benzoic acid methyl ester (Example 27) in 1 mL tetrahydrofuran was added 0.008 g (0.21 mmol) lithium aluminium hydride. The resulting suspension was stirred at room temperature for 2.5 hours, poured on aqueous saturated sodium bicarbonate solution and extracted three times with ethyl acetate. The combined organic layers were washed with brine, dried over magnesium sulfate, filtered, treated with silica gel and evaporated to dryness. The resulting powder was purified by silica gel chromatography using a MPLC system (10 g silica gel column, CombiFlash Companion, Isco Inc.) with a gradient of n-heptane:ethyl acetate (100:0 to 50:50) to give 0.025 g (26%) of the desired compound as a light brown oil. MS (ESI): m/z=470.103 [M+H]+.

Example 56

2,5-Dichloro-4-[3-(4-cyclopropyl-3,4-dihydro-2H-quinoxaline-1-carbonyl)-pyridin-4-yloxy]-benzonitrile

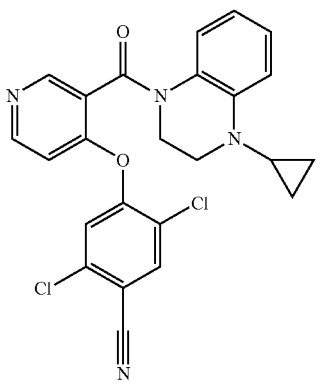 [SMILES: N#Cc1cc(Cl)c(Oc2ccncc2C(=O)N2CCN(C3CC3)c3ccccc32)cc1Cl]

To a suspension of 0.20 g (0.43 mmol) [4-(4-bromo-2,5-dichloro-phenoxy)-pyridin-3-yl]-(4-cyclopropyl-3,4-dihydro-2H-quinoxalin-1-yl)-methanone (Example 26) in 0.2 mL N,N-dimethylformamide was added 0.044 g (0.38 mmol) L-proline (commercially available, CAS RN 147-85-3) followed by the addition of 0.068 g (0.76 mmol) copper(I) cyanide. The resulting dark brown suspension was stirred at 120° C. for 17 hours. Then another 0.2 mL N,N-dimethylformamide were added and stirring was continued for another 7 hours at 120° C. The reaction was allowed to cool to room temperature, stirred for another 64 hours and then partioned between water and ethyl acetate. The resulting turbid mixture was filtered and washed with ethyl acetate. The layers of the filtrate were separated and the water layer extracted twice with ethyl acetate. The combined organic layers were washed with brine, dried over magnesium sulfate, filtered and evaporated to dryness. The remaining light brown oil was dissolved in dichloromethane, treated with silica gel and then evpaorated. The resulting powder was purified by silica gel chromatography using a MPLC system (10 g silica gel column, CombiFlash Companion, Isco Inc.) with a gradient of n-heptane:ethyl acetate (100:0 to 40:60) to afford 0.045 g (25%) of the title compound as a brown solid. MS (ESI): m/z=465.1 [M+H]+.

Example 57

(4-Cyclopropyl-3,4-dihydro-2H-quinoxalin-1-yl)-[4-(2,5-dichloro-4-hydroxy-phenoxy)-pyridin-3-yl]-methanone

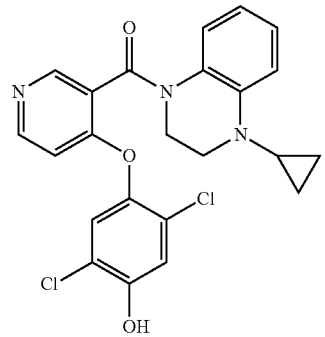 [SMILES: O=C(c1cnccc1Oc1cc(Cl)c(O)cc1Cl)N1CCN(C2CC2)c2ccccc21]

To a solution of 1.0 g (1.93 mmol) [4-(4-bromo-2,5-dichloro-phenoxy)-pyridin-3-yl]-(4-cyclopropyl-3,4-dihydro-2H-quinoxalin-1-yl)-methanone (Example 26) in 20 mL dry tetrahydrofuran was added 0.85 mL (3.72 mmol) triisopropylborate (commercially available, CAS RN 5419-55-6). The solution was cooled to −75° C. using a dry ice bath and 1.50 mL (2.4 mmol) n-butyllithium solution (1.6M in n-hexane) was added over 3 min. to the reaction mixture. Stirring was continued for another 1.5 hours. The dry-ice bath was replaced by an ice bath and 0.98 g (8.17 mmol) acetic acid (50% solution in water) and 0.28 g (2.89 mmol) hydrogen peroxide (35% solution in water) were added. The reaction mixture was stirred at 0° C. for 1 hour, the cooling batch was removed and stirring was continued at room temperature for 20 hours. The solution was poured on 10% aqueous sodium thiosulfate solution and extracted three times with ethyl acetate. The combined organic layers were washed with brine, dried over magnesium sulfate, filtered, treated with silica gel and evaporated to dryness. The resulting powder was purified by silica gel chromatography using a MPLC system (20 g silica gel column, CombiFlash Companion, Isco Inc.) with a gradient of n-heptane:ethyl acetate (100:0 to 40:60) to give 0.575 g (65%) of the title compound as a light brown solid. MS (ESI): m/z=456.2 [M+H]+.

Example 58

{2,5-Dichloro-4-[3-(4-cyclopropyl-3,4-dihydro-2H-quinoxaline-1-carbonyl)-pyridin-4-yloxy]-phenoxy}-acetic acid ethyl ester

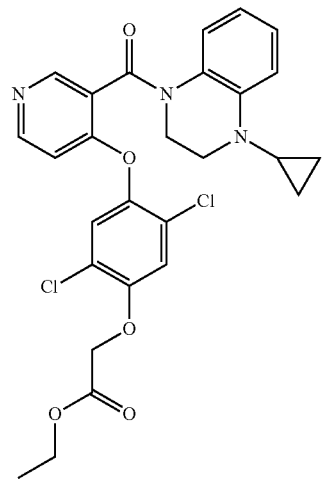 [SMILES: CCOC(=O)COc1cc(Cl)c(Oc2ccncc2C(=O)N2CCN(C3CC3)c3ccccc32)cc1Cl]

To a solution of 0.15 g (0.33 mmol) (4-cyclopropyl-3,4-dihydro-2H-quinoxalin-1-yl)-[4-(2,5-dichloro-4-hydroxy-phenoxy)-pyridin-3-yl]-methanone (Example 57) in 2 mL N,N-dimethylformamide was added 0.016 g (0.37 mmol) sodium hydride (60% dispersion in mineral oil, Aldrich, CAS RN 7646-69-7). The reaction mixture was stirred for 15 min. at room temperature before 0.04 mL (0.36 mmol) ethyl bromoacetate (commercially available, CAS RN 105-36-2) were added. After stirring at room temperature for 3 hours the solution was poured on water and extracted three times with ethyl acetate. The combined organic layers were washed with water and brine, dried over magnesium sulfate, filtered, treated with silica gel and evaporated. The resulting powder was purified by silica gel chromatography using a MPLC system (10 g silica gel column, CombiFlash Companion, Isco Inc.) eluting with a gradient of n-heptane:ethyl acetate (100:0 to 30:70) to give 0.144 g (81%) of the desired compound as a light yellow foam. MS (ESI): m/z=542.123 [M+H]$^+$.

Example 59

{2,5-Dichloro-4-[3-(4-cyclopropyl-3,4-dihydro-2H-quinoxaline-1-carbonyl)-pyridin-4-yloxy]-phenoxy}-acetic acid

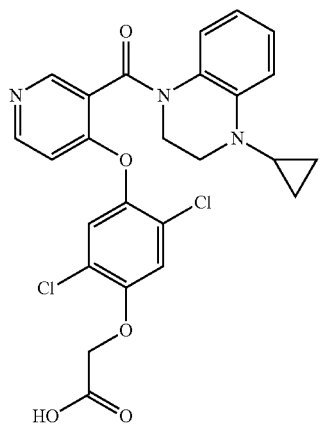 [SMILES: O=C(O)COc1cc(Cl)c(Oc2ccncc2C(=O)N2CCN(C3CC3)c3ccccc32)cc1Cl]

The title compound was prepared in analogy to Example 30, from {2,5-dichloro-4-[3-(4-cyclopropyl-3,4-dihydro-2H-quinoxaline-1-carbonyl)-pyridin-4-yloxy]-phenoxy}-acetic acid ethyl ester after a reaction time of 4 hours at room temperature and stirring of the suspension obtained after acidification for 2 hours at room temperature. Light brown solid (72%). MS (ESI): m/z=514.092 [M+H]$^+$.

Example 60

2-{2,5-Dichloro-4-[3-(4-cyclopropyl-3,4-dihydro-2H-quinoxaline-1-carbonyl)-pyridin-4-yloxy]-phenoxy}-2-methyl-propionic acid ethyl ester

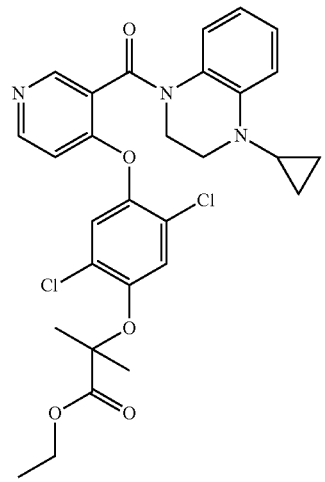 [SMILES: CCOC(=O)C(C)(C)Oc1cc(Cl)c(Oc2ccncc2C(=O)N2CCN(C3CC3)c3ccccc32)cc1Cl]

The title compound was prepared in analogy to Example 58, from (4-cyclopropyl-3,4-dihydro-2H-quinoxalin-1-yl)-[4-(2,5-dichloro-4-hydroxy-phenoxy)-pyridin-3-yl]-methanone (Example 57) and 2-bromo-2-methyl-propionic acid ethyl ester (commercially available, CAS RN 600-00-0) after a reaction time of 23 hours at room temperature and using a gradient of n-heptane:ethyl acetate (100:0 to 40:60) for the chromatographic purification. Light brown foam (30%). MS (ESI): m/z=570.156 [M+H]$^+$.

Example 61

2-{2,5-Dichloro-4-[3-(4-cyclopropyl-3,4-dihydro-2H-quinoxaline-1-carbonyl)-pyridin-4-yloxy]-phenoxy}-2-methyl-propionic acid

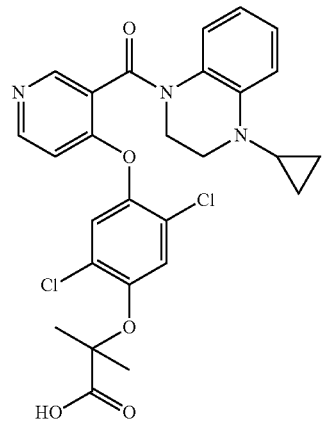 [SMILES: CC(C)(Oc1cc(Cl)c(Oc2ccncc2C(=O)N2CCN(C3CC3)c3ccccc32)cc1Cl)C(=O)O]

The title compound was prepared in analogy to Example 30, from 2-{2,5-dichloro-4-[3-(4-cyclopropyl-3,4-dihydro-2H-quinoxaline-1-carbonyl)-pyridin-4-yloxy]-phenoxy}-2-methyl-propionic acid ethyl ester. Light brown solid (61%). MS (ESI): m/z=542.124 [M+H]$^+$.

Example 62

(4-Cyclopropyl-3,4-dihydro-2H-quinoxalin-1-yl)-{4-[2,5-dichloro-4-(2-hydroxy-ethoxy)-phenoxy]-pyridin-3-yl}-methanone

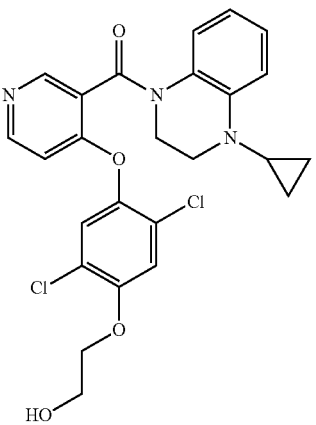 [SMILES: O=C(c1cnccc1Oc1cc(Cl)c(OCCO)cc1Cl)N1CCN(C2CC2)c2ccccc21]

To a solution of 0.15 g (0.33 mmol) (4-cyclopropyl-3,4-dihydro-2H-quinoxalin-1-yl)-[4-(2,5-dichloro-4-hydroxy-phenoxy)-pyridin-3-yl]-methanone (Example 57) in 2 mL N,N-dimethylformamide was added 0.016 g (0.37 mmol) sodium hydride (60% dispersion in mineral oil, Aldrich). The reaction mixture was stirred for 15 min. at room temperature before 0.03 mL (0.36 mmol) 2-bromoethanol (commercially available, CAS RN 540-51-2) were added. After stirring for 3 hours at room temperature another 0.03 mL (0.36 mmol) 2-bromoethanole were added. After 72 hours the reaction mixture was poured on water and was extracted three times with ethyl acetate. The organic layers were washed with water and brine, dried over magnesium sulfate, filtered, treated with silica gel and evaporated. The resulting powder was purified by silica gel chromatography using a MPLC system (20 g silica gel column, CombiFlash Companion, Isco Inc.) with a gradient of n-heptane:ethyl acetate (100:0 to 25:75) to give 0.075 g (46%) of the title compound as a light brown foam. MS (ESI): m/z=500.113 [M+H]$^+$.

Example 63

(4-Cyclopropyl-3,4-dihydro-2H-quinoxalin-1-yl)-[4-(2,5-dichloro-phenoxy)-6-methyl-pyridin-3-yl]-methanone

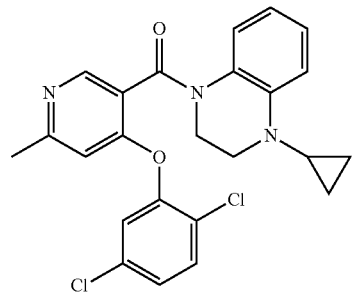 [SMILES: Cc1cc(Oc2cc(Cl)ccc2Cl)c(C(=O)N2CCN(C3CC3)c3ccccc32)cn1]

To a solution of 420 mg (1.381 mmol) lithium 4-(2,5-dichloro-phenoxy)-6-methyl-nicotinate in 6 mL dry N,N-dimethylformamide was added 1.17 mL (6.907 mmol) N-ethyldiisopropylamine and 635 mg (1.658 mmol) O-(7-azabenzotriazol-1-yl)-N,N,N',N'-tetramethyluronium hexafluorophosphate (HATU, commercially available, CAS RN 148893-10-1) and 289 mg (1.658 mmol) 1-cyclopropyl-1,2,3,4-tetrahydro-quinoxaline (Example 8, intermedaite a). The reaction mixture was stirred for 18 hours at room temperature and then poured on 30 mL 10% aqueous sodium bicarbonate solution and 30 mL ethyl acetate. The layers were separated and the aqueous layer was extracted a second time with 30 mL ethyl acetate. The organic layers were washed with 30 mL brine, dried over magnesium sulfate, filtered and concentrated under vacuum. The residue was purified by silica gel chromatography using a MPLC system (20 g silica gel column, CombiFlash Companion, Isco Inc.) with gradient of n-heptane:ethyl acetate (100:0 to 0:100) to give 375 mg (60%) of the title compound as a light yellow solid. MS (ESI): m/z=454.108 [M+H]$^+$.

Intermediates a) Lithium 4-(2,5-dichloro-phenoxy)-6-methyl-nicotinate

To a solution of 420 mg (1.345 mmol) 4-(2,5-dichloro-phenoxy)-6-methyl-nicotinic acid methyl ester in 5 mL dioxane was added 5 mL water and 85 mg (2.018 mmol) lithium hydroxide monohydrate. The reaction mixture was stirred for 2 hours at room temperature and then concentrated under vacuum. The so-obtained light yellow solid was pure enough for the next step without further purification. MS (ESI): m/z=298.004 [M+H]$^+$.

b) 4-(2,5-Dichloro-phenoxy)-6-methyl-nicotinic acid methyl ester

To a solution of 0.53 g (2.855 mmol) 4-chloro-6-methyl-nicotinic acid methyl ester (commercially available, CAS RN 886372-05-0) in 7.5 mL dry N,N-dimethylformamide was added 489 mg (2.998 mmol) 2,5-dichlorophenol, 789 mg (5.711 mmol) potassium carbonate, 54 mg (0.286 mmol) copper(I)iodide and 54 mg (0.857 mmol) copper nanopowder (avg. particel size 100 nm). The reaction mixture was stirred at 120° C. for 3 hours and then poured on 30 mL 1M aqueous hydrochloric acid and 30 mL ethyl acetate. The layers were separated and the aqueous layer was extracted with 30 mL ethyl acetate. The combined organic layers were washed with 30 mL brine, dried over magnesium sulfate, filtered and concentrated under vacuum. The residue was purified by silica gel chromatography using a MPLC system (20 g silica gel column, CombiFlash Companion, Isco Inc.) with a gradient of n-heptane:ethyl acetate (100:0 to 0:100), to give 432 mg (48%) of the compound as a light yellow solid. MS (ESI): m/z=312.019 [M+H]$^+$.

Example 64

[4-(4-Bromo-2,5-dichloro-phenoxy)-6-methyl-pyridin-3-yl]-(4-cyclopropyl-3,4-dihydro-2H-quinoxalin-1-yl)-methanone

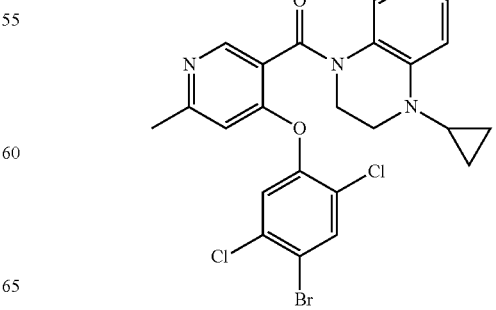

To a solution of 0.17 g (0.451 mmol) 4-(4-bromo-2,5-dichloro-phenoxy)-6-methyl-nicotinic acid in 3 mL dry N,N-dimethylformamide was added 0.38 mL (2.225 mmol) N-ethyldiisopropylamine and 207 mg (0.541 mmol) O-(7-azabenzotriazol-1-yl)-N,N,N',N'-tetramethyluronium hexafluorophosphate (HATU, commercially available, CAS RN 148893-10-1) and 94 mg (0.541 mmol) 1-cyclopropyl-1,2,3,4-tetrahydro-quinoxaline (Example 8, intermediate a). The reaction mixture was stirred at room temperature for 18 hours and then poured on 30 mL 10% aqueous sodium bicarbonate solution and 30 mL ethyl acetate. The layers were separated. The aqueous layer was extracted with 30 mL ethyl acetate and the combined organic layers were washed with 30 mL brine, dried over magnesium sulfate, filtered and concentrated under vacuum. The residue was purified by silica gel chromatography using a MPLC system (20 g silica gel column, CombiFlash Companion, Isco Inc.) with a gradient of n-heptane:ethyl acetate (100:0 to 40:60) to give 55 mg (23%) of the title compound as a light yellow solid. MS (ESI): m/z=534.018 [M+H]$^+$.

Intermediate a) 4-(4-Bromo-2,5-dichloro-phenoxy)-6-methyl-nicotinic acid

To a solution of 185 mg (0.473 mmol) 4-(4-bromo-2,5-dichloro-phenoxy)-6-methyl-nicotinic acid methyl ester in 3 mL dioxane was added 3 mL water and 30 mg (0.710 mmol) lithium hydroxide monohydrate. The reaction mixture was stirred for 4 hours at room temperature, poured on 30 mL 1M aqueous hydrochloric acid and 30 mL dichloromethane and the layers were separated. The aqueous layer was extracted with 30 mL dichloromethane and the combined organic layers were washed with 30 mL brine, dried over magnesium sulfate, filtered and concentrated under vacuum to afford 178 mg (100%) of the title compound as a colorless solid. MS (ESI): m/z=377.912 [M+H]$^+$.

b) 4-(4-Bromo-2,5-dichloro-phenoxy)-6-methyl-nicotinic acid methyl ester

To a solution of 1.25 g (6.734 mmol) 4-chloro-6-methyl-nicotinic acid methyl ester (commercially available, CAS RN 886372-05-0) in 30 mL o-xylene was added 1.792 g (7.408 mmol) 4-bromo-2,5-dichlorophenol (commercially available, CAS RN 1940-42-7), 0.502 g (1.347 mmol) tetrakis(acetonitrile)copper (I) hexafluorophosphate (commercially available, CAS RN 64443-05-6) and 5.536 g (16.836 mmol) cesium carbonate. The reaction mixture was stirred at 120° C. for 20 hours and was then allowed to cool to room temperature. Ethyl acetate (50 mL) and water (50 mL) was added and stirring was continued for another 10 minutes. The reaction mixture was filtered over Dicalite® speed plus (Acros) and the layers were separated. The aqueous layer was extracted with 200 mL ethyl acetate and the combined organic layers were washed with 200 mL brine, dried over magnesium sulfate, filtered and concentrated under vacuum. The residue was purified by silica gel chromatography using a MPLC system (50 g silica gel column, CombiFlash Companion, Isco Inc.) and a gradient of n-heptane:ethyl acetate (100:0 to 40:60) to give 200 mg (8%) of the title compound as a light yellow solid. MS (Turbo Spray): m/z=391.9 [M+H]$^+$.

Example 65

2,5-Dichloro-4-[5-(4-cyclopropyl-3,4-dihydro-2H-quinoxaline-1-carbonyl)-2-methyl-pyridin-4-yloxy]-benzoic acid methyl ester

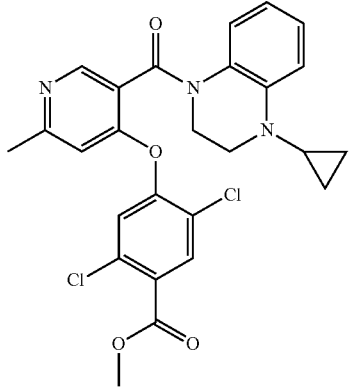 [SMILES: COC(=O)c1cc(Cl)c(Oc2cc(C)ncc2C(=O)N2CCN(C3CC3)c3ccccc32)cc1Cl]

To a solution of 0.23 g (0.431 mmol) [4-(4-bromo-2,5-dichloro-phenoxy)-6-methyl-pyridin-3-yl]-(4-cyclopropyl-3,4-dihydro-2H-quinoxalin-1-yl)-methanone (Example 64) in 5 mL methanol and 5 mL ethyl acetate was added 23 mg (0.028 mmol) 1,1'-bis(diphenyl-phosphino)ferrocene-palladium(II)dichloride dichloromethane complex (commercially available, CAS RN 851232-71-8) and 90 mg (0.647 mmol) triethylamine. The solution was carbonylated with carbon monoxide at 100° C. at 90 bar. The reaction mixture was purified by silica gel chromatography using a MPLC system (CombiFlash Companion, Isco Inc.) eluting with a gradient of n-heptane:ethyl acetate (100:0 to 0:100) to give the desired compound as a light yellow solid (142 mg, 64.3%). MS (ESI): m/z=512.114 [M+H]$^+$.

Example 66

2,5-Dichloro-4-[5-(4-cyclopropyl-3,4-dihydro-2H-quinoxaline-1-carbonyl)-2-methyl-pyridin-4-yloxy]-benzoic acid

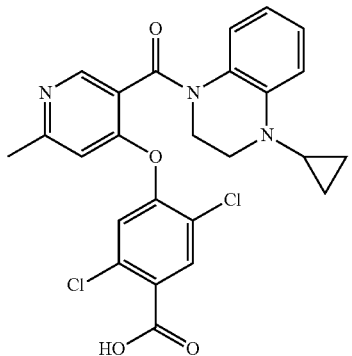 [SMILES: Cc1cc(Oc2cc(Cl)c(C(=O)O)cc2Cl)c(C(=O)N2CCN(C3CC3)c3ccccc32)cn1]

To a solution of 130 mg (0.254 mmol) 2,5-dichloro-4-[5-(4-cyclopropyl-3,4-dihydro-2H-quinoxaline-1-carbonyl)-2-methyl-pyridin-4-yloxy]-benzoic acid methyl ester (Example 65) in 2 mL dioxane was added 2 mL water and 13 mg (0.317 mmol) lithium hydroxide monohydrate. The reaction mixture was stirred at room temperature for 4 hours and then poured on 20 mL 1N aqueous hydrochloric acid and 20 mL ethyl acetate The layers were separated and the aqueous layer was extracted with 20 mL ethyl acetate. The combined organic layers were washed with 30 mL brine, dried over magnesium sulfate, filtered and concentrated under vacuum to give 125 mg (98.9%) of the title compound as a light yellow solid. MS (ESI): m/z=498.098 [M+H]$^+$.

Example 67

3-{2,5-Dichloro-4-[5-(4-cyclopropyl-3,4-dihydro-2H-quinoxaline-1-carbonyl)-2-methyl-pyridin-4-yloxy]-benzoylamino}-propionic acid ethyl ester

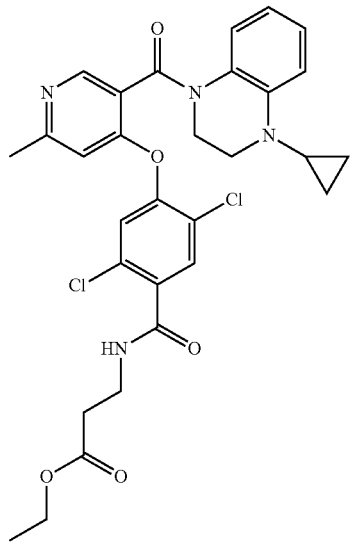 [SMILES: CCOC(=O)CCNC(=O)c1cc(Cl)c(Oc2cc(C)ncc2C(=O)N2CCN(C3CC3)c3ccccc32)cc1Cl]

The title compound was prepared in analogy to Example 29, from 2,5-dichloro-4-[5-(4-cyclopropyl-3,4-dihydro-2H-quinoxaline-1-carbonyl)-2-methyl-pyridin-4-yloxy]-benzoic acid and beta-alanine ethylester hydrochloride (commercially available, CAS RN 4244-84-2). Colorless foam (73%). MS (ESI): m/z=597.169 [M+H]$^+$.

Example 68

3-{2,5-Dichloro-4-[5-(4-cyclopropyl-3,4-dihydro-2H-quinoxaline-1-carbonyl)-2-methyl-pyridin-4-yloxy]-benzoylamino}-propionic acid

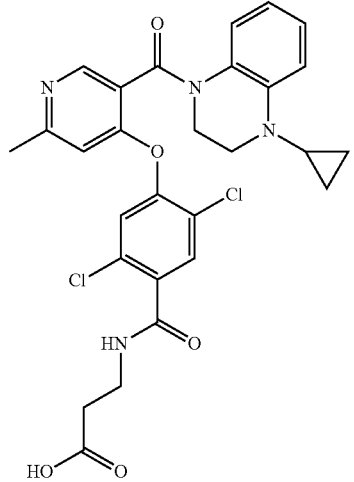 [SMILES: Cc1cc(Oc2cc(Cl)c(C(=O)NCCC(=O)O)cc2Cl)c(C(=O)N2CCN(C3CC3)c3ccccc32)cn1]

To a solution of 83 mg (0.139 mmol) 3-{2,5-dichloro-4-[5-(4-cyclopropyl-3,4-dihydro-2H-quinoxaline-1-carbonyl)-2-methyl-pyridin-4-yloxy]-benzoylamino}-propionic acid ethyl ester in 2 mL dioxane was added 2 mL water and 7 mg (0.174 mmol) lithium hydroxide monohydrate. The reaction mixture was stirred for 4 hours at room temperature. The reaction mixture was poured on 20 mL 1N aqueous hydrochloric acid and 20 mL ethyl acetate and the layers were separated. The aqueous layer was extracted with 20 mL ethyl acetate and the organic layers were washed with 30 mL brine, dried over magnesium sulfate, filtered and concentrated under vacuum to give the title compound as a light yellow solid (100%). MS (ESI): m/z=569.136 [M+H]$^+$.

Example 69

{2,5-Dichloro-4-[5-(4-cyclopropyl-3,4-dihydro-2H-quinoxaline-1-carbonyl)-2-methyl-pyridin-4-yloxy]-benzoylamino}-acetic acid methyl ester

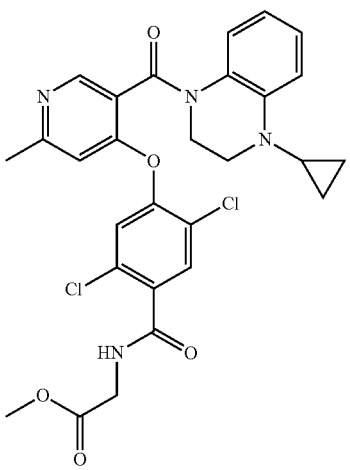 [SMILES: COC(=O)CNC(=O)c1cc(Cl)c(Oc2cc(C)ncc2C(=O)N2CCN(C3CC3)c3ccccc32)cc1Cl]

The title compound was prepared in analogy to Example 29, from 2,5-dichloro-4-[5-(4-cyclopropyl-3,4-dihydro-2H-quinoxaline-1-carbonyl)-2-methyl-pyridin-4-yloxy]-benzoic acid and glycine methyl ester hydrochloride (commercially available, CAS RN 5680-79-5). The compound was purified on a preparative HPLC system (Phenomenex Gemini column) with a gradient of acetonitrile:water (containing 0.05% formic acid) (50:50 to 95:5), to give 44 mg (39%) of the title compound as a light yellow solid. MS (ESI): m/z=569.136 [M+H]$^+$.

Example 70

{2,5-Dichloro-4-[5-(4-cyclopropyl-3,4-dihydro-2H-quinoxaline-1-carbonyl)-2-methyl-pyridin-4-yloxy]-benzoylamino}-acetic acid

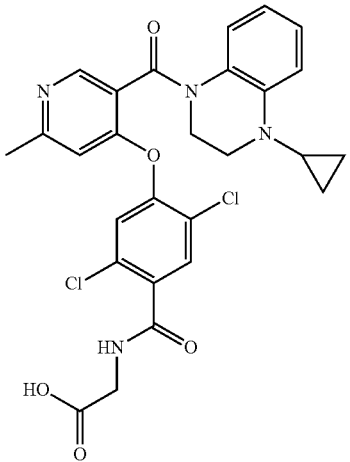 [SMILES: Cc1cc(Oc2cc(Cl)c(C(=O)NCC(=O)O)cc2Cl)c(C(=O)N2CCN(C3CC3)c3ccccc32)cn1]

To a solution of 38 mg (0.067 mmol) {2,5-dichloro-4-[5-(4-cyclopropyl-3,4-dihydro-2H-quinoxaline-1-carbonyl)-2-methyl-pyridin-4-yloxy]-benzoylamino}-acetic acid methyl ester (Example 69) in 2 mL dioxane was added 2 mL water and 4 mg (0.083 mmol) lithium hydroxide monohydrate. The reaction mixture was stirred at room temperature for 4 hours and then poured on 20 mL 1N aqueous hydrochloric acid and 20 mL ethyl acetate. The layers were separated and the aqueous layer was extracted a second time with 20 mL ethyl acetate. The combined organic layers were washed with 30 mL brine, dried over magnesium sulfate, filtered and concentrated under vacuum to yield 10 mg (27%) of the desired compound as a light yellow solid. MS (ESI): m/z=555.119 [M+H]$^+$.

Example 71

2,5-Dichloro-4-[5-(4-cyclopropyl-3,4-dihydro-2H-quinoxaline-1-carbonyl)-2-methyl-pyridin-4-yloxy]-N-(1H-tetrazol-5-yl)-benzamide

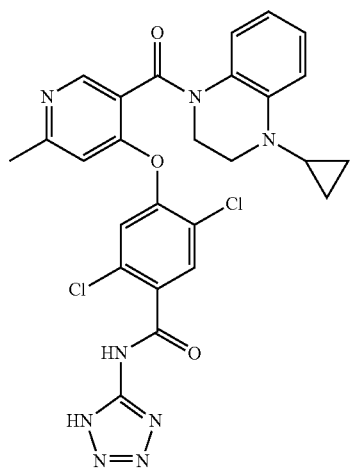 [SMILES: Cc1cc(Oc2cc(Cl)c(C(=O)Nc3nnn[nH]3)cc2Cl)c(C(=O)N2CCN(C3CC3)c3ccccc32)cn1]

The title compound was prepared in analogy to Example 39, from 2,5-dichloro-4-[5-(4-cyclopropyl-3,4-dihydro-2H-quinoxaline-1-carbonyl)-2-methyl-pyridin-4-yloxy]-benzoic acid (Example 66) and 5-amino-1H-tetrazole (commercially available, CAS RN 4418-61-5). The compound was purified twice by preparative HPLC (Phenomenex Gemini column) with a gradient of acetonitrile:water (containing 0.05% formic acid) (50:50 to 95:5) to give 17 mg (15%) of the title compound as a white solid. MS (ESI): m/z=563.109 [M+H]$^+$.

Example 72

2,5-Dichloro-4-[5-(4-cyclopropyl-3,4-dihydro-2H-quinoxaline-1-carbonyl)-2-methyl-pyridin-4-yloxy]-N-(1H-tetrazol-5-ylmethyl)-benzamide

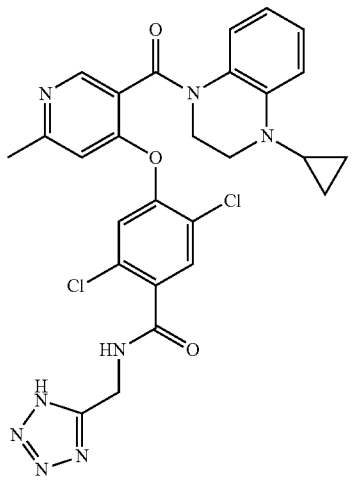 [SMILES: Cc1cc(Oc2cc(Cl)c(C(=O)NCc3nnn[nH]3)cc2Cl)c(C(=O)N2CCN(C3CC3)c3ccccc32)cn1]

The title compound was prepared in analogy to Example 38, from 2,5-dichloro-4-[5-(4-cyclopropyl-3,4-dihydro-2H-quinoxaline-1-carbonyl)-2-methyl-pyridin-4-yloxy]-benzoic acid (Example 66) and 5-(aminomethyl)-tetrazole (commercially available, CAS RN 31602-63-8) to provide 47 mg (40%) of the title compound as a light yellow solid. MS (ESI): m/z=579.142 [M+H]$^+$.

Example 73

[2-Chloro-4-(2,5-dichloro-phenoxy)-6-methyl-pyridin-3-yl]-(4-cyclopropyl-3,4-dihydro-2H-quinoxalin-1-yl)-methanone

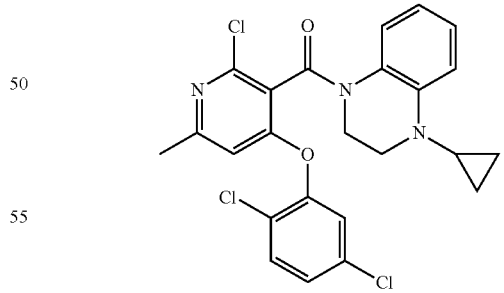

To a solution of 120 mg (0.355 mmol) lithium 2-chloro-4-(2,5-dichloro-phenoxy)-6-methyl-nicotinate in 3 mL dry N,N-dimethylformamide was added 0.30 mL (1.773 mmol) N-ethyldiisopropylamine and 163 mg (0.425 mmol) O-(7-azabenzotriazol-1-yl)-N,N,N;N'-tetramethyluronium hexafluorophosphate (HATU, commercially available, CAS RN 148893-10-1) and 74 mg (0.425 mmol) 1-cyclopropyl-1,2,3,4-tetrahydro-quinoxaline (Example 8, intermediate a).

The reaction mixture was stirred for 18 hours at room temperature and evaporated. The residue was purified on a preparative HPLC system (Phenomenex Gemini column) using a gradient of acetonitrile:water (containing 0.05% formic acid) (50:50 to 100:0) to provide 45 mg (26%) of the title compound as a light yellow foam (30%). MS (ESI): m/z=488.07 [M+H]$^+$.

Intermediates a) Lithium 2-chloro-4-(2,5-dichloro-phenoxy)-6-methyl-nicotinate

To a solution of 130 mg (0.36 mmol) 2-chloro-4-(2,5-dichloro-phenoxy)-6-methyl-nicotinic acid ethyl ester in 2 mL dioxane was added 2 mL water and 23 mg (0.541 mmol) lithium hydroxide monohydrate. The reaction mixture was stirred at 100° C. for 4 hours. The reaction mixture was allowed to cool down to room temperature and was concentrated under high vacuum. The so-obtained light yellow solid was pure enough for the next step without further purification. MS (ESI): 331.965 [M+H]$^+$.

b) 2-Chloro-4-(2,5-dichloro-phenoxy)-6-methyl-nicotinic acid ethyl ester

To a solution of 500 mg (2.136 mmol) ethyl 2,4-dichloro-6-methylpyridine-3-carboxylate (commercially available, CAS RN 86129-63-7) in 7.5 mL dry N,N-dimethylformamide was added 366 mg (2.243 mmol) 2,5-dichlorophenol and 590 mg (4.272 mmol) potassium carbonate and 41 mg (0.214 mmol) copper(I)iodide and 41 mg (0.641 mmol) copper nanopowder (avg. particle size 100 nm). The reaction mixture was stirred at 120° C. for 18 hours and then poured on 30 ml, 1N aqueous hydrochloric acid and 30 mL ethyl acetate. The layers were separated and the aqueous layer was extracted a second time with 30 mL ethyl acetate. The combined organic layers were washed with 30 mL brine, dried over magnesium sulfate, filtered and concentrated under vacuum. The residue was purified by preparative HPLC (Phenomenex Gemini column) with a gradient of acetonitrile:water (50:50 to 100:0) to afford 35 mg (18%) of the title compound as a light yellow oil. MS (ESI): 359.995 [M+H]$^+$.

Example 74

[6-Chloro-4-(2,5-dichloro-phenoxy)-pyridin-3-yl]-(3,4-dihydro-2H-quinolin-1-yl)-methanone

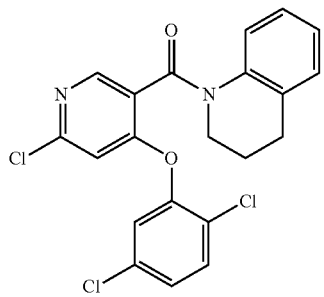 [SMILES: O=C(c1cnc(Cl)cc1Oc1cc(Cl)ccc1Cl)N1CCCc2ccccc21]

To a solution of 0.12 g (0.29 mmol) [4-(2,5-dichloro-phenoxy)-1-oxy-pyridin-3-yl]-(3,4-dihydro-2H-quinolin-1-yl)-methanone (Example 10) in 1 mL toluene was added 0.11 mL (1.15 mmol) phosphorous oxychloride and the resulting suspension was heated to 100° C. The rapidly formed solution was stirred at this temperature for 2.5 hours, after which another 0.11 mL (1.15 mmol) phosphorous oxychloride was added. After stirring for another 2.5 hours the reaction mixture was cooled down to room temperature, poured on saturated aqueous sodium bicarbonate solution and extracted three times with ethyl acetate. The organic layers were washed with brine, dried over magnesium sulfate, filtered, treated with silica gel and evaporated to dryness. The resulting powder was purified by silica gel chromatography using a MPLC system (10 g silica gel column, CombiFlash Companion, Isco Inc.) eluting with a gradient of n-heptane:ethyl acetate (100:0 to 50:50) yielding a light brown solid containing a mixture of the 2- and 4-chloro-substituted compound. The two isomers were separated by preparative HPLC (Chiralpak AD column) using a mixture of ethanol: n-heptane as eluant (30:70) with the desired product eluting second. White solid (0.026 g, 82%). MS (ESI): m/z=433.03 [M+H]$^+$.

Example 75

(4-Cyclopropyl-3,4-dihydro-2H-quinoxalin-1-yl)-[4-(2,5-dichloro-phenoxy)-1-oxy-pyridin-3-yl]-methanone

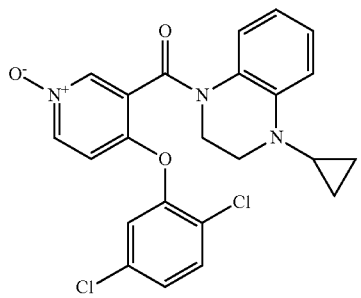 [SMILES: O=C(c1c[n+]([O-])ccc1Oc1cc(Cl)ccc1Cl)N1CCN(C2CC2)c2ccccc21]

To a solution of 230 mg (0.766 mmol) 4-(2,5-dichloro-phenoxy)-1-oxy-nicotinic acid in 3 mL dry N,N-dimethylformamide was added 0.65 mL (3.832 mmol) N-thyldiisopropylamine and 352 mg (0.920 mmol) O-(7-azabenzotriazol-1-yl)-N,N,N',N'-tetramethyluronium hexafluorophosphate (HATU, commercially available, CAS RN 148893-10-1) and 160 mg (0.920 mmol) 1-cyclopropyl-1,2,3,4-tetrahydro-quinoxaline (Example 8, intermediate a). The reaction mixture was stirred at room temperature for 18 hours and then poured on 30 mL 10% aqueous sodium bicarbonate solution and 30 mL ethyl acetate. The layers were separated and the aqueous layer was extracted with 30 mL ethyl acetate. The combined organic layers were washed with 30 mL brine, dried over magnesium sulfate, filtered and concentrated under vacuum. The residue was purified by preparative HPLC (Phenomenex Gemini column) with a gradient of acetonitrile:water (containing 0.05% formic acid) (10:90 to 98:2). MS (ESI): m/z=456.087 [M+H]$^+$.

Intermediate 4-(2,5-Dichloro-phenoxy)-1-oxy-nicotinic acid

To a suspension of 0.5 g (1.760 mmol) 4-(2,5-dichloro-phenoxy)-nicotinic acid (Example 1, intermediate) in 7.5 mL dichloromethane was added 0.542 g (2.200 mmol) m-chloroperbenzoic acid (Aldrich, CAS RN 937-14-4) at 0° C. The reaction mixture was stirred for 3 hours at room temperature. The white suspension was filtered and washed with 10 mL dichloromethane to give 492 mg (86%) of the desired compound as a white solid. MS (ESI): m/z=299.983 [M+H]⁺.

Example 76

[4-(2,5-Dichloro-phenoxy)-pyrimidin-5-yl]-(3,4-dihydro-2H-quinolin-1-yl)-methanone

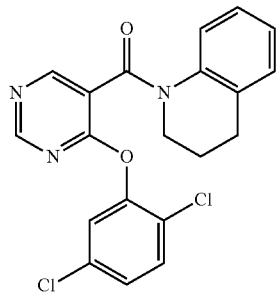 [SMILES: O=C(c1cncnc1Oc1cc(Cl)ccc1Cl)N1CCCc2ccccc21]

To a solution of 200 mg (0.7 mmol) 4-(2,5-dichloro-phenoxy)-pyrimidine-5-carboxylic acid in 2 mL dichloromethane were added 197 mg (0.77 mmol) 2-chloro-1-methylpyridinium iodide (commercially available, CAS RN 14338-32-0), 0.2 mL (1.4 mmol) triethylamine and 103 mg (0.77 mmol) 1,2,3,4-tetrahydroquinoline (commercially available, CAS RN 635-46-1). The solution was stirred 2 hours at room temperature. The reaction mixture was poured on saturated aqueous sodium bicarbonate solution and extracted three times with dichloromethane. The combined organic layers were dried over magnesium sulfate and concentrated under vacuum. The residue was purified by preparative HPLC (Phenomenex Gemini column) using a gradient of acetonitrile:water (containing 0.05% formic acid) (10:90 to 98:2) to give 5.6 mg (2%) of the desired compound. MS (ESI): m/z=400.2 [M+H]⁺.

Intermediates a)
4-(2,5-Dichloro-phenoxy)-pyrimidine-5-carboxylic acid

To a solution of 515 mg (1.64 mmol) 4-(2,5-dichloro-phenoxy)-pyrimidine-5-carboxylic acid ethyl ester in 10 mL tetrahydrofuran/water (2/1 v/v) was added 3.29 mL (3.28 mmol) 1M aqueous sodium hydroxide solution and the resulting solution was heated by microwave irradiation (Emrys Optimizer, Personal Chemistry) 30 minutes at 80° C. Solvents were evaporated under vacuum and the residue extracted three times with ethyl acetate and 1M aqueous hydrochloric acid. The combined organic layers were dried over magnesium sulfate, filtered and evaporated to give 385 mg (57%) of the desired compound as an off-white powder. MS (ESI): m/z=238.8 [M–H]⁻.

b)
4-(2,5-Dichloro-phenoxy)-pyrimidine-5-carboxylic acid ethyl ester

To a solution of 420 mg (2.25 mmol) 4-chloropyrimidine-5-carboxylic acid ethyl ester (commercially available, CAS RN 41103-17-7) and 440 mg (2.7 mmol) 2,5-dichlorophenol (commercially available, CAS RN 583-78-8) in 2.5 mL toluene were added 688 mg (5.17 mmol) cesium carbonate and 168 mg (0.45 mmol) tetrakis(acetonitrile) copper(I) hexafluorophosphate (commercially available, CAS RN 64443-05-6). The reaction was heated to reflux for 2.5 h. The solvent was evaporated and the crude reaction product extracted with ethyl acetate from an aqueous saturated solution of sodium bicarbonate. The organic layer was dried over magnesium sulfate, filtered and evaporated. The resulting product was purified by silica gel chromatography using a MPLC system (silica gel column, CombiFlash Companion, Isco Inc.) eluting with a gradient of n-heptane:ethyl acetate yielding 620 mg (88%) of the desired compound as a light yellow viscous oil. MS (ESI): m/z=313.1 [M+H]⁺.

Example 77

[4-(2,5-Dichloro-phenoxy)-pyrimidin-5-yl]-(6-fluoro-3,4-dihydro-2H-quinolin-1-yl)-methanone

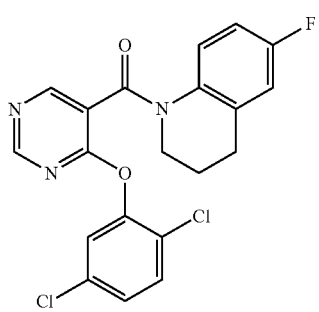 [SMILES: O=C(c1cncnc1Oc1cc(Cl)ccc1Cl)N1CCCc2cc(F)ccc21]

To a solution of 57 mg (0.2 mmol) 4-(2,5-dichloro-phenoxy)-pyrimidine-5-carboxylic acid (Example 76, intermediate a) in 1.5 mL N,N-dimethylformamide were added 91 mg (0.24 mmol) O-(7-azabenzotriazol-1-yl)-N,N,N',N'-tetramethyluronium hexafluorophosphate (HATU, commercially available, CAS RN 148893-10-1) and 0.102 mL (0.6 mmol) N,N-diisopropyl-ethylamine. The solution was stirred 15 minutes at 45° C. followed by addition of 36 mg (0.22 mmol) 6-fluoro-1,2,3,4-tetrahydroquinoline (commercially available, CAS RN 59611-52-8). The reaction was stirred at 45° C. overnight and purified on a preparative HPLC system (Phenomenex Gemini column) using a gradient of acetonitrile:water (containing 0.05% formic acid) (10:90 to 98:2) to give 2.5 mg (3%) of the desired compound. MS (ESI): m/z=418.1 [M+H]⁺.

Example 78

[4-(2,5-Dichloro-phenoxy)-pyrimidin-5-yl]-(3,4-dihydro-2H-quinoxalin-1-yl)-methanone

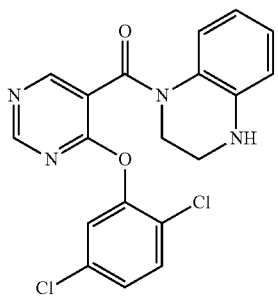 [SMILES: O=C(c1cncnc1Oc1cc(Cl)ccc1Cl)N1CCNc2ccccc21]

The title compound was prepared in analogy to Example 77, from 4-(2,5-dichloro-phenoxy)-pyrimidine-5-carboxylic acid (Example 76, intermediate a) and 1,2,3,4-tetrahydroquinoxaline (commercially available, CAS RN 3476-89-9). The compound was purified by preparative HPLC (Phenomenex Gemini column) using a gradient of acetonitrile:water (10:90 to 98:2) to give 16 mg (20%) of the desired compound. MS (ESI): m/z=401.0 [M+H]$^+$.

Example 79

[4-(2,5-Dichloro-phenoxy)-pyrimidin-5-yl]-(4-methyl-3,4-dihydro-2H-quinoxalin-1-yl)-methanone

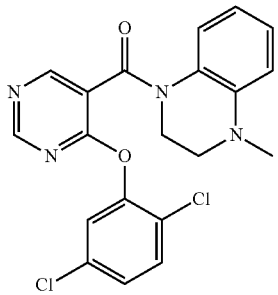 [SMILES: CN1CCN(C(=O)c2cncnc2Oc2cc(Cl)ccc2Cl)c2ccccc21]

The title compound was prepared in analogy to Example 77, from 4-(2,5-dichloro-phenoxy)-pyrimidine-5-carboxylic acid and 1-methyl-1,2,3,4-tetrahydroquinoxaline (commercially available, Metina, catalog number M-636). The compound was purified by preparative HPLC (Phenomenex Gemini column) using a gradient of acetonitrile:water (10:90 to 98:2) to give 6.5 mg (8%) of the desired compound. MS (ESI): m/z=415.1 [M+H]$^+$.

Example 80

4-(2,5-Dichloro-phenoxy)-pyrimidine-5-carboxylic acid (2-methoxy-pyridin-3-yl)-methyl-amide

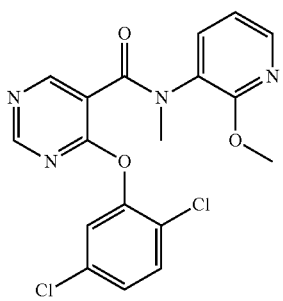 [SMILES: COc1ncccc1N(C)C(=O)c1cncnc1Oc1cc(Cl)ccc1Cl]

To a solution of 50 mg (0.17 mmol) (4-(2,5-dichloro-phenoxy)-pyrimidine-5-carboxylic acid (Example 76, intermediate a) in 1.5 mL dichloromethane were added 0.05 mL (0.34 mmol) triethylamine and 49 mg (0.19 mmol) 2-chloro-1-methylpyridinium iodide. After stirring at room temperature for 20 minutes, 24 mg (0.19 mmol) 2-methoxypyridin-3-amine (commercially available, CAS RN 20265-38-7) were added. After 2 hours, the reaction mixture was poured on water and extracted with dichloromethane. The organic layer was dried over magnesium sulfate, filtered and evaporated. The crude product was dissolved in 1 mL N,N-dimethylformamide and 14 mg (0.35 mmol) sodium hydride (60% suspension in mineral oil) followed by 0.02 mL (0.35 mmol) of methyliodide were added. The reaction was stirred at 50° C. for 2 hours. The suspension was filtered using a syringe micro filter and purified on a preparative HPLC system (Phenomenex Gemini column) using a gradient of acetonitrile:water (containing 0.05% formic acid) (10:90 to 98:2) to give 28 mg (39%) of the desired compound as a light brown solid. MS (ESI): m/z=405.0 [M+H]$^+$.

Example A

Film coated tablets containing the following ingredients can be manufactured in a conventional manner:

| Ingredients | Per tablet | |
|---|---|---|
| Kernel: | | |
| Compound of formula I | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titan dioxide | 0.8 mg | 1.6 mg |

The active ingredient is sieved and mixed with microcrystalline cellulose and the mixture is granulated with a solution of polyvinylpyrrolidone in water. The granulate is mixed with sodium starch glycolate and magesiumstearate and compressed to yield kernels of 120 or 350 mg respectively. The kernels are lacquered with an aqueous solution/suspension of the above mentioned film coat.

Example B

Capsules containing the following ingredients can be manufactured in a conventional manner:

| Ingredients | Per capsule |
|---|---|
| Compound of formula I | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| Compound of formula I | 3.0 mg |
|---|---|
| Polyethylene Glycol 400 | 150.0 mg |
| Acetic Acid | q.s. ad pH 5.0 |
| Water for injection solutions | ad 1.0 ml |

The active ingredient is dissolved in a mixture of Polyethylene Glycol 400 and water for injection (part). The pH is adjusted to 5.0 by Acetic Acid. The volume is adjusted to 1.0 ml by addition of the residual amount of water. The solution is filtered, filled into vials using an appropriate overage and sterilized.

Example D

Soft gelatin capsules containing the following ingredients can be manufactured in a conventional manner:

| Capsule contents | |
| --- | --- |
| Compound of formula I | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titan dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example E

Sachets containing the following ingredients can be manufactured in a conventional manner:

| Compound of formula I | 50.0 mg |
| --- | --- |
| Lactose, fine powder | 1015.0 mg |
| Microcristalline cellulose (AVICEL PH 102) | 1400.0 mg |
| Sodium carboxymethyl cellulose | 14.0 mg |
| Polyvinylpyrrolidon K 30 | 10.0 mg |
| Magnesiumstearate | 10.0 mg |
| Flavoring additives | 1.0 mg |

The active ingredient is mixed with lactose, microcristalline cellulose and sodium carboxymethyl cellulose and granulated with a mixture of polyvinylpyrrolidone in water. The granulate is mixed with magnesiumstearate and the flavoring additives and filled into sachets.

The invention claimed is:
1. A compound of formula I,

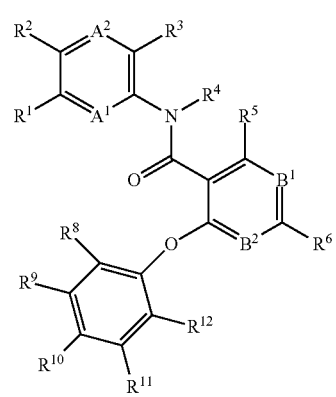

wherein
$A^1$ is $CR^{13}$ and $A^2$ is N or $A^1$ is N and $A^2$ is $CR^{14}$;
$R^1$ and $R^2$ are independently from each other selected from the group consisting of hydrogen, $C_{1-7}$-alkyl, halogen, halogen-$C_{1-7}$-alkyl, cyano and $C_{1-7}$-alkoxy;
$R^{13}$ and $R^{14}$ are independently from each other selected from the group consisting of hydrogen, $C_{1-7}$-alkyl, halogen, halogen-$C_{1-7}$-alkyl, cyano, $C_{1-7}$-alkoxy, amino and $C_{1-7}$-alkylsulfanyl;
$R^3$ is selected from the group consisting of hydrogen, $C_{1-7}$-alkyl, halogen, halogen-$C_{1-7}$-alkyl, $C_{1-7}$-alkoxy, cyano, $C_{3-7}$-cycloalkyl, N-heterocyclyl, five-membered heteroaryl, phenyl and —$NR^{15}R^{16}$, wherein $R^{15}$ and $R^{16}$ independently from each other are selected from hydrogen, $C_{1-7}$-alkyl and $C_{3-7}$-cycloalkyl;
$R^4$ is selected from the group consisting of hydrogen, $C_{1-7}$-alkyl, halogen-$C_{1-7}$-alkyl and $C_{3-7}$-cycloalkyl; or
$B^1$ is N or $N^+$—$O^-$;
$B^2$ is $CR^7$ or N;
$R^5$, $R^6$ and $R^7$ independently from each other are selected from the group consisting of hydrogen, halogen, $C_{1-7}$-alkyl, $C_{1-7}$-alkoxy, halogen-$C_{1-7}$-alkyl, halogen-$C_{1-7}$-alkoxy, and cyano;
and $R^8$, $R^9$, $R^{10}$, $R^{11}$ and $R^{12}$ are independently from each other selected from the group consisting of hydrogen, $C_{1-7}$-alkyl, $C_{2-7}$-alkenyl, $C_{2-7}$-alkinyl, halogen, halogen-$C_{1-7}$-alkyl, $C_{1-7}$-alkoxy, halogen-$C_{1-7}$-alkoxy, hydroxy, hydroxy-$C_{1-7}$-alkoxy, hydroxy-$C_{1-7}$-alkyl, hydroxy-$C_{3-7}$-alkenyl, hydroxy-$C_{3-7}$-alkinyl, cyano, carboxyl, $C_{1-7}$-alkoxycarbonyl, aminocarbonyl, carboxyl-$C_{1-7}$-alkyl, carboxyl-$C_{2-7}$-alkenyl, carboxyl-$C_{2-7}$-alkinyl, $C_{1-7}$-alkoxycarbonyl-$C_{1-7}$-alkyl, $C_{1-7}$-alkoxycarbonyl-$C_{2-7}$-alkenyl, $C_{1-7}$-alkoxycarbonyl-$C_{2-7}$-alkinyl, carboxyl-$C_{1-7}$-alkoxy, $C_{1-7}$-alkoxycarbonyl-$C_{1-7}$-alkoxy, carboxyl-$C_{1-7}$-alkyl-aminocarbonyl, carboxyl-$C_{1-7}$-alkyl-($C_{1-7}$-alkylamino)-carbonyl, $C_{1-7}$-alkoxycarbonyl-$C_{1-7}$-alkyl-aminocarbonyl, $C_{1-7}$-alkoxycarbonyl-$C_{1-7}$-alkyl-($C_{1-7}$-alkylamino)-carbonyl, carboxyl-$C_{1-7}$-alkyl-aminocarbonyl-$C_{1-7}$-alkyl, carboxyl-$C_{1-7}$-alkyl-($C_{1-7}$-alkylamino)-carbonyl-$C_{1-7}$-alkyl, $C_{1-7}$-alkoxycarbonyl-$C_{1-7}$-alkyl-aminocarbonyl-$C_{1-7}$-alkyl, $C_{1-7}$-alkoxycarbonyl-$C_{1-7}$-alkyl-($C_{1-7}$-alkylamino)-carbonyl-$C_{1-7}$-alkyl, hydroxy-$C_{1-7}$-alkyl-aminocarbonyl, di-(hydroxy-$C_{1-7}$-alkyl)aminocarbonyl, aminocarbonyl-$C_{1-7}$-alkyl-aminocarbonyl, hydroxysulfonyl-$C_{1-7}$-alkyl-aminocarbonyl, hydroxysulfonyl-$C_{1-7}$-alkyl-($C_{1-7}$-alkyl-amino)-carbonyl, di-($C_{1-7}$-alkoxycarbonyl-$C_{1-7}$-alkyl)-methylaminocarbonyl, phenyl optionally substituted by one to three groups selected from halogen, $C_{1-7}$-alkoxy, carboxyl or $C_{1-7}$-alkoxycarbonyl, phenyl-carbonyl wherein the phenyl is optionally substituted by one to three groups selected from halogen, $C_{1-7}$-alkoxy, carboxyl and $C_{1-7}$-alkoxycarbonyl, phenyl-aminocarbonyl wherein the phenyl is optionally substituted by one to three groups selected from halogen, $C_{1-7}$-alkoxy, carboxyl and $C_{1-7}$-alkoxycarbonyl, phenyl-$C_{1-7}$-alkyl wherein the phenyl is optionally substituted by one to three groups selected from halogen, $C_{1-7}$-alkoxy, carboxyl and $C_{1-7}$-alkoxycarbonyl, phenyl-$C_{2-7}$-alkinyl wherein the phenyl is optionally substituted by one to three groups selected from halogen, $C_{1-7}$-alkoxy, carboxyl and $C_{1-7}$-alkoxycarbonyl, heteroaryl optionally substituted by one to three groups selected from halogen, $C_{1-7}$-alkoxy, carboxyl and $C_{1-7}$-alkoxycarbonyl, heteroaryl-carbonyl wherein the heteroaryl is optionally substituted by one to three groups selected from halogen, $C_{1-7}$-alkoxy, carboxyl and $C_{1-7}$-alkoxycarbonyl, heteroaryl-aminocarbonyl wherein the heteroaryl is optionally substituted by one to three groups selected from halogen, $C_{1-7}$-alkoxy, carboxyl and $C_{1-7}$-alkoxycarbonyl, heteroaryl-$C_{1-7}$-alkyl wherein the heteroaryl is optionally substituted by one to three groups selected from halogen, $C_{1-7}$-alkyl, $C_{1-7}$-alkoxy, carboxyl and $C_{1-7}$-alkoxycarbonyl, heteroaryl-$C_{1-7}$-alkyl-aminocarbonyl wherein the heteroaryl is optionally substituted by one to three groups selected from halogen, $C_{1-7}$-alkoxy, carboxyl and $C_{1-7}$-alkoxycarbonyl, and heteroaryl-carbonyl-$C_{1-7}$-alkyl wherein the heteroaryl is optionally substituted by one to three groups selected from halogen, $C_{1-7}$-alkoxy, carboxyl and $C_{1-7}$-alkoxycarbonyl;

or a pharmaceutically acceptable salt thereof.

2. A compound according to claim 1, wherein $A^1$ is $CR^{13}$, $A^2$ is N, and $R^{13}$ is selected from the group consisting of hydrogen, halogen, halogen-$C_{1-7}$-alkyl and $C_{1-7}$-alkoxy.

3. A compound according to claim 1, wherein $R^1$ and $R^2$ are independently from each other selected from the group consisting of hydrogen, halogen and halogen-$C_{1-7}$-alkyl.

4. A compound according to claim 1, wherein $R^3$ is selected from the group consisting of hydrogen, $C_{1-7}$-alkyl, $C_{1-7}$-alkoxy, N-heterocyclyl and —$NR^{15}R^{16}$, wherein $R^{15}$ and $R^{16}$ independently from each other are selected from hydrogen, $C_{1-7}$-alkyl and $C_{3-7}$-cycloalkyl, and $R^4$ is hydrogen or methyl.

5. A compound according to claim 1, wherein $B^1$ is N or $N^+$—$O^-$ and $B^2$ is $CR^7$, with $R^7$ being selected from the group consisting of hydrogen, halogen and $C_{1-7}$-alkyl.

6. A compound according to claim 1, wherein $R^5$ and $R^6$ are independently from each other selected from the group consisting of hydrogen, halogen and $C_{1-7}$-alkyl.

7. A compound according to claim 1, wherein at least two of $R^8$, $R^9$, $R^{10}$, $R^{11}$ and $R^{12}$ are selected from the group consisting of $C_{1-7}$-alkyl, $C_{2-7}$-alkenyl, $C_{2-7}$-alkinyl, halogen, halogen-$C_{1-7}$-alkyl, $C_{1-7}$-alkoxy, halogen-$C_{1-7}$-alkoxy, hydroxy, hydroxy-$C_{1-7}$-alkoxy, hydroxy-$C_{1-7}$-alkyl, hydroxy-$C_{3-7}$-alkenyl, hydroxy-$C_{3-7}$-alkinyl, cyano, carboxyl, $C_{1-7}$-alkoxycarbonyl, aminocarbonyl, carboxyl-$C_{1-7}$-alkyl, carboxyl-$C_{2-7}$-alkenyl, carboxyl-$C_{2-7}$-alkinyl, $C_{1-7}$-alkoxycarbonyl-$C_{1-7}$-alkyl, $C_{1-7}$-alkoxycarbonyl-$C_{2-7}$-alkenyl, $C_{1-7}$-alkoxycarbonyl-$C_{2-7}$-alkinyl, carboxyl-$C_{1-7}$-alkoxy, $C_{1-7}$-alkoxycarbonyl-$C_{1-7}$-alkoxy, carboxyl-$C_{1-7}$-alkyl-aminocarbonyl, carboxyl-$C_{1-7}$-alkyl-($C_{1-7}$-alkylamino)-carbonyl, $C_{1-7}$-alkoxycarbonyl-$C_{1-7}$-alkyl-aminocarbonyl, $C_{1-7}$-alkoxycarbonyl-$C_{1-7}$-alkyl-($C_{1-7}$-alkylamino)-carbonyl, carboxyl-$C_{1-7}$-alkyl-aminocarbonyl-$C_{1-7}$-alkyl, carboxyl-$C_{1-7}$-alkyl-($C_{1-7}$-alkylamino)-carbonyl-$C_{1-7}$-alkyl, $C_{1-7}$-alkoxycarbonyl-$C_{1-7}$-alkyl-aminocarbonyl-$C_{1-7}$-alkyl, $C_{1-7}$-alkoxycarbonyl-$C_{1-7}$-alkyl-($C_{1-7}$-alkylamino)-carbonyl-$C_{1-7}$-alkyl, hydroxy-$C_{1-7}$-alkyl-aminocarbonyl, di-(hydroxy-$C_{1-7}$alkyl)aminocarbonyl, aminocarbonyl-$C_{1-7}$-alkyl-aminocarbonyl, hydroxysulfonyl-$C_{1-7}$-alkyl-aminocarbonyl, hydroxysulfonyl-$C_{1-7}$-alkyl-($C_{1-7}$-alkyl-amino)-carbonyl, di-($C_{1-7}$-alkoxycarbonyl-$C_{1-7}$-alkyl)-methylaminocarbonyl, phenyl optionally substituted by one to three groups selected from halogen, $C_{1-7}$-alkoxy, carboxyl and $C_{1-7}$-alkoxycarbonyl, phenyl-carbonyl wherein the phenyl is optionally substituted by one to three groups selected from halogen, $C_{1-7}$-alkoxy, carboxyl and $C_{1-7}$-alkoxycarbonyl, phenyl-aminocarbonyl wherein the phenyl is optionally substituted by one to three groups selected from halogen, $C_{1-7}$-alkoxy, carboxyl and $C_{1-7}$-alkoxycarbonyl, phenyl-$C_{1-7}$-alkyl wherein the phenyl is optionally substituted by one to three groups selected from halogen, $C_{1-7}$-alkoxy, carboxyl and $C_{1-7}$-alkoxycarbonyl, phenyl-$C_{1-7}$-alkinyl wherein the phenyl is optionally substituted by one to three groups selected from halogen, $C_{1-7}$-alkoxy, carboxyl and $C_{1-7}$-alkoxycarbonyl, heteroaryl optionally substituted by one to three groups selected from halogen, $C_{1-7}$-alkoxy, carboxyl and $C_{1-7}$-alkoxycarbonyl, heteroaryl-carbonyl wherein the heteroaryl is optionally substituted by one to three groups selected from halogen, $C_{1-7}$-alkoxy, carboxyl and $C_{1-7}$-alkoxycarbonyl, heteroaryl-aminocarbonyl wherein the heteroaryl is optionally substituted by one to three groups selected from halogen, $C_{1-7}$-alkoxy, carboxyl and $C_{1-7}$-alkoxycarbonyl, heteroaryl-$C_{1-7}$-alkyl wherein the heteroaryl is optionally substituted by one to three groups selected from halogen, $C_{1-7}$-alkoxy, carboxyl and $C_{1-7}$-alkoxycarbonyl, heteroaryl-$C_{1-7}$-alkyl wherein the heteroaryl is optionally substituted by one to three groups selected from halogen, $C_{1-7}$-alkyl, $C_{1-7}$-alkoxy, carboxyl and $C_{1-7}$-alkoxycarbonyl, heteroaryl-$C_{1-7}$-alkyl-aminocarbonyl wherein the heteroaryl is optionally substituted by one to three groups selected from halogen, $C_{1-7}$-alkoxy, carboxyl and $C_{1-7}$-alkoxycarbonyl, and heteroaryl-carbonyl- $C_{1-7}$-alkyl wherein the heteroaryl is optionally substituted by one to three groups selected from halogen, $C_{1-7}$-alkoxy, carboxyl and $C_{1-7}$-alkoxycarbonyl, and the other ones of $R^8$, $R^9$, $R^{10}$, $R^{11}$ and $R^{12}$ are hydrogen.

8. A compound according to claim 1, wherein at least two of $R^8$, $R^9$, $R^{10}$, $R^{11}$ and $R^{12}$ are selected from the group consisting of halogen, hydroxy, hydroxy-$C_{1-7}$-alkoxy, hydroxy-$C_{1-7}$-alkyl, cyano, carboxyl, $C_{1-7}$-alkoxycarbonyl, aminocarbonyl, carboxyl-$C_{1-7}$-alkoxy, $C_{1-7}$-alkoxycarbonyl-$C_{1-7}$-alkoxy, carboxyl-$C_{1-7}$-alkyl-aminocarbonyl, carboxyl-$C_{1-7}$-alkyl-($C_{1-7}$-alkylamino)-carbonyl, $C_{1-7}$-alkoxycarbonyl-$C_{1-7}$-alkyl-aminocarbonyl, hydroxy-$C_{1-7}$-alkyl-aminocarbonyl, di-(hydroxy-$C_{1-7}$-alky) aminocarbonyl, aminocarbonyl-$C_{1-7}$-alkyl-aminocarbonyl, hydroxysulfonyl-$C_{1-7}$-alkyl-aminocarbonyl, hydroxysulfonyl-$C_{1-7}$-alkyl-($C_{1-7}$-alkyl-amino)-carbonyl, di-($C_{1-7}$-alkoxycarbonyl-$C_{1-7}$-alkyl)-methylaminocarbonyl, phenyl-aminocarbonyl wherein the phenyl is optionally substituted by one to three groups selected from halogen, $C_{1-7}$-alkoxy, carboxyl and $C_{1-7}$-alkoxycarbonyl, heteroaryl-aminocarbonyl wherein the heteroaryl is optionally substituted by one to three groups selected from halogen, $C_{1-7}$-alkoxy, carboxyl and $C_{1-7}$-alkoxycarbonyl, heteroaryl-$C_{1-7}$-alkyl wherein the heteroaryl is optionally substituted by one to three groups selected from halogen, $C_{1-7}$-alkyl, $C_{1-7}$-alkoxy, carboxyl and $C_{1-7}$-alkoxycarbonyl, heteroaryl-$C_{1-7}$-alkyl-aminocarbonyl wherein the heteroaryl is optionally substituted by one to three groups selected from halogen, $C_{1-7}$-alkoxy, carboxyl and $C_{1-7}$-alkoxycarbonyl, and heteroaryl-carbonyl-$C_{1-7}$-alkyl wherein the heteroaryl is optionally substituted by one to three groups selected from halogen, $C_{1-7}$-alkoxy, carboxyl and $C_{1-7}$-alkoxycarbonyl, and the other ones of $R^8$, $R^9$, $R^{10}$, $R^{11}$ and $R^{12}$ are hydrogen.

9. A compound according to claim 1, wherein $R^8$ and $R^{11}$ are halogen and $R^9$, $R^{10}$ and $R^{12}$ are hydrogen.

10. A compound according to claim 1, which is
4-(2,5-dichloro-phenoxy)-N-(2-methoxy-pyridin-3-yl)-N-methyl-nicotinamide, and
4-(2,5-dichloro-phenoxy)-N-(2-dimethylamino-pyridin-3yl)-N-methyl-nicotinamide, and
pharmaceutically-acceptable salts thereof.

11. A compound according to claim 1, which is
4-(2,5-dichloro-phenoxy)-pyrimidine-5-carboxylic acid (2-methoxy-pyridin-3-yl)-methyl-amide, and pharmaceutically acceptable salts thereof.

12. A pharmaceutical composition comprising a compound according to claim 1 and a pharmaceutically acceptable carrier and/or adjuvant.

* * * * *